US012559563B2

(12) United States Patent
Powell et al.

(10) Patent No.: US 12,559,563 B2
(45) Date of Patent: Feb. 24, 2026

(54) MÜLLERIAN INHIBITING SUBSTANCE TYPE 2 RECEPTOR (MISIIR)-SPECIFIC CAR T CELLS FOR THE TREATMENT OF OVARIAN CANCER AND OTHER GYNECOLOGIC MALIGNANCIES

(71) Applicant: THE TRUSTEES OF THE UNIVERSITY OF PENNSYLVANIA, Philadelphia, PA (US)

(72) Inventors: Daniel J. Powell, Bala Cynwyd, PA (US); Alba Rodriguez-Garcia, Philadelphia, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 1150 days.

(21) Appl. No.: 17/603,539

(22) PCT Filed: Apr. 14, 2020

(86) PCT No.: PCT/US2020/028073
§ 371 (c)(1),
(2) Date: Oct. 13, 2021

(87) PCT Pub. No.: WO2020/214563
PCT Pub. Date: Oct. 22, 2020

(65) Prior Publication Data
US 2022/0213205 A1 Jul. 7, 2022

Related U.S. Application Data

(60) Provisional application No. 62/834,104, filed on Apr. 15, 2019.

(51) Int. Cl.
| | |
|---|---|
| *C07K 16/28* | (2006.01) |
| *A61K 35/17* | (2025.01) |
| *A61K 40/11* | (2025.01) |
| *A61K 40/31* | (2025.01) |
| *A61K 40/42* | (2025.01) |
| *A61P 35/00* | (2006.01) |
| *C07K 14/705* | (2006.01) |
| *C07K 14/725* | (2006.01) |
| *A61K 38/00* | (2006.01) |
| *A61K 39/00* | (2006.01) |

(52) U.S. Cl.
CPC .......... *C07K 16/2869* (2013.01); *A61K 40/11* (2025.01); *A61K 40/31* (2025.01); *A61K 40/4202* (2025.01); *A61K 40/4211* (2025.01); *A61P 35/00* (2018.01); *C07K 14/7051* (2013.01); *C07K 14/70517* (2013.01); *C07K 14/70578* (2013.01); *A61K 38/00* (2013.01); *A61K 2039/505* (2013.01); *A61K 2239/59* (2023.05); *C07K 2317/53* (2013.01); *C07K 2317/622* (2013.01); *C07K 2317/73* (2013.01); *C07K 2317/92* (2013.01); *C07K 2319/02*

(2013.01); *C07K 2319/03* (2013.01); *C07K 2319/30* (2013.01); *C07K 2319/33* (2013.01)

(58) Field of Classification Search
CPC ....................... C07K 16/2869; C07K 2317/73; A61K 40/11; A61K 40/31; A61K 40/4202; A61K 48/00
See application file for complete search history.

(56) References Cited

U.S. PATENT DOCUMENTS

| | | | |
|---|---|---|---|
| 8,198,411 B2 | 6/2012 | Adams et al. | |
| 2010/0278728 A1 * | 11/2010 | Adams ................... | A61P 35/00 435/7.1 |
| 2014/0286973 A1 | 9/2014 | Powell, Jr. et al. | |
| 2018/0044424 A1 * | 2/2018 | June ................... | C07K 16/2803 |

FOREIGN PATENT DOCUMENTS

| | | | |
|---|---|---|---|
| WO | 2018/0189379 A1 | 10/2018 | |
| WO | WO-2018189379 A1 * | 10/2018 | ........... A61K 31/513 |

OTHER PUBLICATIONS

Anti-Müllerian hormone receptor type 2 (AMHR2): https://www. genecards.org/cgi-bin/carddisp.pl?gene=AMHR2&keywords= MISRII (Year: 2025).*
Chang, Z.L. and Chen, Y.Y., 2017. CARs: synthetic immunoreceptors for cancer therapy and beyond. Trends in molecular medicine, 23(5), pp. 430-450. (Year: 2017).*
Bakkum-Gamez JN, Aletti G, Lewis KA, et al. Müllerian inhibiting substance type II receptor (MISIIR): A novel, tissue-specific target expressed by gynecologic cancers. Gynecol Oncol 2008, 108:141-148.
Kersual, N., Garambois, V., Chardès, T., Pouget, J.P., Salhi, I., Bascoul-Mollevi, C., Bibeau, F., Busson, M., Vié, H., Clémenceau, B., et al. (2014). The human Müllerian inhibiting substance type II receptor as immunotherapy target for ovarian cancer. Validation using the mAb 12G4. MAbs 6, 1314-1326.
Masiakos PT, MacLaughlin DT, Maheswaran S, et al. Human Ovarian Cancer, Cell Lines, and Primary Ascites Cells Express the Human Mullerian Inhibiting Substance (MIS) Type II Receptor, Bind, and Are Responsive to MIS. Clinic Cancer Res 1999, 5:3488-3499.

(Continued)

*Primary Examiner* — Fereydoun G Sajjadi
*Assistant Examiner* — Masudur Rahman
(74) *Attorney, Agent, or Firm* — Saul Ewing LLP; Kathryn Doyle; Justin Crotty

(57) ABSTRACT

The present disclosure provides modified immune cells or precursors thereof (e.g., modified T cells) comprising a chimeric antigen receptor (CAR) having affinity for Müllerian inhibiting substance type 2 receptor (MISIIR). Compositions and methods of treatment of diseases and disorders, such as ovarian and other gynecologic cancers, are also provided. Additionally provided herein are modified immune cells or precursor cells thereof comprising a nucleic acid encoding a CAR having affinity for Müllerian inhibiting substance type 2 receptor (MISIIR).

5 Claims, 36 Drawing Sheets
Specification includes a Sequence Listing.

(56) References Cited

OTHER PUBLICATIONS

Renaud, E.J., MacLaughlin, D.T., Oliva, E., Rueda, B.R., and Donahoe, P.K. (2005). Endometrial cancer is a receptor-mediated target for Mullerian inhibiting substance. Proc. Natl. Acad. Sci. USA 102, 111-116.

Salhi, I., Cambon-Roques, S., Lamarre, I., Laune, D., Molina, F., Pugnière, M., Pourquier, D., Gutowski, M., Picard, J. Y., Xavier, F., et al. (2004). The anti-Müllerian hormone type II receptor: insights into the binding domains recognized by a monoclonal antibody and the natural ligand. Biochem. J. 379, 785-793.

Song, D.G., and Powell, D.J. (2012). Pro-survival signaling via CD27 costimulation drives effective CAR T-cell therapy. OncoImmunology 1, 547-549.

Yuan QA, Robinson MK, Simmons HH, et al. Isolation of anti-MISIIR scFv molecules from a phage display library by cell sorter biopanning. Cancer Immunol Immunother 2008, 57:367-378.

Yuan QA, Simmons HH, Robinson MK, et al. Development of engineered antibodies specific for the Mullerian inhibiting substance type II receptor: a promising candidate for targeted therapy of ovarian cancer. Mol Can Ther 2006, 5 (8):2096-105.

International Search Report and Written Opinion dated Sep. 21, 2020 from corresponding International Patent Application No. PCT/US20/28073.

* cited by examiner

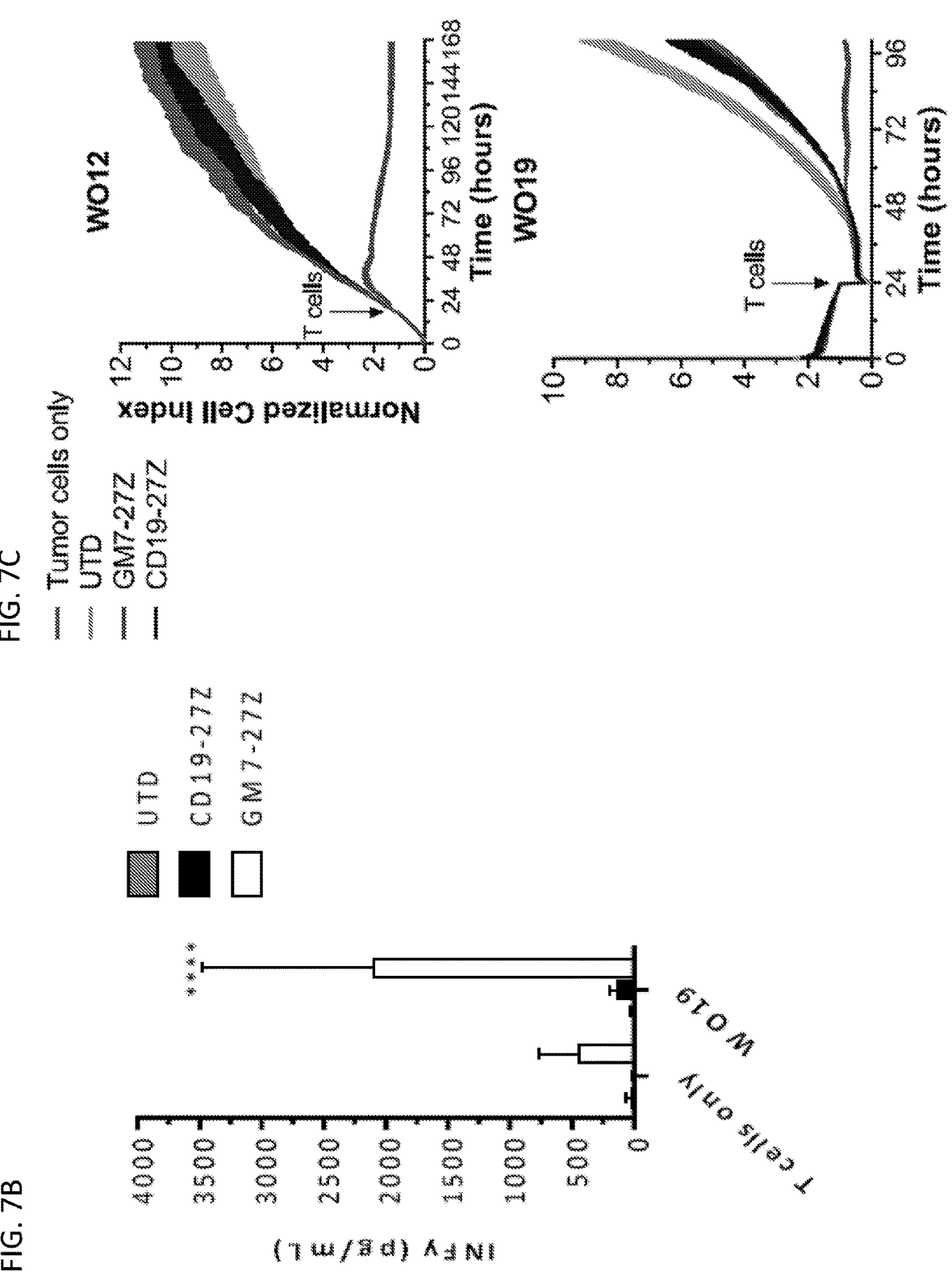

SEQUENCE LISTING

<160> NUMBER OF SEQ ID NOS: 43

<210> SEQ ID NO 1
<211> LENGTH: 1554
<212> TYPE: DNA
<213> ORGANISM: Artificial Sequence

```
<220> FEATURE:
<223> OTHER INFORMATION: MISIIR-specific CAR

<400> SEQUENCE: 1
atggccttac cagtgaccgc cttgctcctg ccgctggcct tgctgctcca cgccgccagg      60
ccgggatccg cccaggtgca gctggtgcag tctggaactg aggtgaagag gcctgggggc     120
tcagtgaaga tctcctgcag ggctactggt tacacctta gtgattatgg tatcagttgg      180
atgcgacagg cccctggaca agggcttgag tggatgggat ggatcagcgc ttacaatggt     240
aacacaaact atgcacagaa gctccagggc agagtcacca tgaccacaga cacgtccacg     300
agcacagcct acatggagct gaggagcctc agatatgacg acacggccgt atattactgt     360
gcgagagatg ggaggcgtgg ttcgggtatt tactgggtgt gtattatta caacggtatg      420 gacgtctggg gccaagggac cacggtcacc gtctcctcag gtggcggcgg ttccggaggt     480
ggtggttctg gcggtggtgg cagtcagcct gtgctgactc agccaccctc agcgtctggg     540
acccccgggc agagggtcac catctcttgt tctggaagca ggtccaacat cggaaggaat     600
accgtaaact ggtatcagca ggtcccagga atggccccca aactcctcat ctatagtaat     660
aatcagcggc cctcaggggt ccctgaccga ttctctggct ccaagtctgg cacctcagcc     720
tccctggcca tcagtgggct ccagtctgag gatgaggctg attattactg tgcagcatgg     780
gatgacagtc tgaatggtgt ggtattcggc ggagggacca agctgaccgt cctaggtcag     840
cccaaggccg cccctcggc tagcaccacg acgccagcgc cgcgaccacc aacaccggcg      900
cccaccatcg cgtcgcagcc cctgtccctg cgcccagagg cgtgccggcc agcggcgggg     960
ggcgcagtgc acacgagggg gctggacttc gcctgtgata tctacatctg ggcgcccttg    1020
gccgggactt gtggggtcct tctcctgtca ctggttatca ccctttactg ccaacgaagg    1080
aaatatagat caaacaaagg agaaagtcct gtggagcctg cagagccttg tcgttacagc    1140
tgccccaggg aggaggaggg cagcaccatc cccatccagg aggattaccg aaaaccggag    1200
cctgcctgct cccccagagt gaagttcagc aggagcgcag acgcccccgc gtaccagcag    1260
ggccagaacc agctctataa cgagctcaat ctaggacgaa gagaggagta cgatgttttg    1320
gacaagagac gtggccggga ccctgagatg ggggggaaagc cgagaaggaa gaaccctcag    1380
gaaggcctgt acaatgaact gcagaaagat aagatggcgg aggcctacag tgagattggg    1440
atgaaaggcg agcgccggag gggcaagggg cacgatggcc tttaccaggg tctcagtaca    1500
gccaccaagg acacctacga cgcccttcac atgcaggccc tgcccctcg ctaa          1554

<210> SEQ ID NO 2
<211> LENGTH: 517
<212> TYPE: PRT
<213> ORGANISM: Artificial Sequence
<220> FEATURE:
<223> OTHER INFORMATION: MISIIR-specific CAR

<400> SEQUENCE: 2

Met Ala Leu Pro Val Thr Ala Leu Leu Leu Pro Leu Ala Leu Leu Leu
1               5                   10                  15

His Ala Ala Arg Pro Gly Ser Ala Gln Val Gln Leu Val Gln Ser Gly
                20                  25                  30

Thr Glu Val Lys Arg Pro Gly Ala Ser Val Lys Ile Ser Cys Arg Ala
            35                  40                  45

Thr Gly Tyr Thr Phe Ser Asp Tyr Gly Ile Ser Trp Met Arg Gln Ala
        50                  55                  60
```

-continued

```
Pro Gly Gln Gly Leu Glu Trp Met Gly Trp Ile Ser Ala Tyr Asn Gly
65              70                  75                  80

Asn Thr Asn Tyr Ala Gln Lys Leu Gln Gly Arg Val Thr Met Thr Thr
                85                  90                  95

Asp Thr Ser Thr Ser Thr Ala Tyr Met Glu Leu Arg Ser Leu Arg Tyr
            100                 105                 110

Asp Asp Thr Ala Val Tyr Tyr Cys Ala Arg Asp Gly Arg Arg Gly Ser
            115                 120                 125

Gly Ile Tyr Trp Gly Val Tyr Tyr Asn Gly Met Asp Val Trp Gly
        130                 135                 140

Gln Gly Thr Thr Val Thr Val Ser Ser Gly Gly Gly Ser Gly Gly
145                 150                 155                 160

Gly Gly Ser Gly Gly Gly Gly Ser Gln Pro Val Leu Thr Gln Pro Pro
                165                 170                 175

Ser Ala Ser Gly Thr Pro Gly Gln Arg Val Thr Ile Ser Cys Ser Gly
            180                 185                 190

Ser Arg Ser Asn Ile Gly Arg Asn Thr Val Asn Trp Tyr Gln Gln Val
            195                 200                 205

Pro Gly Met Ala Pro Lys Leu Leu Ile Tyr Ser Asn Asn Gln Arg Pro
    210                 215                 220

Ser Gly Val Pro Asp Arg Phe Ser Gly Ser Lys Ser Gly Thr Ser Ala
225                 230                 235                 240

Ser Leu Ala Ile Ser Gly Leu Gln Ser Glu Asp Glu Ala Asp Tyr Tyr
            245                 250                 255

Cys Ala Ala Trp Asp Asp Ser Leu Asn Gly Val Val Phe Gly Gly Gly
            260                 265                 270

Thr Lys Leu Thr Val Leu Gly Gln Pro Lys Ala Ala Pro Ser Ala Ser
        275                 280                 285

Thr Thr Thr Pro Ala Pro Arg Pro Pro Thr Pro Ala Pro Thr Ile Ala
    290                 295                 300

Ser Gln Pro Leu Ser Leu Arg Pro Glu Ala Cys Arg Pro Ala Ala Gly
305                 310                 315                 320

Gly Ala Val His Thr Arg Gly Leu Asp Phe Ala Cys Asp Ile Tyr Ile
            325                 330                 335

Trp Ala Pro Leu Ala Gly Thr Cys Gly Val Leu Leu Leu Ser Leu Val
            340                 345                 350

Ile Thr Leu Tyr Cys Gln Arg Arg Lys Tyr Arg Ser Asn Lys Gly Glu
        355                 360                 365

Ser Pro Val Glu Pro Ala Glu Pro Cys Arg Tyr Ser Cys Pro Arg Glu
        370                 375                 380

Glu Glu Gly Ser Thr Ile Pro Ile Gln Glu Asp Tyr Arg Lys Pro Glu
385                 390                 395                 400

Pro Ala Cys Ser Pro Arg Val Lys Phe Ser Arg Ser Ala Asp Ala Pro
            405                 410                 415

Ala Tyr Gln Gln Gly Gln Asn Gln Leu Tyr Asn Glu Leu Asn Leu Gly
        420                 425                 430

Arg Arg Glu Glu Tyr Asp Val Leu Asp Lys Arg Arg Gly Arg Asp Pro
        435                 440                 445

Glu Met Gly Gly Lys Pro Arg Arg Lys Asn Pro Gln Glu Gly Leu Tyr
    450                 455                 460

Asn Glu Leu Gln Lys Asp Lys Met Ala Glu Ala Tyr Ser Glu Ile Gly
465                 470                 475                 480

Met Lys Gly Glu Arg Arg Arg Gly Lys Gly His Asp Gly Leu Tyr Gln
```

```
                  485                    490                    495
Gly Leu Ser Thr Ala Thr Lys Asp Thr Tyr Asp Ala Leu His Met Gln
            500                    505                    510

Ala Leu Pro Pro Arg
        515

<210> SEQ ID NO 3
<211> LENGTH: 5
<212> TYPE: PRT
<213> ORGANISM: Artificial Sequence
<220> FEATURE:
<223> OTHER INFORMATION: Linker
<220> FEATURE:
<221> NAME/KEY: Repeat
<222> LOCATION: (1)..(5)
<223> OTHER INFORMATION: Repeat n times, where n represents an integer
      of at least 1

<400> SEQUENCE: 3

Gly Ser Gly Gly Ser
1               5

<210> SEQ ID NO 4
<211> LENGTH: 4
<212> TYPE: PRT
<213> ORGANISM: Artificial Sequence
<220> FEATURE:
<223> OTHER INFORMATION: Linker
<220> FEATURE:
<221> NAME/KEY: Repeat
<222> LOCATION: (1)..(4)
<223> OTHER INFORMATION: Repeat n times, where n represents an integer
      of at least 1

<400> SEQUENCE: 4

Gly Gly Gly Ser
1

<210> SEQ ID NO 5
<211> LENGTH: 5
<212> TYPE: PRT
<213> ORGANISM: Artificial Sequence
<220> FEATURE:
<223> OTHER INFORMATION: Linker
<220> FEATURE:
<221> NAME/KEY: Repeat
<222> LOCATION: (1)..(5)
<223> OTHER INFORMATION: Repeat n times, where n represents an integer
      of at least one

<400> SEQUENCE: 5

Gly Gly Gly Gly Ser
1               5

<210> SEQ ID NO 6
<211> LENGTH: 4
<212> TYPE: PRT
<213> ORGANISM: Artificial Sequence
<220> FEATURE:
<223> OTHER INFORMATION: Linker

<400> SEQUENCE: 6

Gly Gly Ser Gly
1

<210> SEQ ID NO 7
<211> LENGTH: 5
<212> TYPE: PRT
```

```
<213> ORGANISM: Artificial Sequence
<220> FEATURE:
<223> OTHER INFORMATION: Linker

<400> SEQUENCE: 7

Gly Gly Ser Gly Gly
1               5

<210> SEQ ID NO 8
<211> LENGTH: 5
<212> TYPE: PRT
<213> ORGANISM: Artificial Sequence
<220> FEATURE:
<223> OTHER INFORMATION: Linker

<400> SEQUENCE: 8

Gly Ser Gly Ser Gly
1               5

<210> SEQ ID NO 9
<211> LENGTH: 5
<212> TYPE: PRT
<213> ORGANISM: Artificial Sequence
<220> FEATURE:
<223> OTHER INFORMATION: Linker

<400> SEQUENCE: 9

Gly Ser Gly Gly Gly
1               5

<210> SEQ ID NO 10
<211> LENGTH: 5
<212> TYPE: PRT
<213> ORGANISM: Artificial Sequence
<220> FEATURE:
<223> OTHER INFORMATION: Linker

<400> SEQUENCE: 10

Gly Gly Gly Ser Gly
1               5

<210> SEQ ID NO 11
<211> LENGTH: 5
<212> TYPE: PRT
<213> ORGANISM: Artificial Sequence
<220> FEATURE:
<223> OTHER INFORMATION: Linker

<400> SEQUENCE: 11

Gly Ser Ser Ser Gly
1               5

<210> SEQ ID NO 12
<211> LENGTH: 5
<212> TYPE: PRT
<213> ORGANISM: Artificial Sequence
<220> FEATURE:
<223> OTHER INFORMATION: Linker

<400> SEQUENCE: 12

Gly Gly Gly Gly Ser
1               5

<210> SEQ ID NO 13
<211> LENGTH: 15
<212> TYPE: PRT
<213> ORGANISM: Artificial Sequence
```

-continued

<220> FEATURE:
<223> OTHER INFORMATION: Linker
<400> SEQUENCE: 13

Gly Gly Gly Gly Ser Gly Gly Gly Gly Ser Gly Gly Gly Gly Ser
1               5                   10                  15

<210> SEQ ID NO 14
<211> LENGTH: 45
<212> TYPE: DNA
<213> ORGANISM: Artificial Sequence
<220> FEATURE:
<223> OTHER INFORMATION: Linker
<400> SEQUENCE: 14
ggtggcggtg gctcgggcgg tggtgggtcg ggtggcggcg gatct                     45

<210> SEQ ID NO 15
<211> LENGTH: 263
<212> TYPE: PRT
<213> ORGANISM: Artificial Sequence
<220> FEATURE:
<223> OTHER INFORMATION: MISIIR scFv
<400> SEQUENCE: 15

Ala Gln Val Gln Leu Val Gln Ser Gly Thr Glu Val Lys Arg Pro Gly
1               5                   10                  15

Ala Ser Val Lys Ile Ser Cys Arg Ala Thr Gly Tyr Thr Phe Ser Asp
            20                  25                  30

Tyr Gly Ile Ser Trp Met Arg Gln Ala Pro Gly Gln Gly Leu Glu Trp
        35                  40                  45

Met Gly Trp Ile Ser Ala Tyr Asn Gly Asn Thr Asn Tyr Ala Gln Lys
    50                  55                  60

Leu Gln Gly Arg Val Thr Met Thr Thr Asp Thr Ser Thr Ser Thr Ala
65                  70                  75                  80

Tyr Met Glu Leu Arg Ser Leu Arg Tyr Asp Asp Thr Ala Val Tyr Tyr
                85                  90                  95

Cys Ala Arg Asp Gly Arg Arg Gly Ser Gly Ile Tyr Trp Gly Val Tyr
                100                 105                 110

Tyr Tyr Asn Gly Met Asp Val Trp Gly Gln Gly Thr Thr Val Thr Val
            115                 120                 125

Ser Ser Gly Gly Gly Gly Ser Gly Gly Gly Gly Ser Gly Gly Gly Gly
    130                 135                 140

Ser Gln Pro Val Leu Thr Gln Pro Ser Ala Ser Gly Thr Pro Gly
145                 150                 155                 160

Gln Arg Val Thr Ile Ser Cys Ser Gly Ser Arg Ser Asn Ile Gly Arg
                165                 170                 175

Asn Thr Val Asn Trp Tyr Gln Gln Val Pro Gly Met Ala Pro Lys Leu
            180                 185                 190

Leu Ile Tyr Ser Asn Asn Gln Arg Pro Ser Gly Val Pro Asp Arg Phe
        195                 200                 205

Ser Gly Ser Lys Ser Gly Thr Ser Ala Ser Leu Ala Ile Ser Gly Leu
    210                 215                 220

Gln Ser Glu Asp Glu Ala Asp Tyr Tyr Cys Ala Ala Trp Asp Asp Ser
225                 230                 235                 240

Leu Asn Gly Val Val Phe Gly Gly Gly Thr Lys Leu Thr Val Leu Gly
                245                 250                 255

Gln Pro Lys Ala Ala Pro Ser

260

<210> SEQ ID NO 16
<211> LENGTH: 789
<212> TYPE: DNA
<213> ORGANISM: Artificial Sequence
<220> FEATURE:
<223> OTHER INFORMATION: MISIIR scFv

<400> SEQUENCE: 16

```
gcccaggtgc agctggtgca gtctggaact gaggtgaaga ggcctggggc ctcagtgaag      60
atctcctgca gggctactgg ttacaccttt agtgattatg gtatcagttg gatgcgacag     120
gcccctggac aagggcttga gtggatggga tggatcagcg cttacaatgg taacacaaac     180
tatgcacaga gctccaggg cagagtcacc atgaccacag acacgtccac gagcacagcc     240
tacatggagc tgaggagcct cagatatgac gacacggccg tatattactg tgcgagagat     300
gggaggcgtg gttcgggtat ttactggggt gtgtattatt acaacggtat ggacgtctgg     360
ggccaaggga ccacggtcac cgtctcctca ggtggcggcg gttccggagg tggtggttct     420
ggcggtggtg gcagtcagcc tgtgctgact cagccaccct cagcgtctgg accccccggg     480
cagagggtca ccatctcttg ttctggaagc aggtccaaca tcggaaggaa taccgtaaac     540
tggtatcagc aggtcccagg aatggccccc aaactcctca tctatagtaa taatcagcgg     600
ccctcagggg tccctgaccg attctctggc tccaagtctg gcacctcagc ctccctggcc     660
atcagtgggc tccagtctga ggatgaggct gattattact gtgcagcatg ggatgacagt     720
ctgaatggtg tggtattcgg cggagggacc aagctgaccg tcctaggtca gcccaaggcc     780
gccccctcg                                                              789
```

<210> SEQ ID NO 17
<211> LENGTH: 24
<212> TYPE: PRT
<213> ORGANISM: Artificial Sequence
<220> FEATURE:
<223> OTHER INFORMATION: CD8a transmembrane domain

<400> SEQUENCE: 17

```
Ile Tyr Ile Trp Ala Pro Leu Ala Gly Thr Cys Gly Val Leu Leu Leu
1               5                   10                  15

Ser Leu Val Ile Thr Leu Tyr Cys
            20
```

<210> SEQ ID NO 18
<211> LENGTH: 72
<212> TYPE: DNA
<213> ORGANISM: Artificial Sequence
<220> FEATURE:
<223> OTHER INFORMATION: CD8a transmembrane domain

<400> SEQUENCE: 18

```
atctacatct gggcgccctt ggccgggact tgtggggtcc ttctcctgtc actggttatc      60
accctttact gc                                                          72
```

<210> SEQ ID NO 19
<211> LENGTH: 48
<212> TYPE: PRT
<213> ORGANISM: Artificial Sequence
<220> FEATURE:
<223> OTHER INFORMATION: CD27 intracellular domain

<400> SEQUENCE: 19

```
Gln Arg Arg Lys Tyr Arg Ser Asn Lys Gly Glu Ser Pro Val Glu Pro
1               5                   10                  15

Ala Glu Pro Cys Arg Tyr Ser Cys Pro Arg Glu Glu Glu Gly Ser Thr
                20                  25                  30

Ile Pro Ile Gln Glu Asp Tyr Arg Lys Pro Glu Pro Ala Cys Ser Pro
        35                  40                  45
```

```
<210> SEQ ID NO 20
<211> LENGTH: 144
<212> TYPE: DNA
<213> ORGANISM: Artificial Sequence
<220> FEATURE:
<223> OTHER INFORMATION: CD27 intracellular domain

<400> SEQUENCE: 20
caacgaagga aatatagatc aaacaaagga gaaagtcctg tggagcctgc agagccttgt       60
cgttacagct gccccaggga ggaggagggc agcaccatcc ccatccagga ggattaccga      120
aaaccggagc ctgcctgctc cccc                                             144
```

```
<210> SEQ ID NO 21
<211> LENGTH: 112
<212> TYPE: PRT
<213> ORGANISM: Artificial Sequence
<220> FEATURE:
<223> OTHER INFORMATION: CD3 zeta intracellular domain

<400> SEQUENCE: 21

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
                20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110
```

```
<210> SEQ ID NO 22
<211> LENGTH: 339
<212> TYPE: DNA
<213> ORGANISM: Artificial Sequence
<220> FEATURE:
<223> OTHER INFORMATION: CD3 zeta intracellular domain

<400> SEQUENCE: 22
agagtgaagt tcagcaggag cgcagacgcc cccgcgtacc agcagggcca gaaccagctc       60
tataacgagc tcaatctagg acgaagagag gagtacgatg ttttggacaa gagacgtggc      120
cgggaccctg agatgggggg aaagccgaga aggaagaacc ctcaggaagg cctgtacaat      180
gaactgcaga aagataagat ggcggaggcc tacagtgaga ttgggatgaa aggcgagcgc      240
cggaggggca aggggcacga tggcctttac caggtctca gtacagccac caaggacacc      300
tacgacgccc ttcacatgca ggccctgccc cctcgctaa                             339
```

-continued

```
<210> SEQ ID NO 23
<211> LENGTH: 5
<212> TYPE: PRT
<213> ORGANISM: Artificial Sequence
<220> FEATURE:
<223> OTHER INFORMATION: Hinge

<400> SEQUENCE: 23

Asp Lys Thr His Thr
1               5

<210> SEQ ID NO 24
<211> LENGTH: 4
<212> TYPE: PRT
<213> ORGANISM: Artificial Sequence
<220> FEATURE:
<223> OTHER INFORMATION: Hinge

<400> SEQUENCE: 24

Cys Pro Pro Cys
1

<210> SEQ ID NO 25
<211> LENGTH: 15
<212> TYPE: PRT
<213> ORGANISM: Artificial Sequence
<220> FEATURE:
<223> OTHER INFORMATION: Hinge

<400> SEQUENCE: 25

Cys Pro Glu Pro Lys Ser Cys Asp Thr Pro Pro Pro Cys Pro Arg
1               5                   10                  15

<210> SEQ ID NO 26
<211> LENGTH: 12
<212> TYPE: PRT
<213> ORGANISM: Artificial Sequence
<220> FEATURE:
<223> OTHER INFORMATION: Hinge

<400> SEQUENCE: 26

Glu Leu Lys Thr Pro Leu Gly Asp Thr Thr His Thr
1               5                   10

<210> SEQ ID NO 27
<211> LENGTH: 10
<212> TYPE: PRT
<213> ORGANISM: Artificial Sequence
<220> FEATURE:
<223> OTHER INFORMATION: Hinge

<400> SEQUENCE: 27

Lys Ser Cys Asp Lys Thr His Thr Cys Pro
1               5                   10

<210> SEQ ID NO 28
<211> LENGTH: 7
<212> TYPE: PRT
<213> ORGANISM: Artificial Sequence
<220> FEATURE:
<223> OTHER INFORMATION: Hinge

<400> SEQUENCE: 28

Lys Cys Cys Val Asp Cys Pro
1               5
```

```
<210> SEQ ID NO 29
<211> LENGTH: 7
<212> TYPE: PRT
<213> ORGANISM: Artificial Sequence
<220> FEATURE:
<223> OTHER INFORMATION: Hinge

<400> SEQUENCE: 29

Lys Tyr Gly Pro Pro Cys Pro
1               5

<210> SEQ ID NO 30
<211> LENGTH: 15
<212> TYPE: PRT
<213> ORGANISM: Artificial Sequence
<220> FEATURE:
<223> OTHER INFORMATION: Hinge

<400> SEQUENCE: 30

Glu Pro Lys Ser Cys Asp Lys Thr His Thr Cys Pro Pro Cys Pro
1               5               10              15

<210> SEQ ID NO 31
<211> LENGTH: 12
<212> TYPE: PRT
<213> ORGANISM: Artificial Sequence
<220> FEATURE:
<223> OTHER INFORMATION: Hinge

<400> SEQUENCE: 31

Glu Arg Lys Cys Cys Val Glu Cys Pro Pro Cys Pro
1               5               10

<210> SEQ ID NO 32
<211> LENGTH: 17
<212> TYPE: PRT
<213> ORGANISM: Artificial Sequence
<220> FEATURE:
<223> OTHER INFORMATION: Hinge

<400> SEQUENCE: 32

Glu Leu Lys Thr Pro Leu Gly Asp Thr Thr His Thr Cys Pro Arg Cys
1               5               10              15

Pro

<210> SEQ ID NO 33
<211> LENGTH: 12
<212> TYPE: PRT
<213> ORGANISM: Artificial Sequence
<220> FEATURE:
<223> OTHER INFORMATION: Hinge

<400> SEQUENCE: 33

Ser Pro Asn Met Val Pro His Ala His His Ala Gln
1               5               10

<210> SEQ ID NO 34
<211> LENGTH: 15
<212> TYPE: PRT
<213> ORGANISM: Artificial Sequence
<220> FEATURE:
<223> OTHER INFORMATION: Hinge

<400> SEQUENCE: 34

Glu Pro Lys Ser Cys Asp Lys Thr Tyr Thr Cys Pro Pro Cys Pro
1               5               10              15
```

-continued

```
<210> SEQ ID NO 35
<211> LENGTH: 38
<212> TYPE: DNA
<213> ORGANISM: Artificial Sequence
<220> FEATURE:
<223> OTHER INFORMATION: Primer

<400> SEQUENCE: 35
tatggatccg cccaggtgca gctggtgcag tctggaac                               38

<210> SEQ ID NO 36
<211> LENGTH: 36
<212> TYPE: DNA
<213> ORGANISM: Artificial Sequence
<220> FEATURE:
<223> OTHER INFORMATION: Primer

<400> SEQUENCE: 36
tatgctagcc gagggggcgg ccttgggctg acctag                                36

<210> SEQ ID NO 37
<211> LENGTH: 36
<212> TYPE: DNA
<213> ORGANISM: Artificial Sequence
<220> FEATURE:
<223> OTHER INFORMATION: Primer

<400> SEQUENCE: 37
tatggatccg cccaggtgca gctggtggag tctggg                                36

<210> SEQ ID NO 38
<211> LENGTH: 38
<212> TYPE: DNA
<213> ORGANISM: Artificial Sequence
<220> FEATURE:
<223> OTHER INFORMATION: Primer

<400> SEQUENCE: 38
tatgctagca cgtttgatct ccagcttggt ccctccgc                               38

<210> SEQ ID NO 39
<211> LENGTH: 36
<212> TYPE: DNA
<213> ORGANISM: Artificial Sequence
<220> FEATURE:
<223> OTHER INFORMATION: Primer

<400> SEQUENCE: 39
tattgatcag ccgaggtgca gctggtgcag tctggg                                36

<210> SEQ ID NO 40
<211> LENGTH: 36
<212> TYPE: DNA
<213> ORGANISM: Artificial Sequence
<220> FEATURE:
<223> OTHER INFORMATION: Primer

<400> SEQUENCE: 40
tatgctagcc gagtgggcag ccttgggctg accgag                                36

<210> SEQ ID NO 41
<211> LENGTH: 36
<212> TYPE: DNA
<213> ORGANISM: Artificial Sequence
<220> FEATURE:
<223> OTHER INFORMATION: Primer
```

```
<400> SEQUENCE: 41
tatggatccg ccgaggtgca gctggtggag tctggg                              36

<210> SEQ ID NO 42
<211> LENGTH: 37
<212> TYPE: DNA
<213> ORGANISM: Artificial Sequence
<220> FEATURE:
<223> OTHER INFORMATION: Primer

<400> SEQUENCE: 42
tatgctagcc gaggggggcag ccttgggctg acctagg                            37

<210> SEQ ID NO 43
<211> LENGTH: 8
<212> TYPE: PRT
<213> ORGANISM: Artificial Sequence
<220> FEATURE:
<223> OTHER INFORMATION: Epitiope tag

<400> SEQUENCE: 43

Asp Tyr Lys Asp Asp Asp Asp Lys
1               5
```

MÜLLERIAN INHIBITING SUBSTANCE TYPE 2 RECEPTOR (MISIIR)-SPECIFIC CAR T CELLS FOR THE TREATMENT OF OVARIAN CANCER AND OTHER GYNECOLOGIC MALIGNANCIES

CROSS-REFERENCE TO RELATED APPLICATIONS

The present application is a 35 U.S.C. § 371 national phase application from, and claims priority to, International Application No. PCT/US2020/028073, filed Apr. 14, 2020, which claims priority under 35 U.S.C. § 119 (e) to U.S. Provisional Application No. 62/834,104 filed Apr. 15, 2019, all of which are incorporated herein by reference in their entireties.

BACKGROUND OF THE INVENTION

Ovarian cancer (OC) ranks 5$^{th}$ among cancer-related deaths in women and is the most lethal of all gynecologic malignancies, with an overall 5-year survival rate of 46%. There has been recent success with the FDA approved Chimeric Antigen Receptor (CAR) T cell therapy targeting CD19 for the treatment of hematologic malignancies. Despite its promise, effective CAR T cell therapy for OC has not yet been achieved. One of the challenges that may contribute to this lack of success is the appropriate selection of a target antigen that is homogeneously and highly expressed in malignant cells while absent in normal cells, which is necessary in order to ensure an efficacious and safe treatment.

The Müllerian inhibiting substance type 2 receptor (MISIR) is a member of the TGF-β receptor family and is involved in the regression of the primordial female reproductive tract in male embryos. This action is exerted through the interaction with a soluble ligand, Müllerian inhibiting substance (MIS) that triggers a downstream signaling cascade that induces apoptosis. In fact, MIS signaling through MISIIR has been shown to cause growth inhibition in ovarian, breast, prostate, cervical and endometrial cancer cell lines in vitro and in vivo, indicating the relevance of this pathway in cancer. In humans, MISIIR is expressed in a restricted set of reproductive tissues and is overexpressed in the majority of OCs as well as in other gynecologic tumors, making it a sound candidate target antigen.

There is a need in the art for compositions and methods for treating cancer, in particular ovarian cancer. The present invention addresses this need.

SUMMARY OF THE INVENTION

As described herein, the present invention relates to modified immune cells or precursors thereof (e.g., modified T cells) comprising a chimeric antigen receptor (CAR) having affinity for Müllerian inhibiting substance type 2 receptor (MISIIR), and methods for use thereof.

In one aspect, the present invention includes a modified immune cell or precursor cell thereof, comprising a chimeric antigen receptor (CAR). The CAR comprises an antigen binding domain having affinity for Müllerian inhibiting substance type 2 receptor (MISIIR), a transmembrane domain, and an intracellular domain. The antigen binding domain comprises the amino acid sequence set forth in SEQ ID NO: 15.

In another aspect, the invention includes a method of treating cancer in a subject in need thereof. The method comprises administering to the subject the modified immune or precursor cell of any of the aspects or embodiments of the present invention.

In another aspect, the invention includes a method of treating a disease or disorder in a subject in need thereof. The method comprises administering to the subject a modified T cell comprising a chimeric antigen receptor (CAR). The CAR comprises an antigen binding domain having affinity for Müllerian inhibiting substance type 2 receptor (MISIIR), a transmembrane domain, and an intracellular domain. The antigen binding domain comprises the amino acid sequence set forth in SEQ ID NO: 15.

In various embodiments of the above aspects or any other aspect of the invention delineated herein, the antigen binding domain is encoded by the nucleotide sequence set forth in SEQ ID NO: 16.

In certain exemplary embodiments, the CAR further comprises a hinge domain. In certain exemplary embodiments, the hinge domain selected from the group consisting of an Fc fragment of an antibody, a hinge region of an antibody, a CH2 region of an antibody, a CH3 region of an antibody, an artificial hinge domain, a hinge comprising an amino acid sequence of CD8, or any combination thereof.

In certain exemplary embodiments, the transmembrane domain is selected from the group consisting of an artificial hydrophobic sequence and transmembrane domain of a type I transmembrane protein, an alpha, beta, or zeta chain of a T cell receptor, CD28, CD3 epsilon, CD45, CD4, CD5, CD8, CD9, CD16, CD22, CD33, CD37, CD64, CD80, CD86, CD134, CD137, and CD154. In certain exemplary embodiments, the transmembrane domain comprises the amino acid sequence set forth in SEQ ID NO: 17. In certain exemplary embodiments, the transmembrane domain is encoded by the nucleotide sequence set forth in SEQ ID NO: 18.

In certain exemplary embodiments, the intracellular domain comprises at least one co-stimulatory domain selected from the group consisting of co-stimulatory domains of proteins in the TNFR superfamily, CD28, 4-1BB (CD137), OX40 (CD134), PD-1, CD7, LIGHT, CD83L, DAP10, DAP12, CD27, CD2, CD5, ICAM-1, LFA-1, Lck, TNFR-I, TNFR-II, Fas, CD30, CD40, ICOS, NKG2C, and B7-H3. In certain exemplary embodiments, the intracellular domain comprises an intracellular domain selected from the group consisting of cytoplasmic signaling domains of a human CD3 zeta chain, FcγRIII, FcsRI, a cytoplasmic tail of an Fc receptor, an immunoreceptor tyrosine-based activation motif (ITAM) bearing cytoplasmic receptors, TCR zeta, FcR gamma, FcR beta, CD3 gamma, CD3 delta, CD3 epsilon, CD5, CD22, CD79a, CD79b, and CD66d.

In certain exemplary embodiments, the intracellular domain comprises a CD27 domain. In certain exemplary embodiments, the intracellular domain comprises a CD27 domain and a CD3 zeta domain. In certain exemplary embodiments, the intracellular domain comprises the amino acid sequence set forth in SEQ ID NO: 19 and/or SEQ ID NO: 21. In certain exemplary embodiments, the intracellular domain is encoded by the nucleotide sequence set forth in SEQ ID NO: 20 and/or SEQ ID NO: 22.

In certain exemplary embodiments, the cell is an autologous cell. In certain exemplary embodiments, the cell is isolated from a human subject. In certain exemplary embodiments, the cell is a modified T cell.

In certain exemplary embodiments, the CAR comprises a CD8α hinge domain, a CD8α transmembrane domain, a CD27 intracellular domain, and a CD3 zeta intracellular domain.

In certain exemplary embodiments, the CAR comprises the amino acid sequence set forth in SEQ ID NO: 2. In certain exemplary embodiments, the CAR is encoded by the nucleotide sequence set forth in SEQ ID NO: 1.

In certain exemplary embodiments, the disease or disorder is cancer. In certain exemplary embodiments, the cancer is ovarian cancer. In certain exemplary embodiments, the cancer is selected from the group consisting of endometrial cancer, uterine sarcoma, cervical carcinoma, breast cancer, lung cancer, prostate cancer, ocular melanoma, and a MISIIR-expressing tumor.

In certain exemplary embodiments, the modified T cell is human. In certain exemplary embodiments, the modified T cell is autologous.

In certain exemplary embodiments, the subject is human.

BRIEF DESCRIPTION OF THE DRAWINGS

The foregoing and other features and advantages of the present invention will be more fully understood from the following detailed description of illustrative embodiments taken in conjunction with the accompanying drawings.

FIG. 1A is a schematic representation of MISIIR CAR constructs based on 4 different scFvs and containing CD27 and CD3ζ intracellular domains. A CD19 CAR was used as a control. FIG. 1B depicts surface expression of the various CARs on primary T cells detected by biotinylated anti-human H+L antibody followed by SA-APC staining. FIG. 1C depicts specific binding to target upon incubation with biotinylated recombinant protein followed by SA-APC. FIG. 1D depicts specific secretion of IFNγ upon culturing CAR T cells in the presence of increasing concentrations of recombinant target protein, detected by ELISA.

FIG. 2A illustrates generation of a tumor cell line engineered to express MISIIR. Expression of MISIIR in transduced cells was detected by anti-flag antibody. FIG. 2B depicts IFNγ secretion by CAR T cells after co-culture with target cells. FIG. 2C depicts results from a real-time killing assay after co-culture with target cells. FIG. 2D illustrates staining of the activation marker CD69 24 h after co-culture with target cells. FIG. 2E shows intracellular cytokine staining 5 h after co-culture with target cells. FIG. 2F shows staining of degranulation marker CD107a after 5 h of co-culture with target cells.

FIG. 3A shows expression of MISIIR in various tumor cell lines detected by staining with anti-MISIIR antibody. FIG. 3B illustrates IFNγ secretion by CAR T cells after co-culture with target cells. FIG. 3C shows data from a real-time killing assay after co-culture with target cells at 3:1 E:T ratio.

4

Figures 6A, 6B:
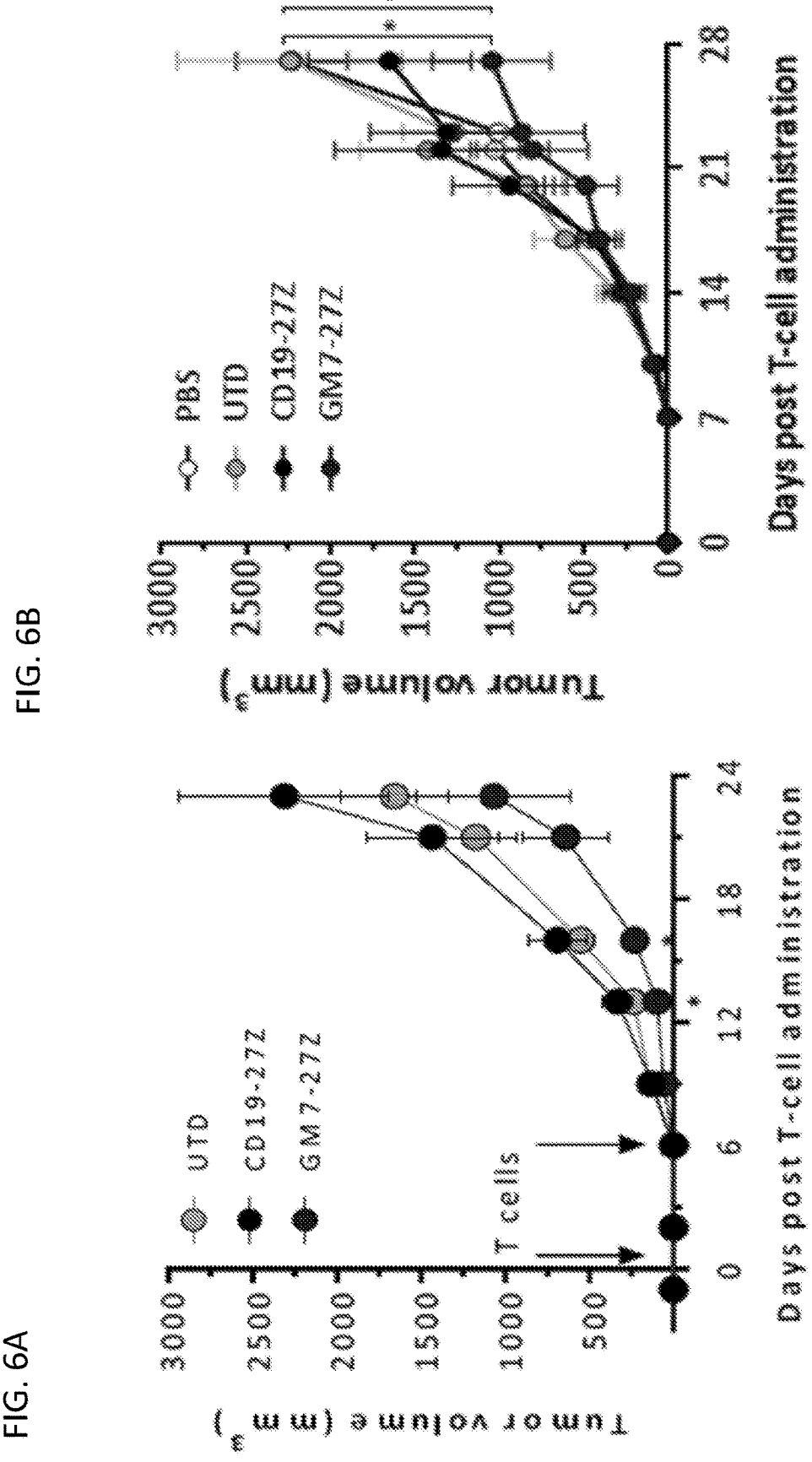

FIGS. 6A-6B depict in vivo anti-tumor efficacy data of the GM7-27Z CAR in AN3CA (FIG. 6A) and OVCAR3 (FIG. 6B) tumor models.

Figure 7A:
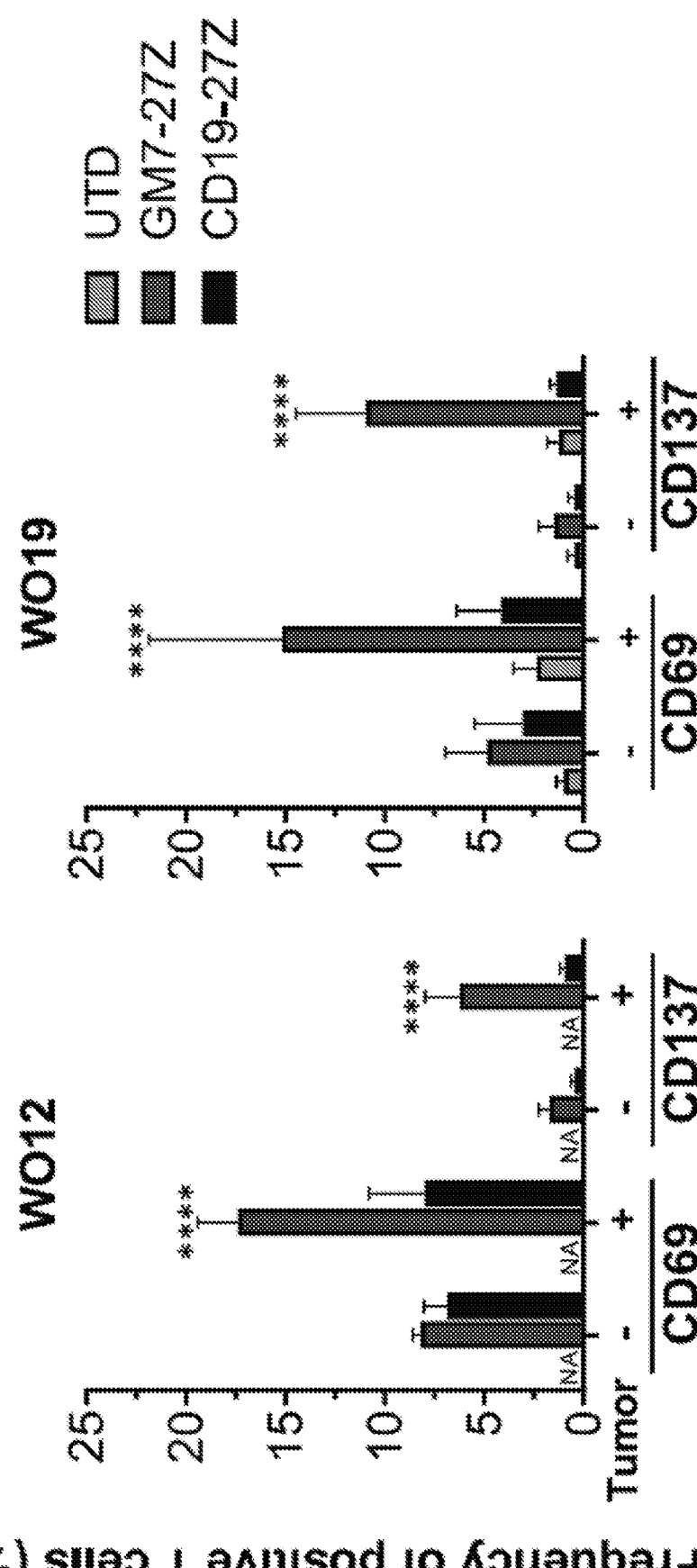

FIGS. 7A-7C depict activation markers (FIG. 7A), IFNγ secretion (FIG. 7B) and cytotoxicity (FIG. 7C) data from the GM7-27Z CAR tested in vitro with patient-derived ovarian cancer cells.

Figure 8B:
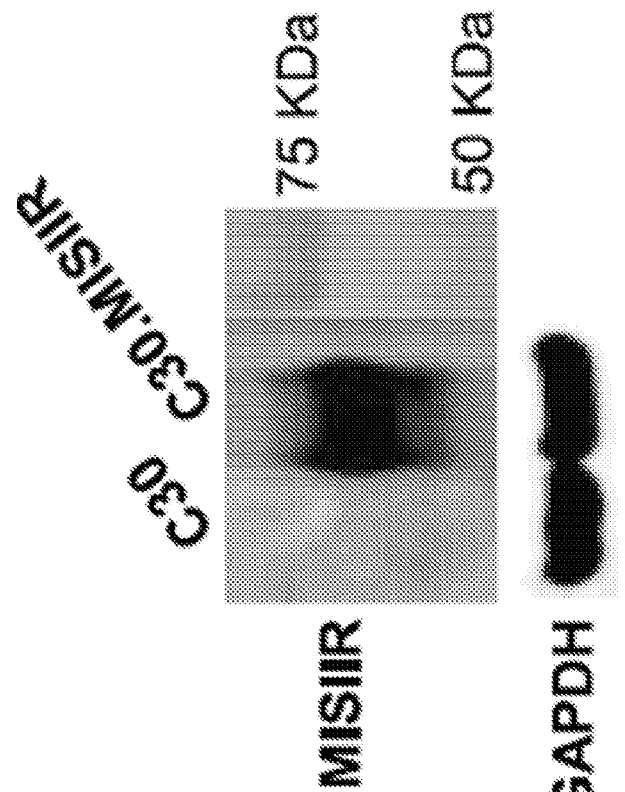
Figure 8A:
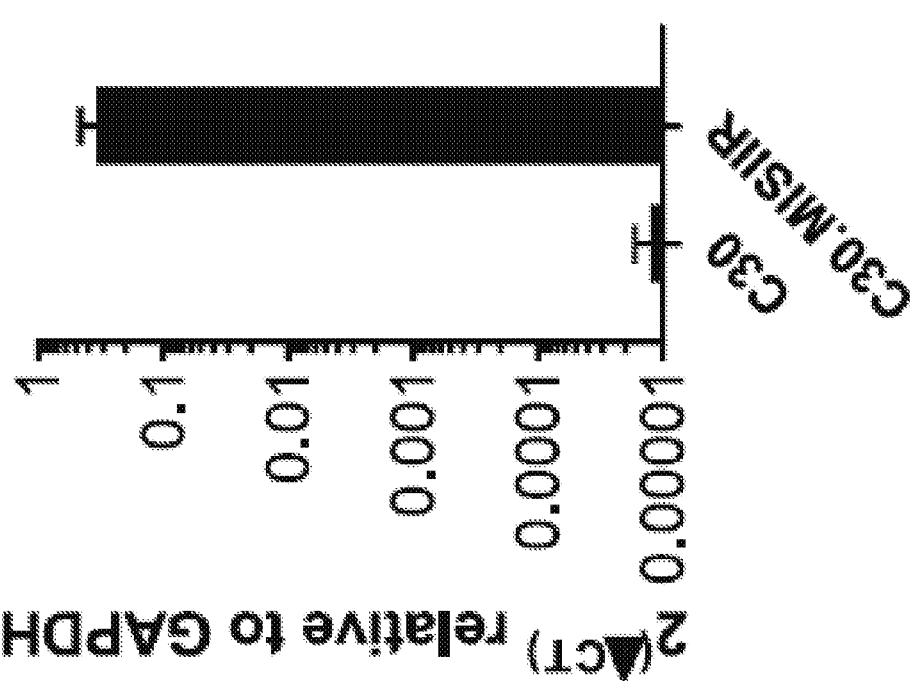
Figure 8C:
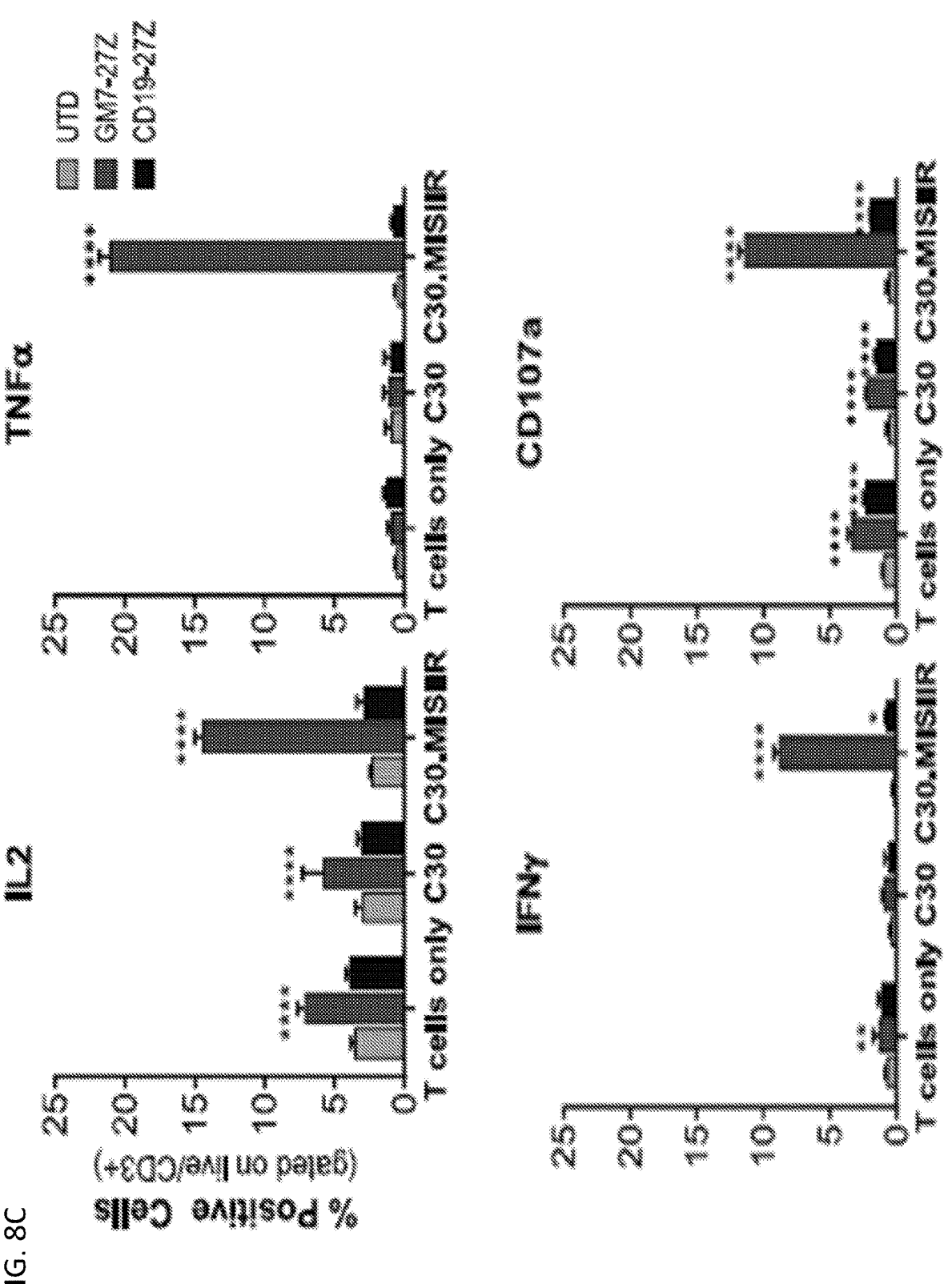

FIGS. 8A-8C depict data demonstrating GM7 CAR T cells exhibiting antigen-specific reactivity against cell surface MISIIR in vitro. MISIIR-deficient OC cell line C30 was transduced to stably overexpress human MISIIR. (FIGS. 8A-8C) MISIIR expression on engineered C30. MISIIR was detected by (FIG. 8A) quantitative real-time PCR, (FIG. 8B) western blot analysis showing a predicted ~65-kb band, and (FIG. 8C) flow cytometry using an anti-flag antibody. For functional assays, co-cultures were performed at an E:T ratio of 1:1. Mean±SD is represented for all experiments. Significance was determined by two-way ANOVA comparison and Tukey's multiple comparison test as compared to the UTD group. *p<0.05, p<0.01, **p<0.0001.

Figures 9A, 9B:
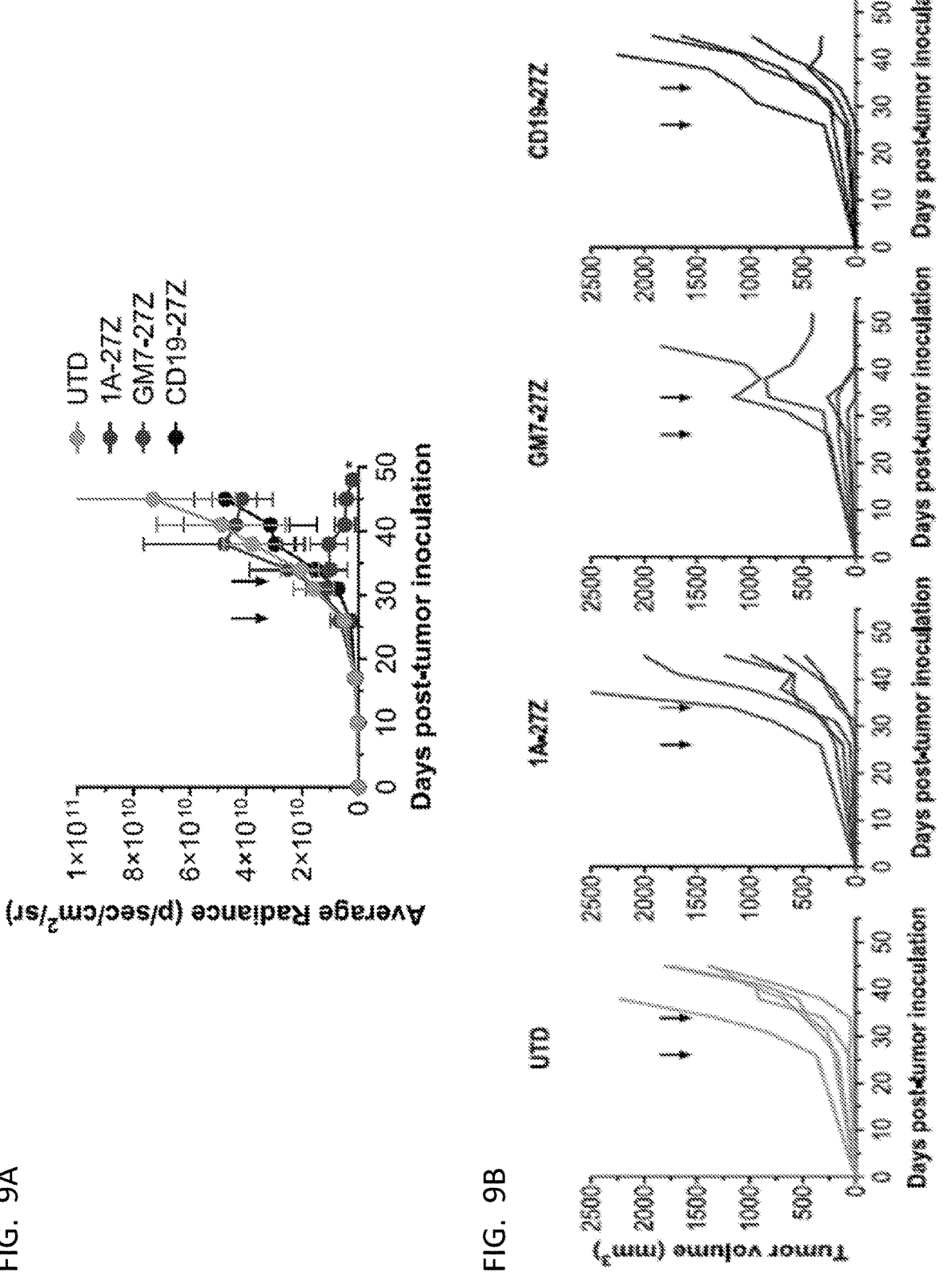
Figure 9D:
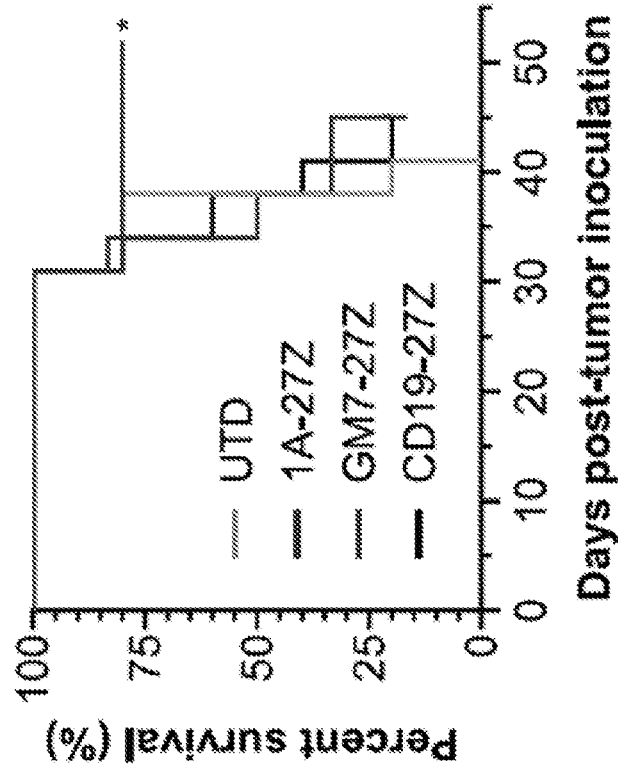
Figure 9C:
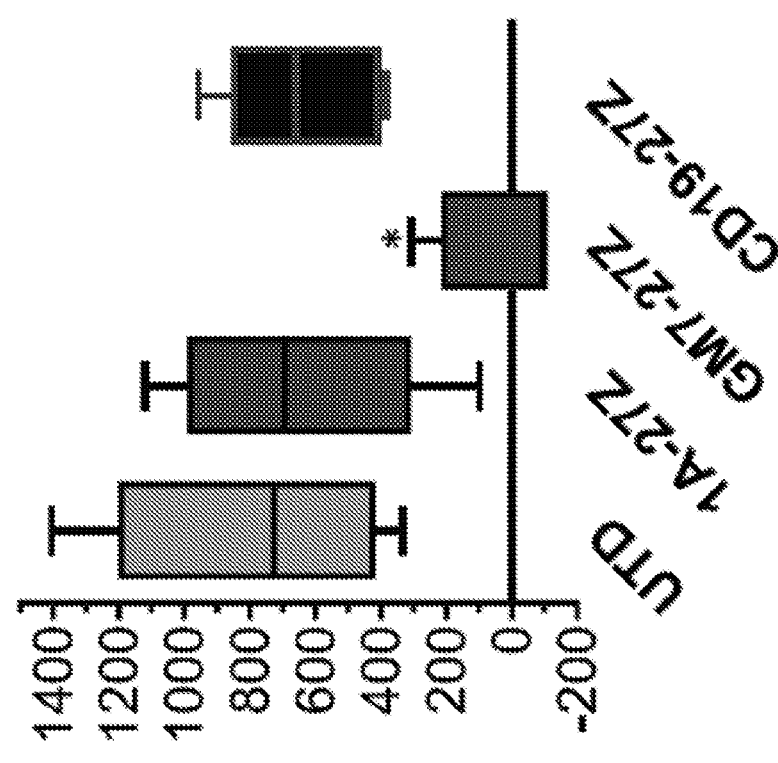

FIGS. 9A-9D depict data demonstrating GM7 CAR T cells mediating antitumor activity in vivo. C30.MISIIR GFP-fLuc cells (10×10$^6$) were inoculated into NSG mice subcutaneously. Once the tumors were established and reached a mean tumor volume of 150 mm$^3$, mice were randomized in groups and CAR+ T cells (5×10$^6$) were given intravenously on days 26 and 33 post-tumor inoculation. FIGS. 9A-9B show tumor growth was monitored by (FIG. 9A) luminescence and (FIG. 9B) caliper measurement. FIG. 9C shows a representation of the percentage of tumor growth at day 45 versus day 26. Data are represented as mean±SD of n=5-6 mice per group. Significance was determined by one-way ANOVA with Tukey's multiple comparison test as compared to the UTD group. Arrows indicate time of CAR T cell administration. FIG. 9D shows Kaplan-Meier survival curves plotted using a defined endpoint criterion of tumor volume equivalent to or greater than 1,000 mm$^3$. Significance was determined by a log-rank Mantel-Cox test as compared to the UTD group. *p<0.05.

Figure 10:
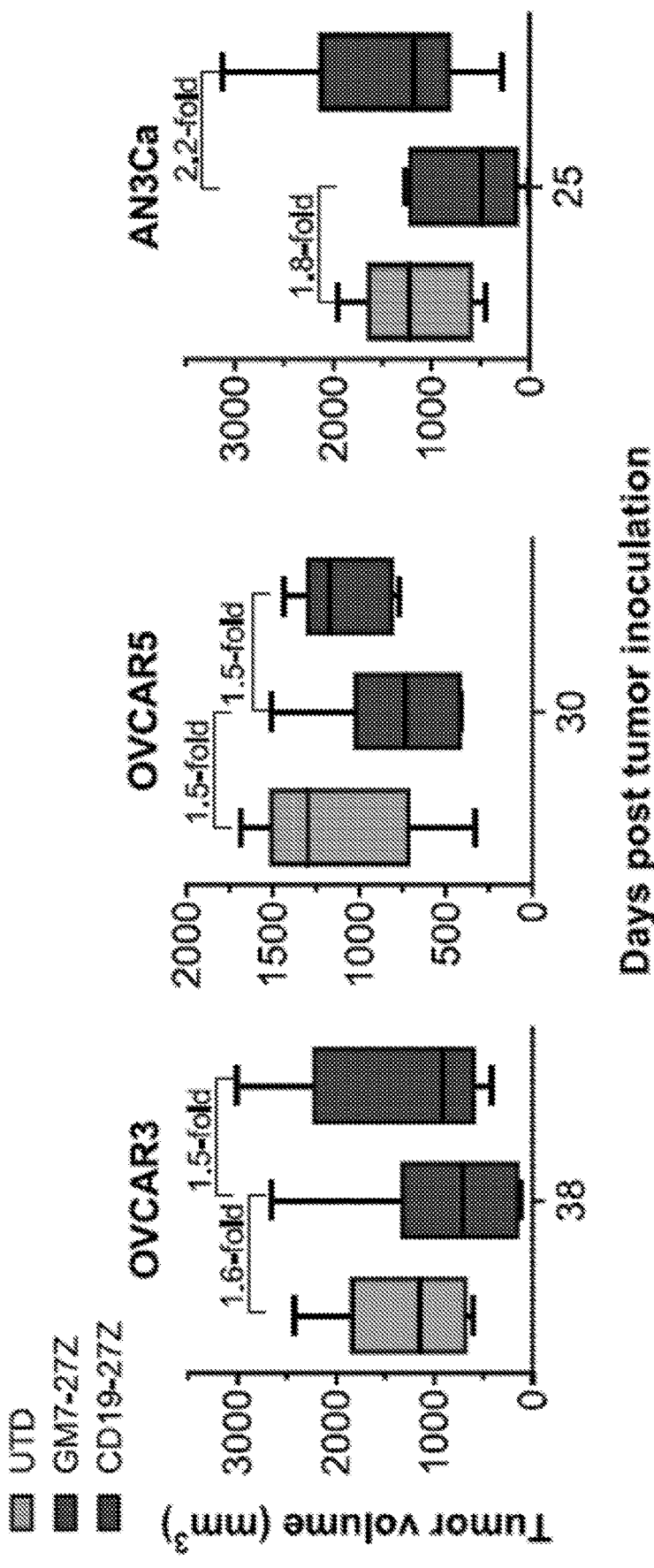

FIG. 10 depicts GM7 CAR T cells demonstrating antigen-specific reactivity against endogenous MISIIR. OVCAR3, OVCAR5, or AN3Ca GFP-fLuc cells were inoculated into NSG mice subcutaneously. Once the tumors were established, mice were randomized in groups and received two intravenous doses of CAR+ T cells (5×10$^6$) given 1 week apart. Tumor growth was monitored by caliper measurement. Means±SD of tumor volumes at the endpoint of three individual in vivo studies are represented.

Figure 11A:
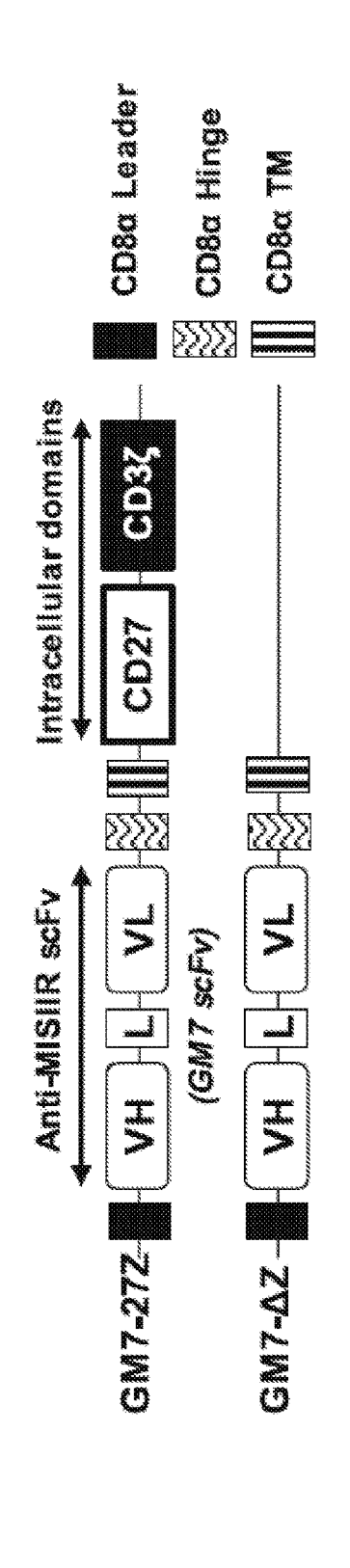
Figure 11B:
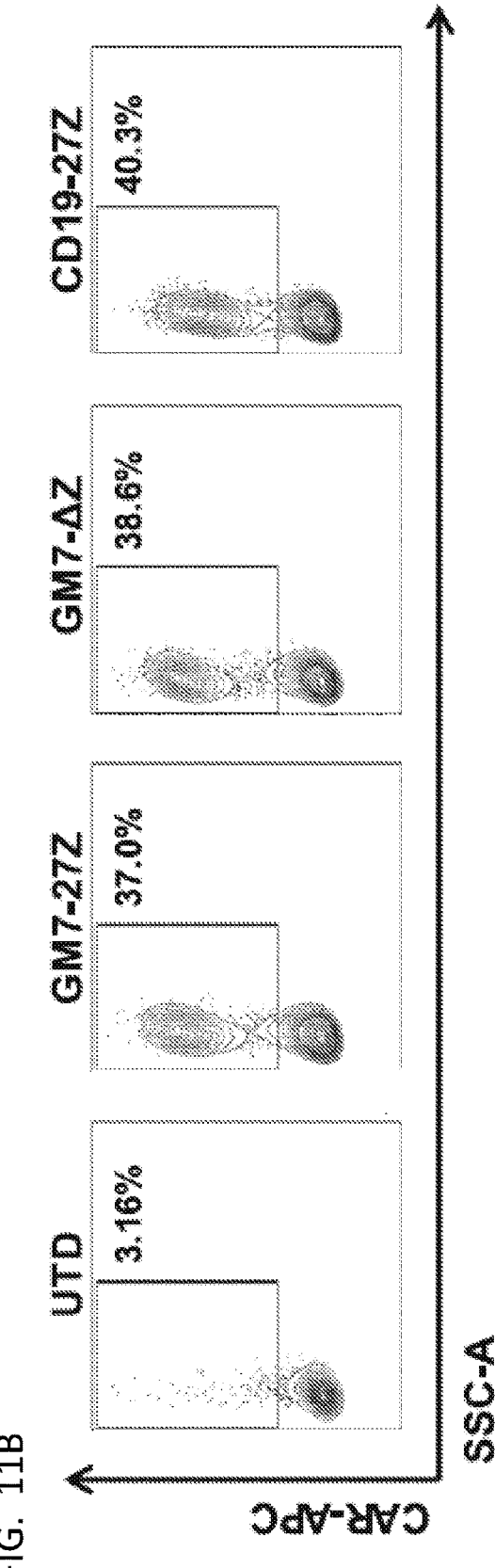
Figure 11C:
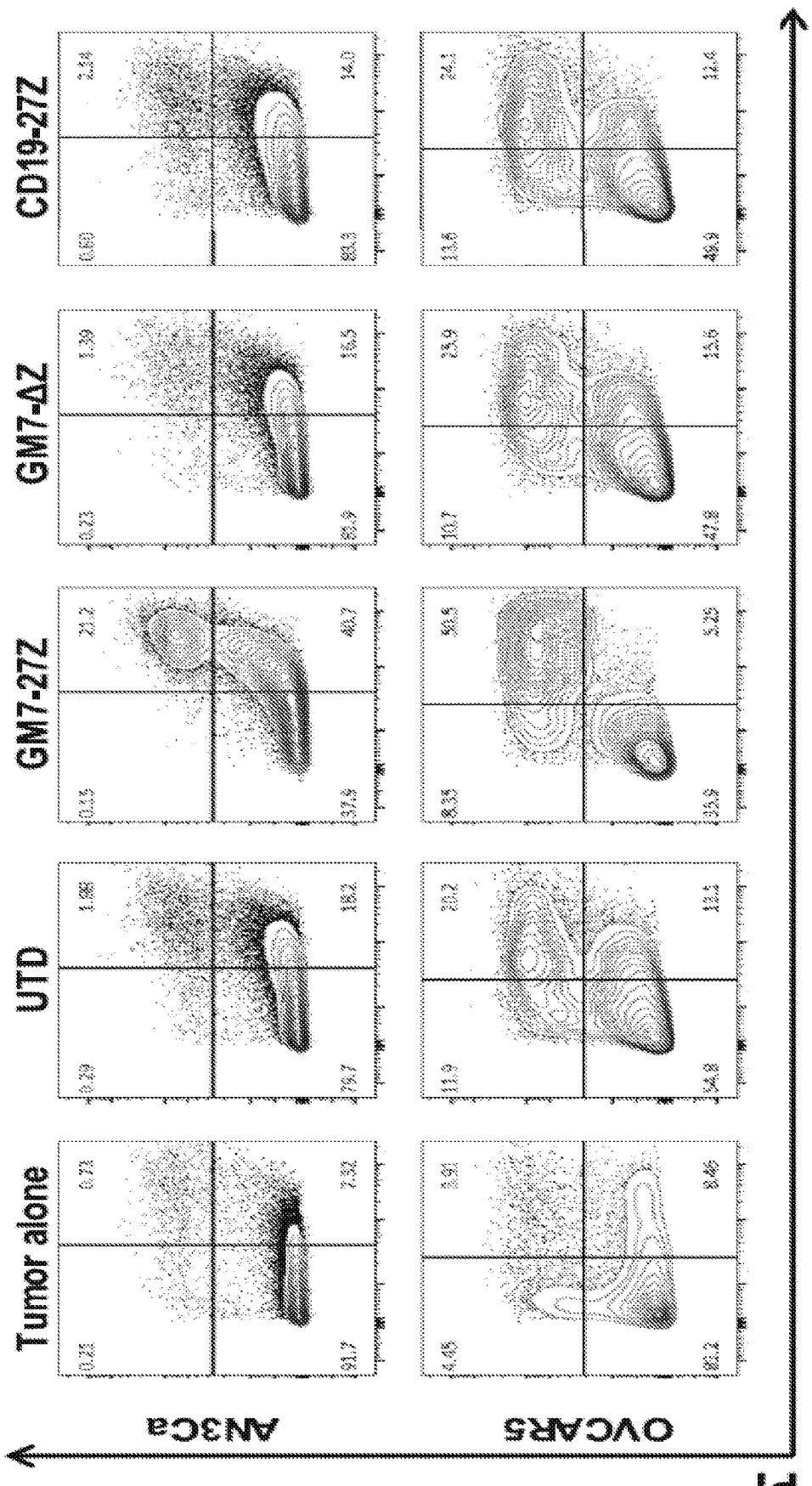
Figures 11D, 11E:
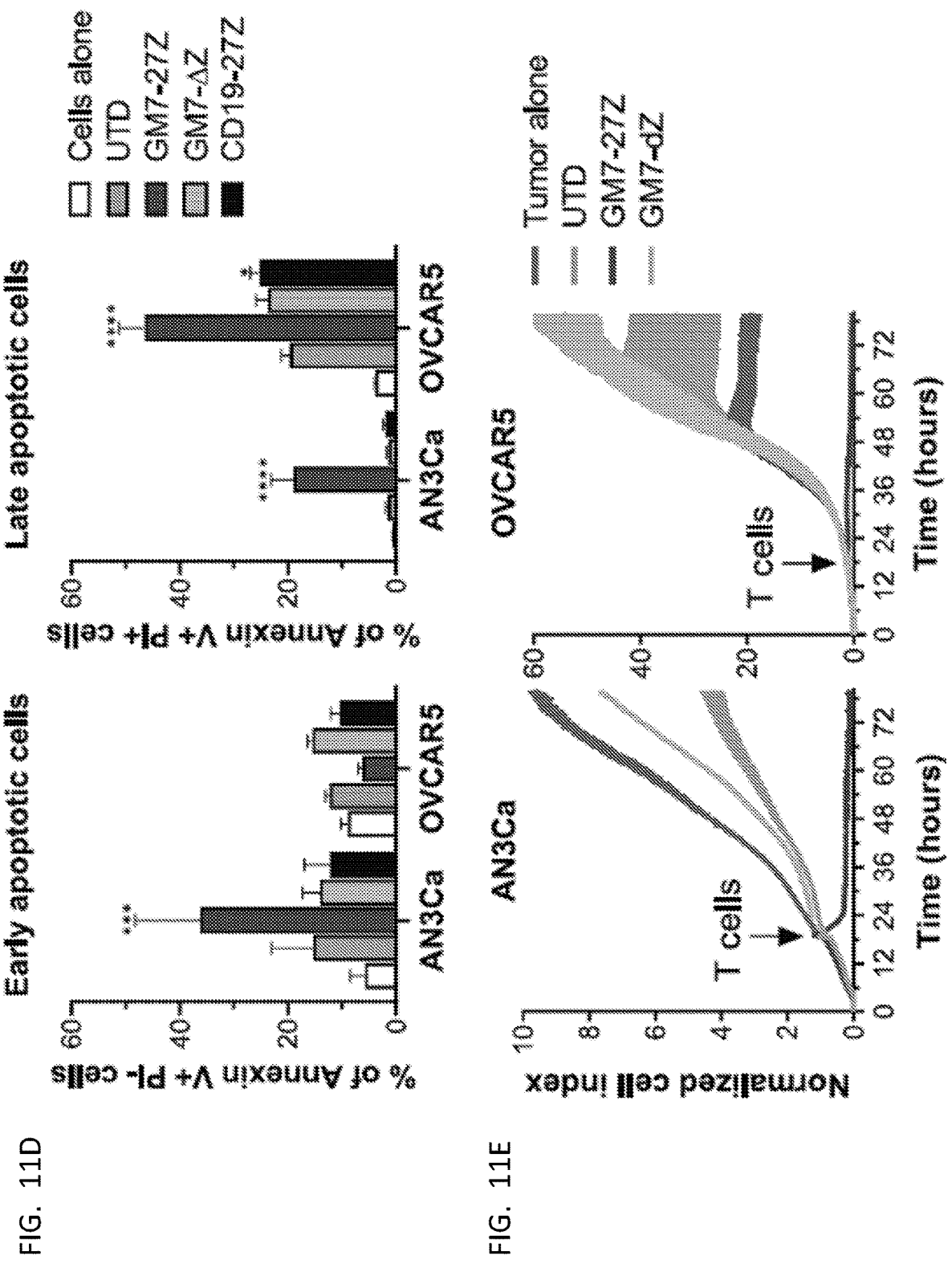

FIGS. 11A-11E depict data demonstrating that the killing mechanism of GM7 CAR T cells does not involve ligand-induced apoptosis. FIG. 11A is a schematic representation of the delta ζ (Δζ) CAR construct. FIG. 11B shows surface CAR expression in primary human T cells as detected by staining with a rabbit anti-human IgG (H+L) antibody. FIG. 11C shows representative flow plots of the staining of apoptotic markers annexin V (x axis) and PI (y axis) after 48 h of co-culture at a 3:1 E:T ratio. GFP+ tumor cells were gated prior to analysis of apoptotic markers. FIG. 11D shows frequency of early (annexin V+ PI−) and late (annexin V+ PI+) apoptotic cells. Significance was determined by two-way ANOVA and Dunnett's multiple comparison test as compared to the UTD group. *p<0.05, ****p<0.0001. FIG. 11E shows data from real-time cytotoxicity assays established at a 3:1 E:T ratio. Data are represented as mean±SD.

Figure 12:
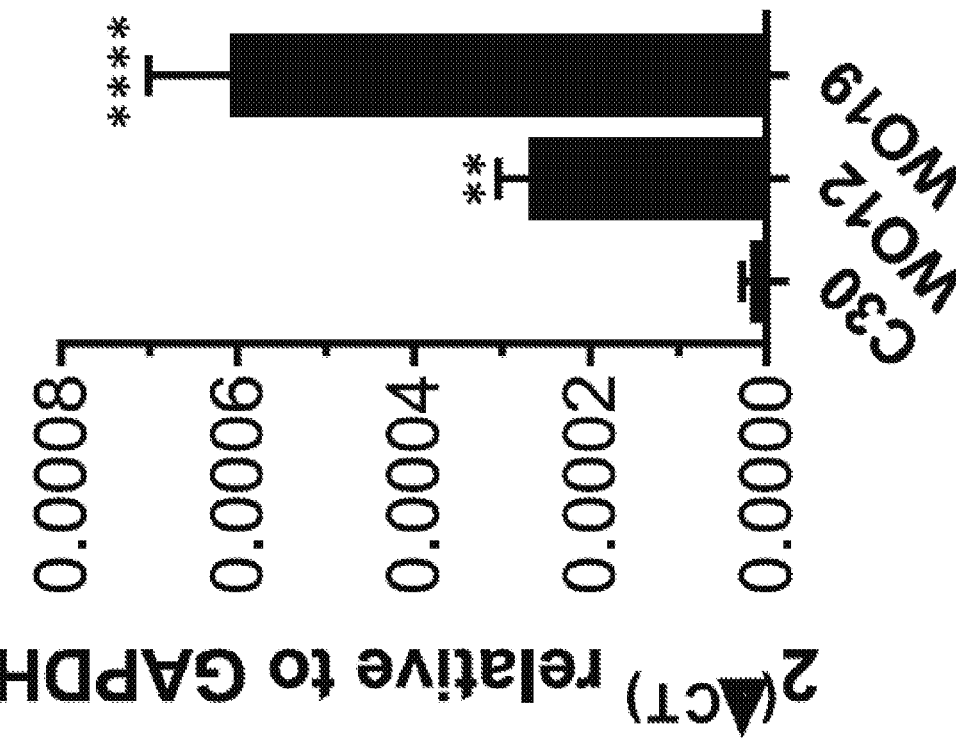

FIG. 12 depicts data demonstrating GM7 CAR T cells show reactivity in patient-derived tumor specimens. MISIIR expression in patient-derived tumors as detected by quantitative real-time PCR. Significance was determined by one-way ANOVA comparison and Dunnett's multiple comparison test. p<0.01, **p<0.0001. WO12 or WO19 cell cultures were co-cultured for 24 h with T cells at a 1:1 E:T ratio.

Figures 13A, 13B:
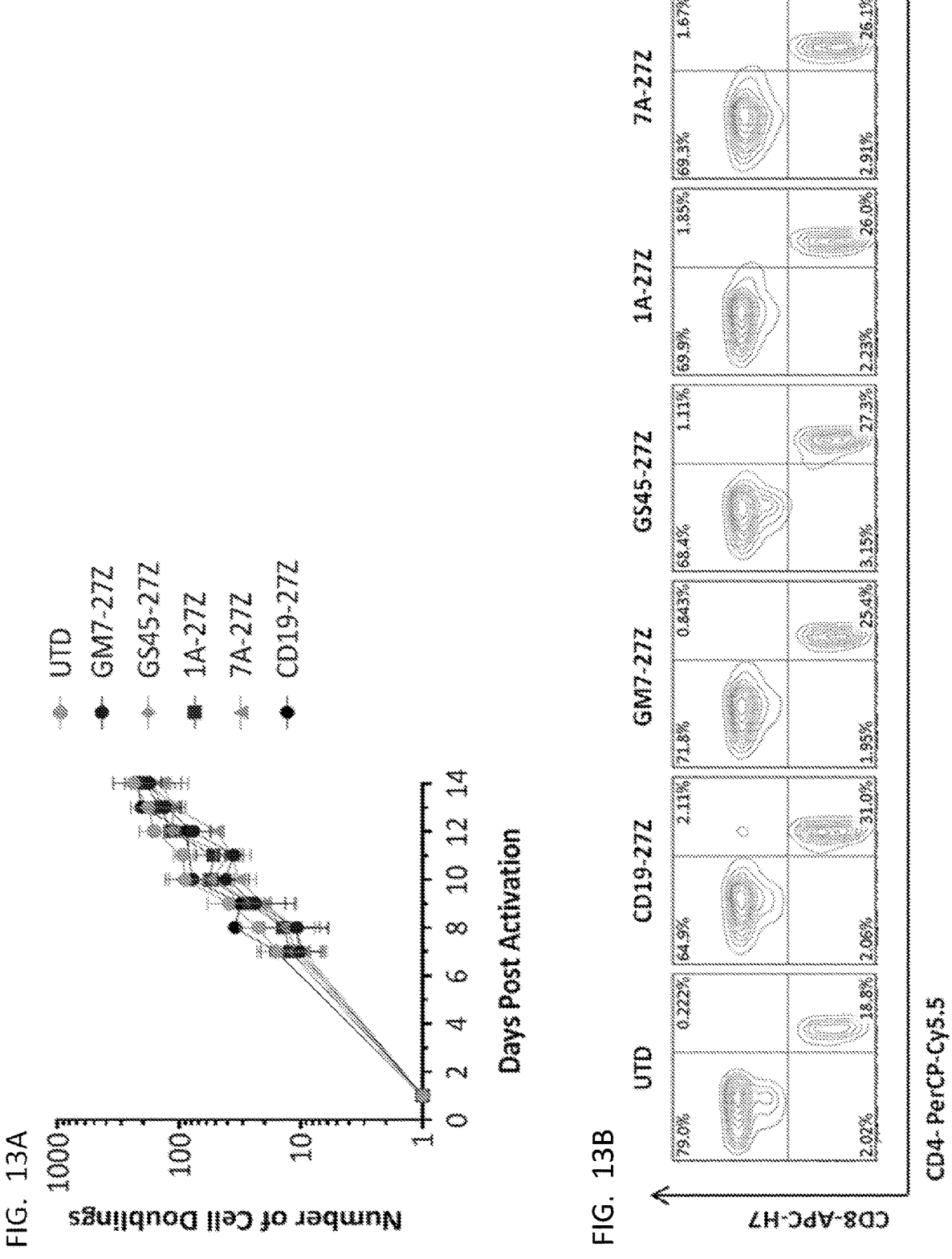

FIGS. 13A-13B depict data demonstrating that MISIIR CAR T-cell variants show a similar in vitro expansion and CD4/CD8 ratio. FIG. 13A shows the number of cell doublings during a period of 14 days after activation with CD3/CD28 beads. Combined data from 6 donors is represented as mean±SD. FIG. 13B shows T-cells stained at day 14 post-activation for CD4 (X-axis) and CD8 (Y-axis). Cells were previously gated on live/CD3+. Data from one representative donor is represented.

Figure 14A:
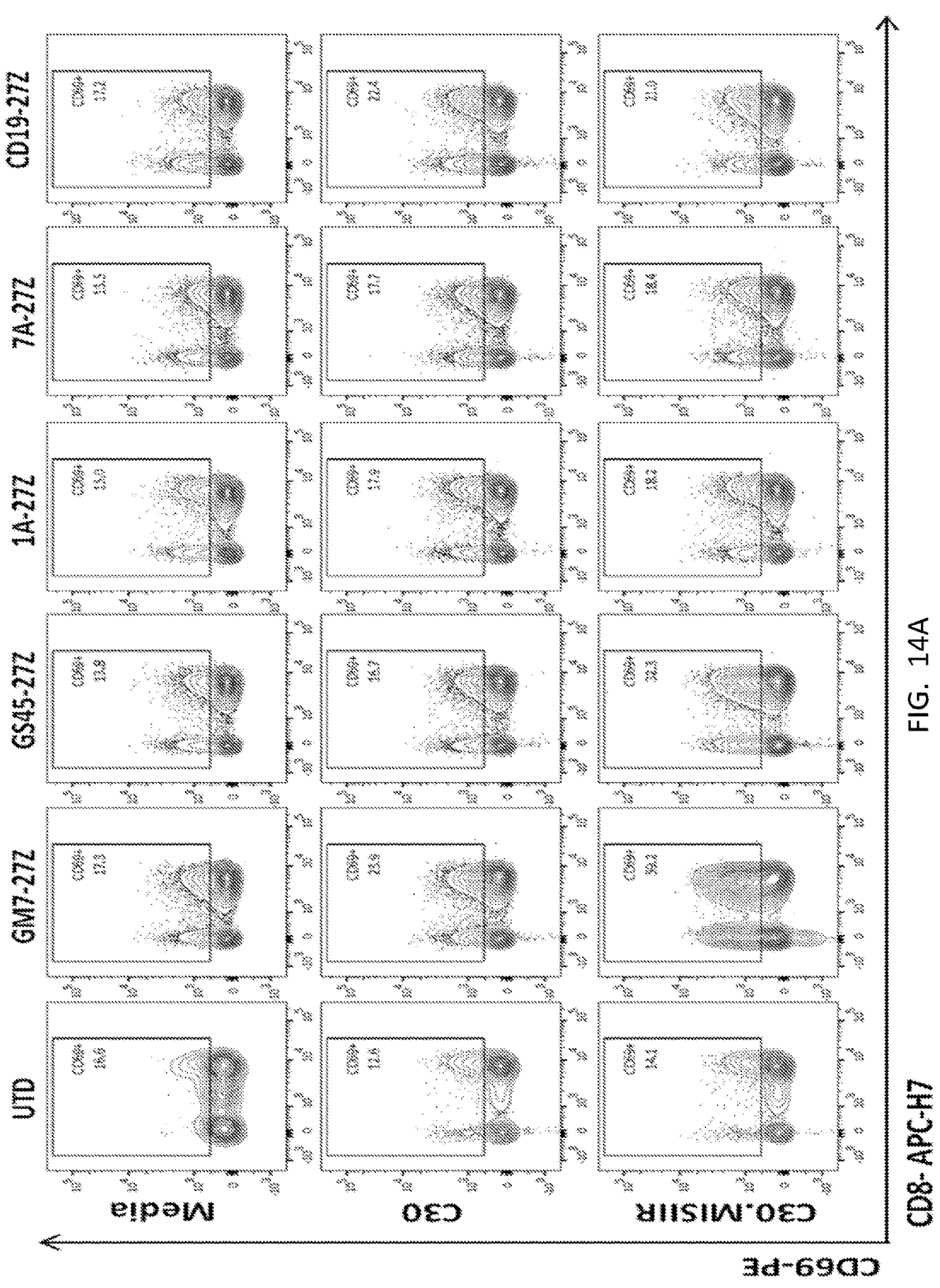
Figure 14B:
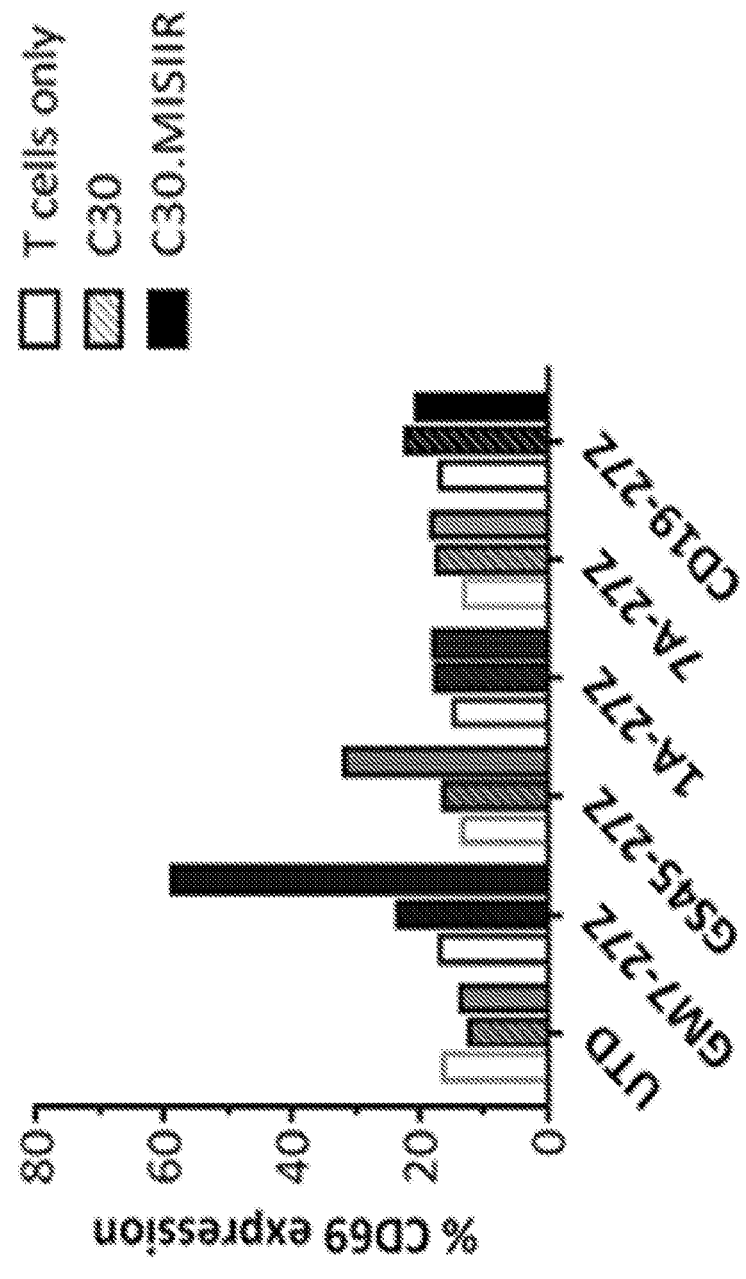

FIGS. 14A-14B depict staining of the activation marker CD69 in CAR-T cells in co-culture with C30 or C30.MISIIR target cells. FIG. 14A shows CD69 upregulation after 24 hours of co-culture. CD69 (Y-Axis) versus CD8 (X-Axis) is represented for live/CD3+ gated cells. FIG. 14B shows quantification of CD69 expression in live/CD3+ cells represented as frequency. Co-cultures of the distinct MISIIR CAR T-cells variants and C30 or C30.MISIIR were established at 1:1 E:T ratio.

Figures 15A, 15B, 15C:
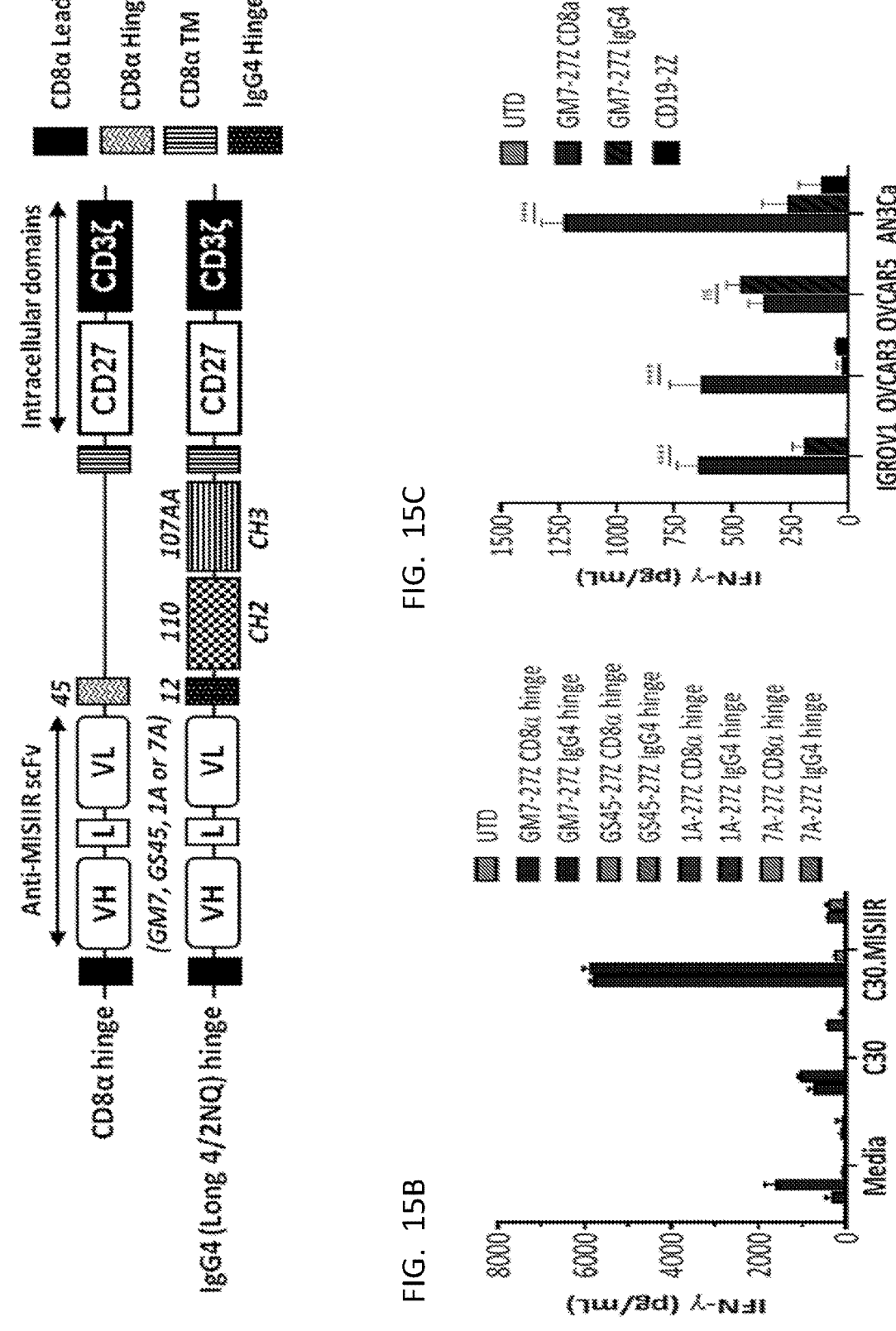

FIGS. 15A-15C depict data showing that the replacement of the CD8a hinge by a longer IgG4-based hinge does not rescue reactivity in any of the MISIIR CAR variants. FIG. 15A shows a schematic representation of CAR constructs including the CD8a hinge or the IgG4 (long 4/2NQ hinge). FIG. 15B depicts data showing IFN-γ concentration as detected by ELISA in 24-hour supernatants from co-cultures of the CAR T-cells including both hinges and C30/C30.MISIIR target cells. FIG. 15C depicts data showing IFN-γ concentration as detected by ELISA in 24-hour supernatants from co-cultures of GM7 CAR T-cells including both hinges and tumor cell lines expressing endogenous levels of MISIIR. Data is represented as mean±SD.

Figure 16A:
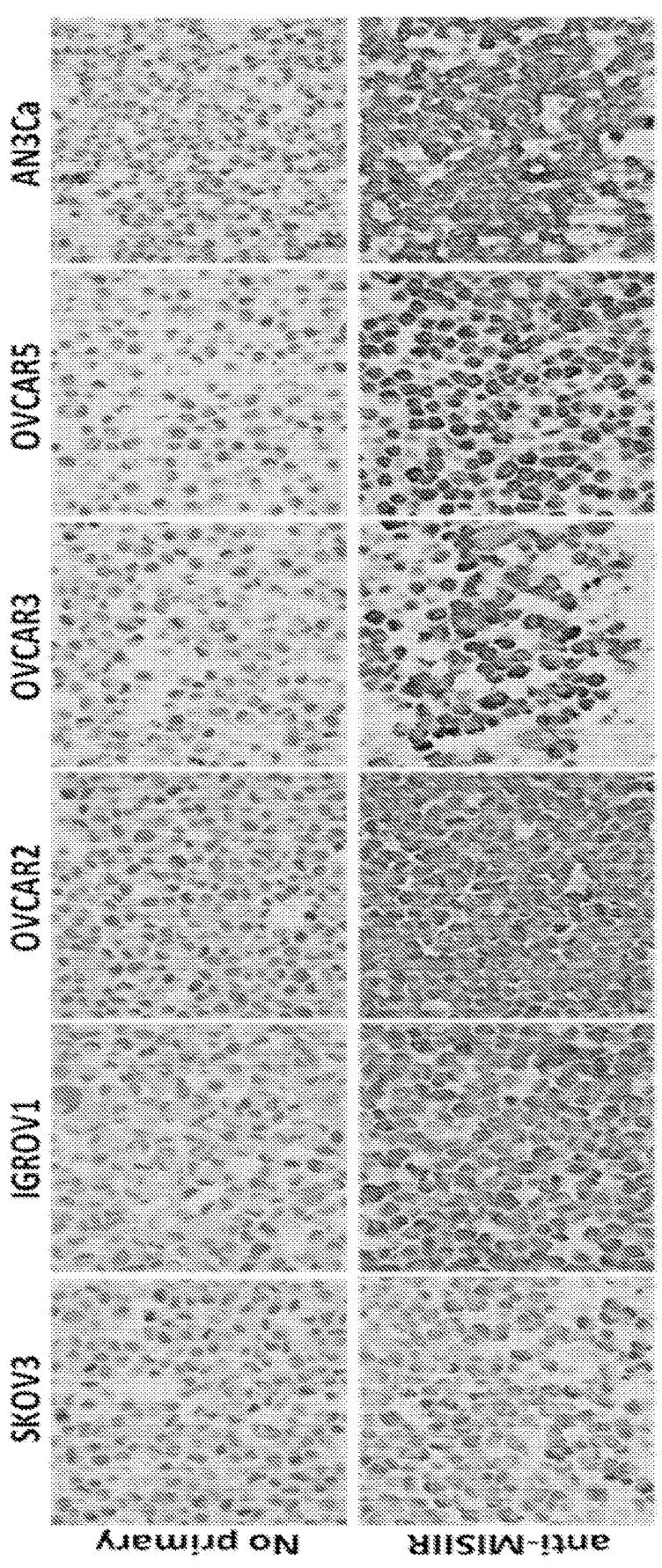
Figure 16B:
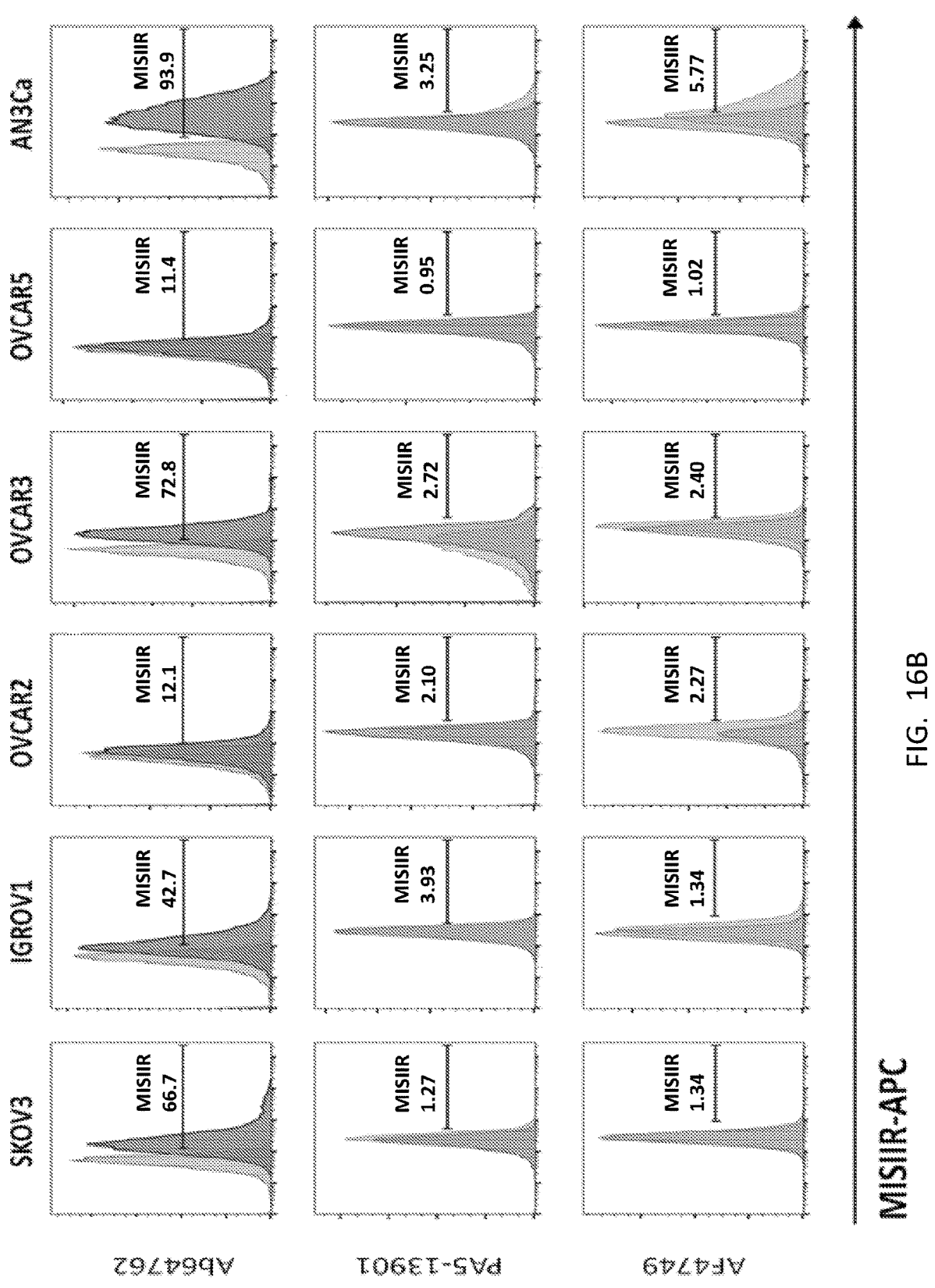

FIGS. 16A-16B depict data showing that MISIR is expressed in ovarian and endometrial cancer cell lines. FIG. 16A shows endogenous levels of MISIIR expression in a panel of human ovarian (SKOV3, IGROV1, OVCAR2, OVCAR3, and OVCAR5) and endometrial (AN3Ca) cancer cell lines as assessed by IHC staining (upper panel shows negative control in the absence of primary antibody). FIG. 16B shows endogenous levels of MISIR expression in a panel of human ovarian (SKOV3, IGROV1, OVCAR2, OVCAR3, and OVCAR5) and endometrial (AN3Ca) cancer cell lines as assessed by flow cytometry using different antibodies.

Figures 17A, 17B, 17C:
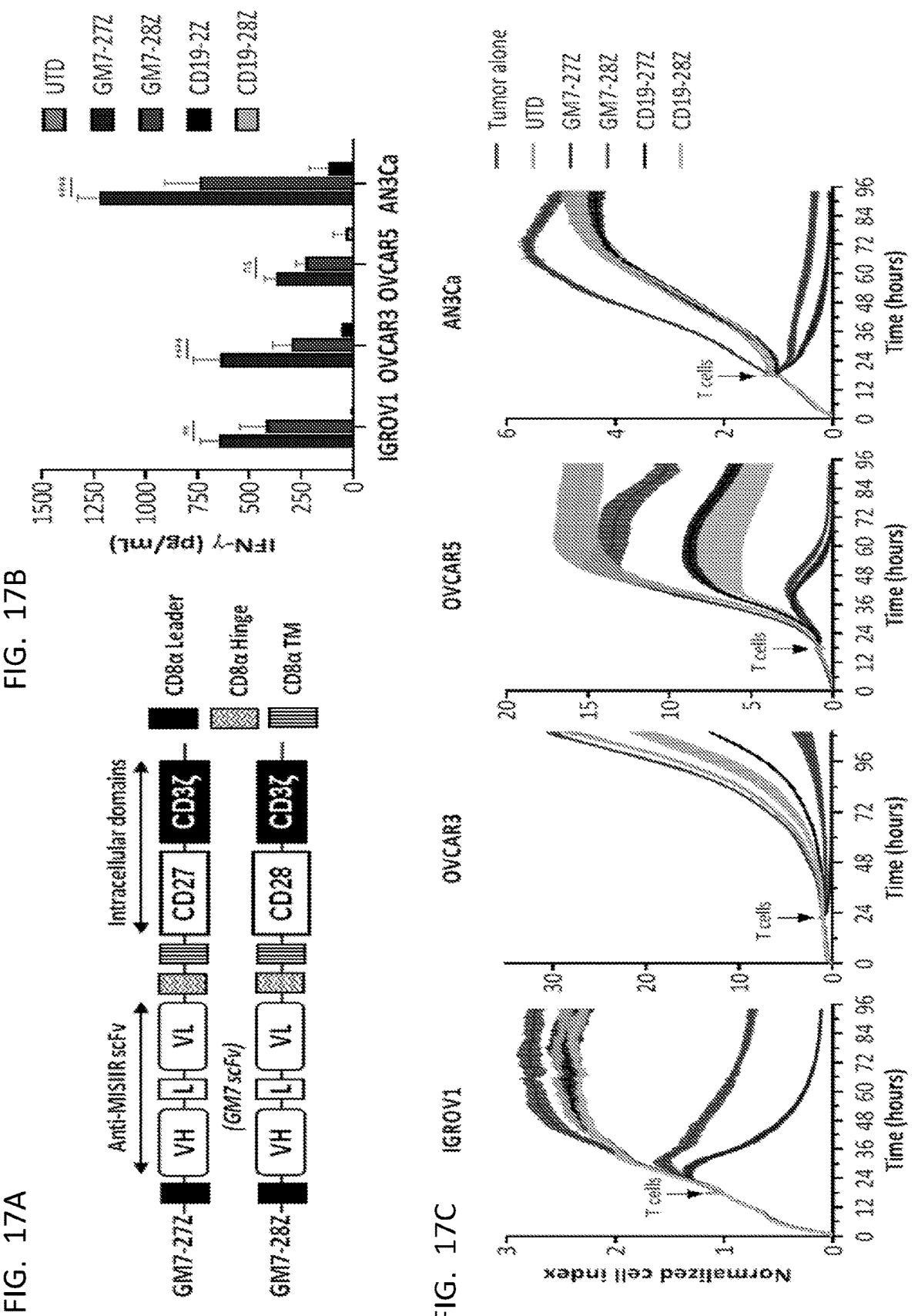

FIGS. 17A-17C depict data showing that CD27 co-stimulated GM7 CAR construct secretes higher IFN-γ levels and possess faster killing kinetics than CD28 counterpart in co-culture with MISIIR-expressing tumor cells. FIG. 17A is a schematic representation of GM7 CAR constructs including the CD27 or CD28 co-stimulatory domains. FIG. 17B depicts data showing antigen-specific IFN-γ production by CD27 or CD28 co-stimulated CAR T-cells as detected by ELISA from 24-hour co-culture supernatants. Co-cultures were established at a 1:1 E:T ratio. Significance was determined by two-way ANOVA and Dunnett's multiple comparison test as compared to UTD group. ** p<0.0001;  p<0.01. FIG. 17C shows real-time cytotoxicity assays established at a 3:1 E:T ratio. Data is represented as mean±SD. Arrows indicate time of CAR T-cell addition.

Figures 18A, 18B, 18C:
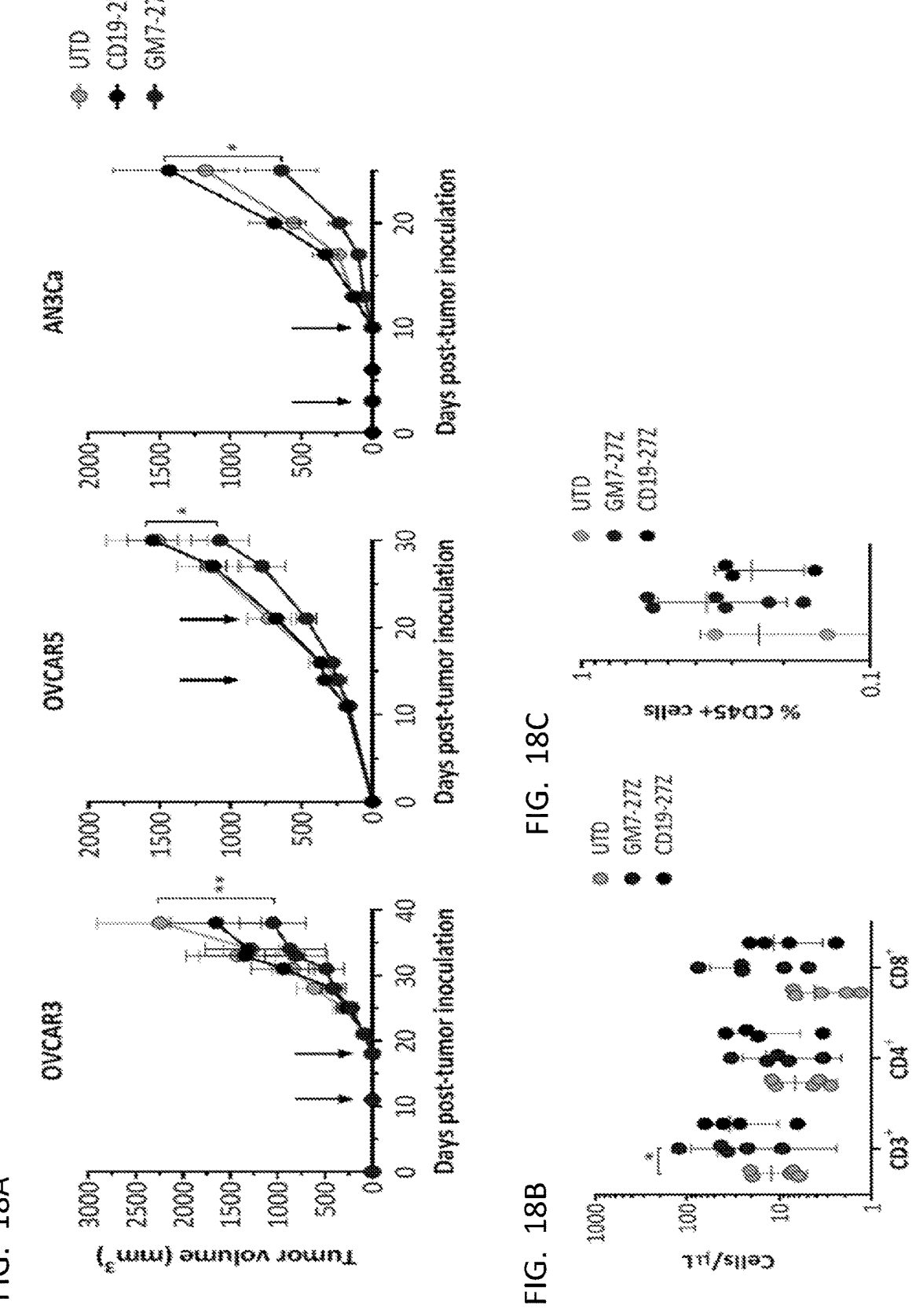

FIGS. 18A-18C depict data demonstrating that GM7 CAR T-cells has antigen-specific reactivity against endogenous MISIR in vivo. OVCAR3, OVCAR5 or AN3Ca GFP-fLuc cells were inoculated into NSG mice subcutaneously. Once the tumors were established, mice were randomized in groups and received two intravenous doses of CAR+ T-cells (5×106) given one week apart. FIG. 18A shows tumor growth as monitored by caliper measurement. Arrows indicate times of T-cell administration. Data is represented as mean±SD. Significance was determined by two-way ANOVA and Tukey's multiple comparison test. * p<0.05, p<0.01. FIG. 18B** shows absolute numbers of human CD3+, CD4+, and CD8+ T-cells as quantified by flow cytometry on day 18 post-T cell injection for the AN3Ca model. Data is represented as mean±SD. Significance was determined by two-way ANOVA and Tukey's multiple comparison test. * p<0.05. FIG. 18C shows the frequency of CD45+ cells in tumor digests at the endpoint of the AN3Ca study.

Figures 19A, 19B, 19C:
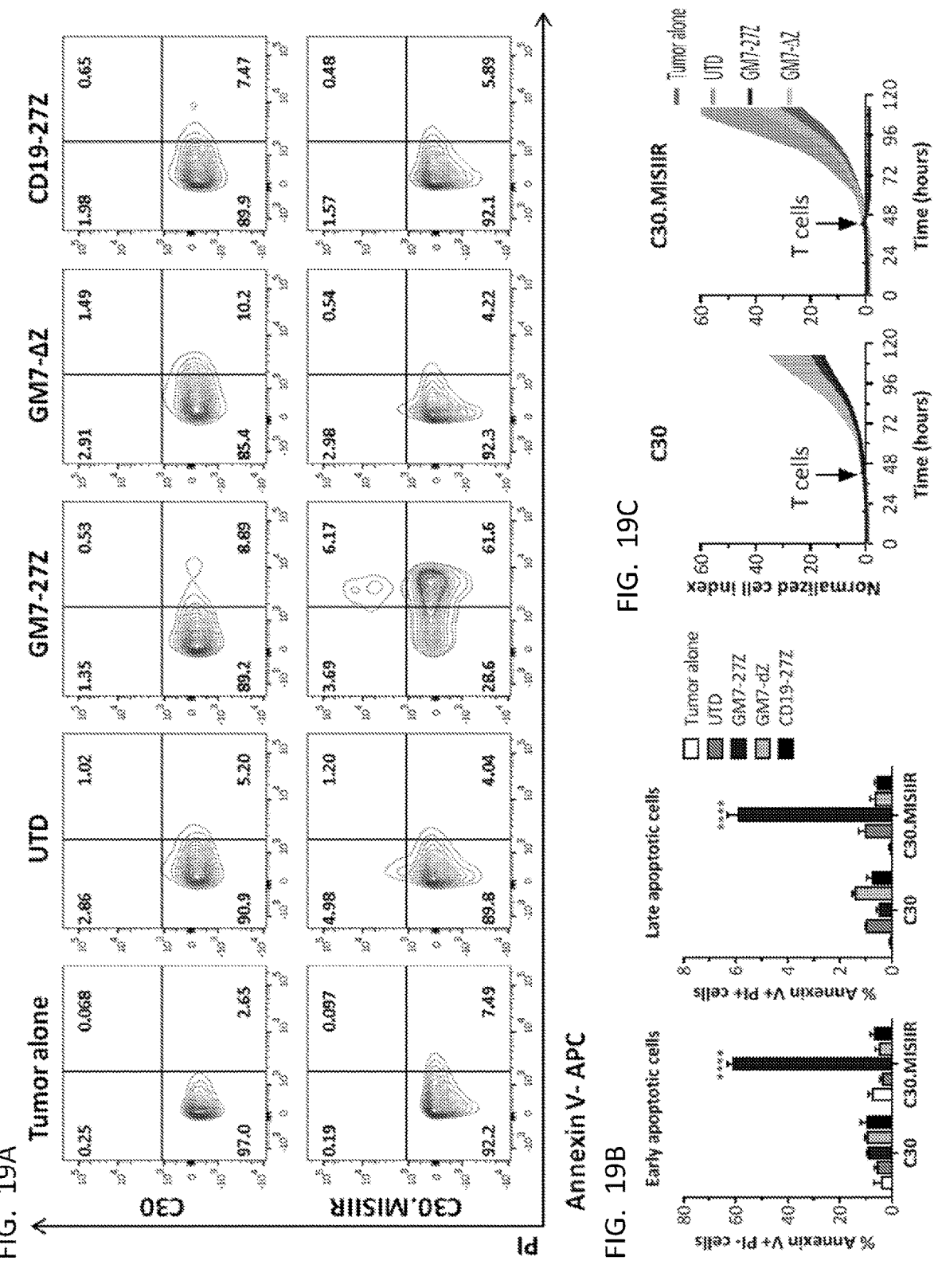
Figures 19D, 19E, 19F:
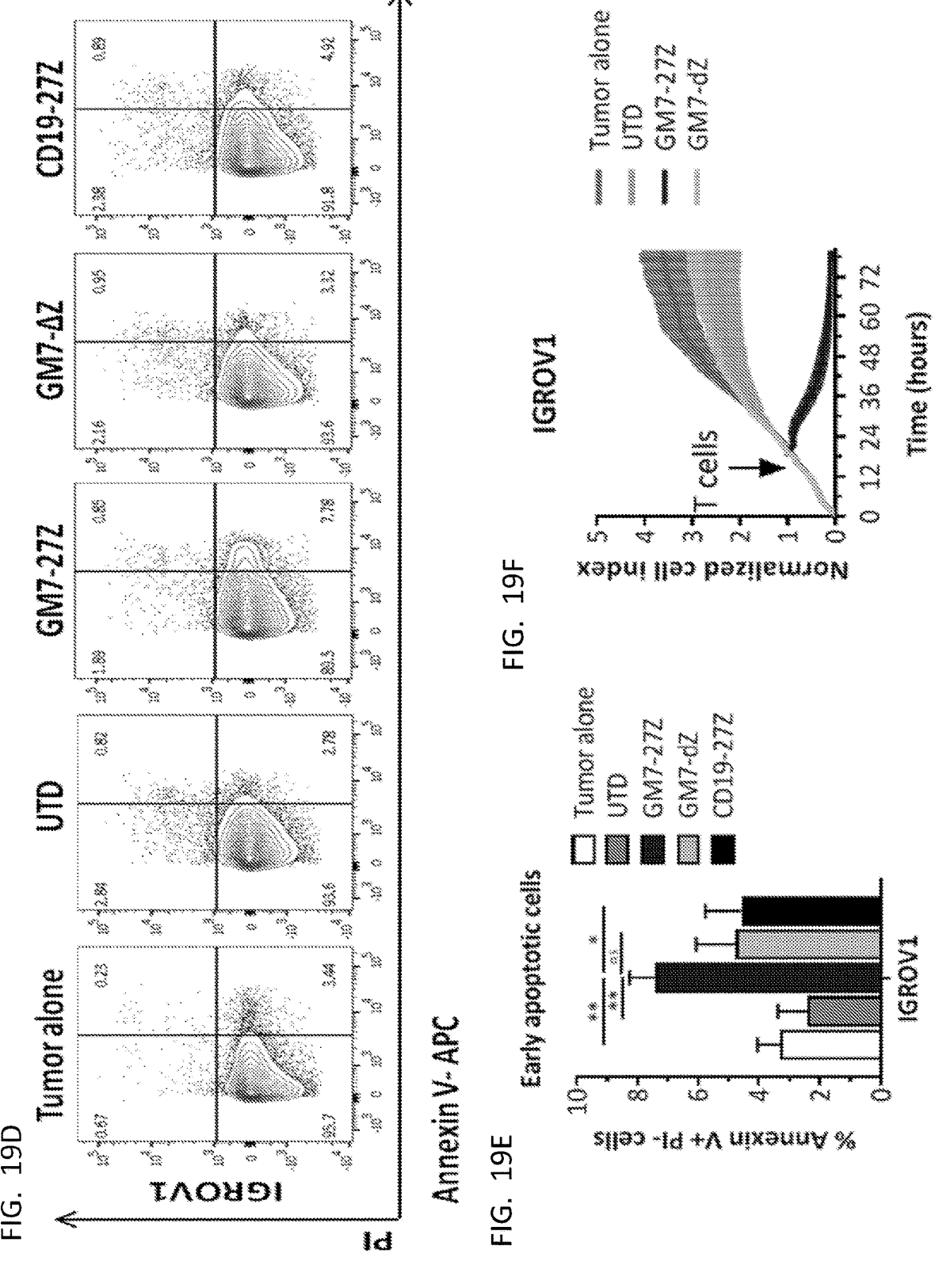

FIGS. 19A-19F depict data demonstrating that GM7 CAR T-cells killing mechanism does not involve ligand-induced apoptosis. FIG. 19A shows representative flow plots of the staining of the apoptotic markers Annexin V (X-axis) and PI (Y-axis) after 24 hours of co-culture with C30 or C30.MISIIR target cells at 1:1 E:T ratio. FIG. 19B shows the frequency of early (Annexin V+ PI−) and late (Annexin V+ PI+) apoptotic cells. FIG. 19C depicts data showing real-time cytotoxicity assays established at a 1:1 E:T ratio. FIG. 19D shows representative flow plots of the staining of apoptotic markers Annexin V (X-axis) and PI (Y-axis) after 48 hours of co-culture with IGROV1 target cells at 3:1 E:T ratio. FIG. 19E depicts data showing the frequency of early (Annexin V+ PI−) apoptotic cells. FIG. 19F shows real-time cytotoxicity assays established at a 3:1 E:T ratio. Data is represented as mean±SD. Significance was determined by two-way ANOVA and Dunnett's multiple comparison test as compared to UTD group. ** p<0.0001;  p<0.001; * p<0.05.

Figures 20A, 20B:
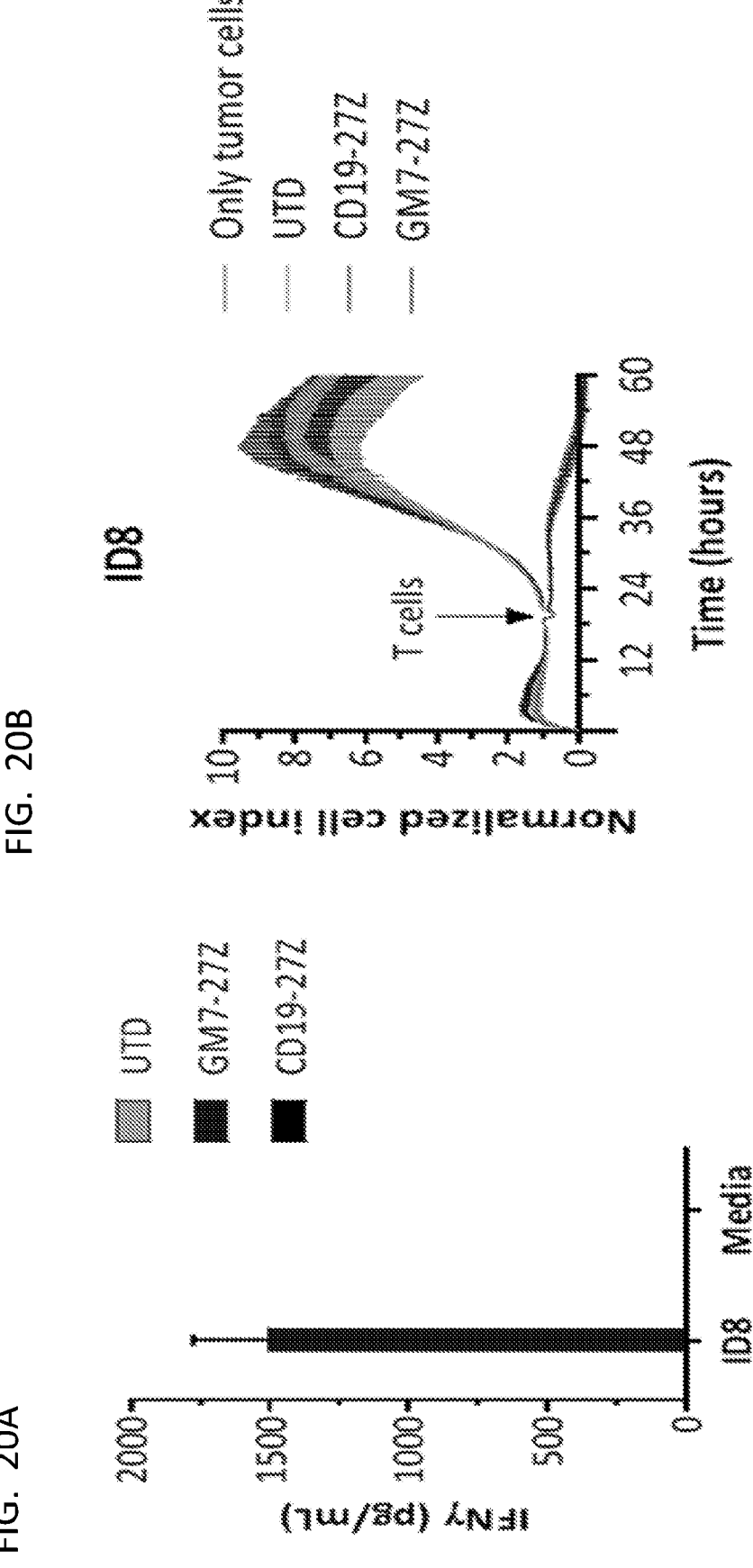

FIGS. 20A-20B depict data showing that GM7-27Z CAR cross-reacts with mouse MISIIR protein. FIG. 20A shows antigen-specific IFN-γ production by GM7 CAR T-cells as detected by ELISA from 24 hour supernatants from co-cultures with ID8 mouse ovarian cancer cell line. Co-cultures were established at a 1:1 E:T ratio. FIG. 20B shows real-time cytotoxicity assays established at a 3:1 E:T ratio. Data is represented as mean±SD.

DETAILED DESCRIPTION

A. Definitions

Unless otherwise defined, scientific and technical terms used herein have the meanings that are commonly understood by those of ordinary skill in the art. In the event of any latent ambiguity, definitions provided herein take precedent over any dictionary or extrinsic definition. Unless otherwise required by context, singular terms shall include pluralities and plural terms shall include the singular. The use of "or" means "and/or" unless stated otherwise. The use of the term "including," as well as other forms, such as "includes" and "included," is not limiting.

Generally, nomenclature used in connection with cell and tissue culture, molecular biology, immunology, microbiology, genetics and protein and nucleic acid chemistry and hybridization described herein is well-known and commonly used in the art. The methods and techniques provided herein are generally performed according to conventional methods well known in the art and as described in various general and more specific references that are cited and discussed throughout the present specification unless otherwise indicated. Enzymatic reactions and purification techniques are performed according to manufacturer's specifications, as commonly accomplished in the art or as described herein. The nomenclatures used in connection with, and the laboratory procedures and techniques of, analytical chemistry, synthetic organic chemistry, and medicinal and pharmaceutical chemistry described herein are those well-known and commonly used in the art. Standard techniques are used for chemical syntheses, chemical analyses, pharmaceutical preparation, formulation, and delivery, and treatment of patients.

That the disclosure may be more readily understood, select terms are defined below.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of 20% or 10%, more preferably +5%, even more preferably ±1%, and still more preferably +0.1% from the specified value, as such variations are appropriate to perform the disclosed methods.

"Activation," as used herein, refers to the state of a T cell that has been sufficiently stimulated to induce detectable cellular proliferation. Activation can also be associated with induced cytokine production, and detectable effector functions. The term "activated T cells" refers to, among other things, T cells that are undergoing cell division.

As used herein, to "alleviate" a disease means reducing the severity of one or more symptoms of the disease.

The term "antigen" as used herein is defined as a molecule that provokes an immune response. This immune response may involve either antibody production, or the activation of specific immunologically-competent cells, or both. The skilled artisan will understand that any macromolecule, including virtually all proteins or peptides, can serve as an antigen.

Furthermore, antigens can be derived from recombinant or genomic DNA. A skilled artisan will understand that any DNA, which comprises a nucleotide sequences or a partial nucleotide sequence encoding a protein that elicits an immune response therefore encodes an "antigen" as that term is used herein. Furthermore, one skilled in the art will understand that an antigen need not be encoded solely by a full length nucleotide sequence of a gene. It is readily apparent that the present invention includes, but is not limited to, the use of partial nucleotide sequences of more than one gene and that these nucleotide sequences are arranged in various combinations to elicit the desired immune response. Moreover, a skilled artisan will understand that an antigen need not be encoded by a "gene" at all. It is readily apparent that an antigen can be generated synthesized or can be derived from a biological sample. Such a biological sample can include, but is not limited to a tissue sample, a tumor sample, a cell or a biological fluid.

As used herein, the term "autologous" is meant to refer to any material derived from the same individual to which it is later to be re-introduced into the individual.

A "co-stimulatory molecule" refers to the cognate binding partner on a T cell that specifically binds with a co-stimulatory ligand, thereby mediating a co-stimulatory response by the T cell, such as, but not limited to, proliferation. Co-stimulatory molecules include, but are not limited to an MHC class I molecule, BTLA and a Toll ligand receptor.

A "co-stimulatory signal", as used herein, refers to a signal, which in combination with a primary signal, such as TCR/CD3 ligation, leads to T cell proliferation and/or upregulation or downregulation of key molecules.

A "disease" is a state of health of an animal wherein the animal cannot maintain homeostasis, and wherein if the disease is not ameliorated then the animal's health continues to deteriorate. In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

The term "downregulation" as used herein refers to the decrease or elimination of gene expression of one or more genes.

"Effective amount" or "therapeutically effective amount" are used interchangeably herein, and refer to an amount of a compound, formulation, material, or composition, as described herein effective to achieve a particular biological result or provides a therapeutic or prophylactic benefit. Such results may include, but are not limited to an amount that when administered to a mammal, causes a detectable level of immune suppression or tolerance compared to the immune response detected in the absence of the composition of the invention. The immune response can be readily assessed by a plethora of art-recognized methods. The skilled artisan would understand that the amount of the composition administered herein varies and can be readily determined based on a number of factors such as the disease or condition being treated, the age and health and physical condition of the mammal being treated, the severity of the disease, the particular compound being administered, and the like.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the noncoding strand, used as the template for transcription of a gene or cDNA, can be referred to as encoding the protein or other product of that gene or cDNA.

As used herein "endogenous" refers to any material from or produced inside an organism, cell, tissue or system.

The term "epitope" as used herein is defined as a small chemical molecule on an antigen that can elicit an immune response, inducing B and/or T cell responses. An antigen can have one or more epitopes. Most antigens have many epitopes; i.e., they are multivalent. In general, an epitope is roughly about 10 amino acids and/or sugars in size. Preferably, the epitope is about 4-18 amino acids, more preferably about 5-16 amino acids, and even more most preferably 6-14 amino acids, more preferably about 7-12, and most preferably about 8-10 amino acids. One skilled in the art understands that generally the overall three-dimensional structure, rather than the specific linear sequence of the molecule, is the main criterion of antigenic specificity and therefore distinguishes one epitope from another. Based on the present disclosure, a peptide used in the present invention can be an epitope.

As used herein, the term "exogenous" refers to any material introduced from or produced outside an organism, cell, tissue or system.

The term "expand" as used herein refers to increasing in number, as in an increase in the number of T cells. In one embodiment, the T cells that are expanded ex vivo increase in number relative to the number originally present in the culture. In another embodiment, the T cells that are expanded ex vivo increase in number relative to other cell types in the culture. The term "ex vivo," as used herein, refers to cells that have been removed from a living organism, (e.g., a human) and propagated outside the organism (e.g., in a culture dish, test tube, or bioreactor).

The term "expression" as used herein is defined as the transcription and/or translation of a particular nucleotide sequence driven by its promoter.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses (e.g., Sendai viruses, lentiviruses, retroviruses, adenoviruses, and adeno-associated viruses) that incorporate the recombinant polynucleotide.

"Identity" as used herein refers to the subunit sequence identity between two polymeric molecules particularly between two amino acid molecules, such as, between two polypeptide molecules. When two amino acid sequences have the same residues at the same positions; e.g., if a position in each of two polypeptide molecules is occupied by an arginine, then they are identical at that position. The identity or extent to which two amino acid sequences have the same residues at the same positions in an alignment is often expressed as a percentage. The identity between two amino acid sequences is a direct function of the number of matching or identical positions; e.g., if half (e.g., five positions in a polymer ten amino acids in length) of the positions in two sequences are identical, the two sequences are 50% identical; if 90% of the positions (e.g., 9 of 10), are matched or identical, the two amino acids sequences are 90% identical.

The term "immune response" as used herein is defined as a cellular response to an antigen that occurs when lymphocytes identify antigenic molecules as foreign and induce the formation of antibodies and/or activate lymphocytes to remove the antigen.

The term "immunosuppressive" is used herein to refer to reducing overall immune response.

"Isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

A "lentivirus" as used herein refers to a genus of the Retroviridae family. Lentiviruses are unique among the retroviruses in being able to infect non-dividing cells; they can deliver a significant amount of genetic information into the DNA of the host cell, so they are one of the most efficient methods of a gene delivery vector. HIV, SIV, and FIV are all examples of lentiviruses. Vectors derived from lentiviruses offer the means to achieve significant levels of gene transfer in vivo.

By the term "modified" as used herein, is meant a changed state or structure of a molecule or cell of the invention. Molecules may be modified in many ways, including chemically, structurally, and functionally. Cells may be modified through the introduction of nucleic acids.

By the term "modulating," as used herein, is meant mediating a detectable increase or decrease in the level of a response in a subject compared with the level of a response in the subject in the absence of a treatment or compound, and/or compared with the level of a response in an otherwise identical but untreated subject. The term encompasses perturbing and/or affecting a native signal or response thereby mediating a beneficial therapeutic response in a subject, preferably, a human.

In the context of the present invention, the following abbreviations for the commonly occurring nucleic acid bases are used. "A" refers to adenosine, "C" refers to cytosine, "G" refers to guanosine, "T" refers to thymidine, and "U" refers to uridine.

The term "oligonucleotide" typically refers to short polynucleotides. It will be understood that when a nucleotide sequence is represented by a DNA sequence (i.e., A, T, C, G), this also includes an RNA sequence (i.e., A, U, C, G) in which "U" replaces "T."

Unless otherwise specified, a "nucleotide sequence encoding an amino acid sequence" includes all nucleotide sequences that are degenerate versions of each other and that encode the same amino acid sequence. The phrase nucleotide sequence that encodes a protein or an RNA may also include introns to the extent that the nucleotide sequence encoding the protein may in some version contain an intron(s).

"Parenteral" administration of an immunogenic composition includes, e.g., subcutaneous (s.c.), intravenous (i.v.), intramuscular (i.m.), or intrasternal injection, or infusion techniques.

The term "polynucleotide" as used herein is defined as a chain of nucleotides. Furthermore, nucleic acids are polymers of nucleotides. Thus, nucleic acids and polynucleotides as used herein are interchangeable. One skilled in the art has the general knowledge that nucleic acids are polynucleotides, which can be hydrolyzed into the monomeric "nucleotides." The monomeric nucleotides can be hydrolyzed into nucleosides. As used herein polynucleotides include, but are not limited to, all nucleic acid sequences which are obtained by any means available in the art, including, without limitation, recombinant means, i.e., the cloning of nucleic acid sequences from a recombinant library or a cell genome, using ordinary cloning technology and PCR, and the like, and by synthetic means.

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

By the term "specifically binds," as used herein with respect to an antibody, is meant an antibody which recognizes a specific antigen, but does not substantially recognize or bind other molecules in a sample. For example, an antibody that specifically binds to an antigen from one species may also bind to that antigen from one or more species. But, such cross-species reactivity does not itself alter the classification of an antibody as specific. In another example, an antibody that specifically binds to an antigen may also bind to different allelic forms of the antigen. However, such cross reactivity does not itself alter the classification of an antibody as specific. In some instances, the terms "specific binding" or "specifically binding," can be used in reference to the interaction of an antibody, a protein, or a peptide with a second chemical species, to mean that the interaction is dependent upon the presence of a particular structure (e.g., an antigenic determinant or epitope) on the chemical species, for example, an antibody recognizes and binds to a specific protein structure rather than to proteins generally. If an antibody is specific for epitope "A", the presence of a molecule containing epitope A (or free, unlabeled A), in a reaction containing labeled "A" and the antibody, will reduce the amount of labeled A bound to the antibody.

By the term "stimulation," is meant a primary response induced by binding of a stimulatory molecule (e.g., a TCR/CD3 complex) with its cognate ligand thereby mediating a signal transduction event, such as, but not limited to, signal transduction via the TCR/CD3 complex. Stimulation can mediate altered expression of certain molecules, such as downregulation of TGF-beta, and/or reorganization of cytoskeletal structures, and the like.

A "stimulatory molecule," as the term is used herein, means a molecule on a T cell that specifically binds with a cognate stimulatory ligand present on an antigen presenting cell.

A "stimulatory ligand," as used herein, means a ligand that when present on an antigen presenting cell (e.g., an aAPC, a dendritic cell, a B-cell, and the like) can specifically bind with a cognate binding partner (referred to herein as a "stimulatory molecule") on a T cell, thereby mediating a primary response by the T cell, including, but not limited to, activation, initiation of an immune response, proliferation, and the like. Stimulatory ligands are well-known in the art and encompass, inter alia, an MHC Class I molecule loaded with a peptide, an anti-CD3 antibody, a superagonist anti-CD28 antibody, and a superagonist anti-CD2 antibody.

The term "subject" is intended to include living organisms in which an immune response can be elicited (e.g., mammals). A "subject" or "patient," as used therein, may be a human or non-human mammal. Non-human mammals include, for example, livestock and pets, such as ovine, bovine, porcine, canine, feline and murine mammals. Preferably, the subject is human.

A "target site" or "target sequence" refers to a nucleic acid sequence that defines a portion of a nucleic acid to which a binding molecule may specifically bind under conditions sufficient for binding to occur. In some embodiments, a target sequence refers to a genomic nucleic acid sequence that defines a portion of a nucleic acid to which a binding molecule may specifically bind under conditions sufficient for binding to occur.

As used herein, the term "T cell receptor" or "TCR" refers to a complex of membrane proteins that participate in the activation of T cells in response to the presentation of antigen. The TCR is responsible for recognizing antigens bound to major histocompatibility complex molecules. TCR is composed of a heterodimer of an alpha (α) and beta (β) chain, although in some cells the TCR consists of gamma and delta (γ/δ) chains. TCRs may exist in alpha/beta and gamma/delta forms, which are structurally similar but have distinct anatomical locations and functions. Each chain is composed of two extracellular domains, a variable and constant domain. In some embodiments, the TCR may be modified on any cell comprising a TCR, including, for example, a helper T cell, a cytotoxic T cell, a memory T cell, regulatory T cell, natural killer T cell, and gamma delta T cell.

The term "therapeutic" as used herein means a treatment and/or prophylaxis. A therapeutic effect is obtained by suppression, remission, or eradication of a disease state.

The term "transfected" or "transformed" or "transduced" as used herein refers to a process by which exogenous nucleic acid is transferred or introduced into the host cell. A "transfected" or "transformed" or "transduced" cell is one which has been transfected, transformed or transduced with exogenous nucleic acid. The cell includes the primary subject cell and its progeny.

To "treat" a disease as the term is used herein, means to reduce the frequency or severity of at least one sign or symptom of a disease or disorder experienced by a subject.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, Sendai viral vectors, adenoviral vectors, adeno-associated virus vectors, retroviral vectors, lentiviral vectors, and the like.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

B. Chimeric Antigen Receptors

The present invention provides a Müllerian inhibiting substance type 2 receptor (MISIIR)-specific chimeric antigen receptor (CAR). Also provided are compositions and methods for modified immune cells or precursors thereof, e.g., modified T cells, comprising a MISIIR-specific CAR. Thus, in some embodiments, the immune cell has been genetically modified to express the CAR. The CAR of the present invention comprises an antigen binding domain, a transmembrane domain, and an intracellular domain.

The antigen binding domain may be operably linked to another domain of the CAR, such as the transmembrane domain or the intracellular domain, both described elsewhere herein, for expression in the cell. In one embodiment, a first nucleic acid sequence encoding the antigen binding domain is operably linked to a second nucleic acid encoding a transmembrane domain, and further operably linked to a third a nucleic acid sequence encoding an intracellular domain.

The antigen binding domains described herein can be combined with any of the transmembrane domains described herein, any of the intracellular domains or cytoplasmic domains described herein, or any of the other domains described herein that may be included in a CAR of the present invention. A subject CAR of the present invention may also include a hinge domain as described herein. A subject CAR of the present invention may also include a spacer domain as described herein. In some embodiments, each of the antigen binding domain, transmembrane domain, and intracellular domain is separated by a linker.

In certain embodiments, the CAR comprises a MISIIR-specific scFv, a CD8a hinge domain, a CD8a transmembrane domain, a CD27 intracellular domain, and a CD3 zeta intracellular domain. In certain embodiments, the CAR is encoded by the nucleotide sequence set forth in SEQ ID NO: 1. In certain embodiments, the CAR comprises the amino acid sequence set forth in SEQ ID NO: 2.

```
MISIIR-specific CAR nucleotide sequence
(SEQ ID NO: 1):
atggccttaccagtgaccgccttgctcctgccgctg gccttgctgctccacgccgccaggccgggatccgc ccaggtgcagctggtgcagtctggaactgaggtga agaggcctggggcctcagtgaagatctcctgcagg gctactggttacacctttagtgattatggtatcag ttggatgcgacaggcccctggacaagggcttgagt ggatgggatggatcagcgcttacaatggtaacaca aactatgcacagaagctccagggcagagtcaccat gaccacagacacgtccacgagcacagcctacatgg agctgaggagcctcagatatgacgacacggccgta tattactgtgcgagagatgggaggcgtggttcggg tatttactggggtgtgtattattacaacggtatgg acgtctggggccaagggaccacggtcaccgtctcc tcaggtggcggcggttccggaggtggtggttctgg cggtggtggcagtcagcctgtgctgactcagccac cctcagcgtctgggaccccccgggcagagggtcacc atctcttgttctggaagcaggtccaacatcggaag gaataccgtaaactggtatcagcaggtcccaggaa tggcccccaaactcctcatctatagtaataatcag
```

```
-continued
cggccctcaggggtccctgaccgattctctggctc caagtctggcacctcagcctccctggccatcagtg ggctccagtctgaggatgaggctgattattactgt gcagcatgggatgacagtctgaatggtgtggtatt cggcggagggaccaagctgaccgtcctaggtcagc ccaaggccgcccctcggctagcaccacgacgcca gcgccgcgaccaccaacaccggcgcccaccatcgc gtcgcagcccctgtccctgcgcccagaggcgtgcc ggccagcggcggggggcgcagtgcacacgaggggg ctggacttcgcctgtgatatctacatctgggcgcc cttggccgggacttgtggggtccttctcctgtcac tggttatcacccttttactgccaacgaaggaaatat agatcaaacaaaggagaaagtcctgtggagcctgc agagccttgtcgttacagctgccccagggaggagg agggcagcaccatccccatccaggaggattaccga aaaccggagcctgcctgctcccccagagtgaagtt cagcaggagcgcagacgcccccgcgtaccagcagg gccagaaccagctctataacgagctcaatctagga cgaagagaggagtacgatgtttttggacaagagacg tggccgggaccctgagatggggggaaagccgagaa ggaagaaccctcaggaaggcctgtacaatgaactg cagaaagataagatggcggaggcctacagtgagat tgggatgaaaggcgagcgccggaggggcaagggc acgatggcctttaccagggtctcagtacagccacc aaggacacctacgacgcccttcacatgcaggccct gcccctcgctaa MISIIR-specific CAR amino acid
sequence (SEQ ID NO: 2):
MALPVTALLLPLALLLHAARPGSAQVQLVQSGTEV

KRPGASVKISCRATGYTFSDYGISWMRQAPGQGLE

WMGWISAYNGNTNYAQKLQGRVTMTTDTSTSTAYM

ELRSLRYDDTAVYYCARDGRRGSGIYWGVYYNGM

DVWGQGTTVTVSSGGGGSGGGGSGGGGSQPVLTQP

PSASGTPGQRVTISCSGSRSNIGRNTVNWYQQVPG

MAPKLLIYSNNQRPSGVPDRFSGSKSGTSASLAIS

GLQSEDEADYYCAAWDDSLNGVVFGGGTKLTVLGQ

PKAAPSASTTTPAPRPPTPAPTIASQPLSLRPEAC

RPAAGGAVHTRGLDFACDIYIWAPLAGTCGVLLLS

LVITLYCQRRKYRSNKGESPVEPAEPCRYSCPREE

EGSTMQEDYWCPEPACSPRVKFSRSADAPAYQQGQ
```

-continued

```
NQLYNELNLGRREEYDVLDKRRGRDPEMGGKPRRK

NPQEGLYNELQKDKMAEAYSEIGMKGERRRGKGHD

GLYQGLSTATKDTYDALHMQALPPR
```

Tolerable variations of the CAR sequences will be known to those of skill in the art, while maintaining specific activity. For example, in some embodiments the CAR comprises an amino acid sequence that has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the amino acid sequence set forth in SEQ ID NO: 2. For example, in some embodiments the CAR is encoded by a nucleic acid sequence that has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the nucleic acid sequence set forth in SEQ ID NO: 1.

Antigen Binding Domain

The antigen binding domain of a CAR is an extracellular region of the CAR for binding to a specific target antigen including proteins, carbohydrates, and glycolipids. In some embodiments, the CAR comprises affinity to a target antigen on a target cell. The target antigen may include any type of protein, or epitope thereof, associated with the target cell. For example, the CAR may comprise affinity to a target antigen on a target cell that indicates a particular disease state of the target cell. A subject CAR of the present invention comprises an antigen binding domain that has affinity for MISIIR. In certain embodiments, the antigen binding domain of the CAR has affinity for MISIIR on a cancer cell (e.g. an ovarian cancer cell).

In certain embodiments, the antigen binding domain is selected from the group consisting of an antibody, an antigen binding fragment (Fab), and a single-chain variable fragment (scFv). In some embodiments, a MISIIR binding domain of the present invention is selected from the group consisting of a MISIIR-specific antibody, a MISIIR-specific Fab, and a MISIIR-specific scFv. In one embodiment, a MISIIR binding domain is a MISIIR-specific antibody. In one embodiment, a MISIIR binding domain is a MISIIR-specific Fab. In one embodiment, a MISIIR binding domain is a MISIIR-specific scFv.

The antigen binding domain can include any domain that binds to the antigen and may include, but is not limited to, a monoclonal antibody, a polyclonal antibody, a synthetic antibody, a human antibody, a humanized antibody, a non-human antibody, and any fragment thereof. In some embodiments, the antigen binding domain portion comprises a mammalian antibody or a fragment thereof. The choice of antigen binding domain may depend upon the type and number of antigens that are present on the surface of a target cell.

As used herein, the term "single-chain variable fragment" or "scFv" is a fusion protein of the variable regions of the heavy (VH) and light chains (VL) of an immunoglobulin (e.g., mouse or human) covalently linked to form a VH::VL heterodimer. The heavy (VH) and light chains (VL) are either joined directly or joined by a peptide-encoding linker, which connects the N-terminus of the VH with the C-terminus of the VL, or the C-terminus of the VH with the N-terminus of the VL. In some embodiments, the antigen binding domain (e.g., PSCA binding domain) comprises an scFv having the configuration from N-terminus to C-terminus, VH-linker-VL. In some embodiments, the antigen binding domain comprises an scFv having the configuration from N-terminus to C-terminus, VL-linker-VH. Those of skill in the art would be able to select the appropriate configuration for use in the present invention.

The linker is usually rich in glycine for flexibility, as well as serine or threonine for solubility. The linker can link the heavy chain variable region and the light chain variable region of the extracellular antigen-binding domain. Non-limiting examples of linkers are disclosed in Shen et al., Anal. Chem. 80(6):1910-1917 (2008) and WO 2014/087010, the contents of which are hereby incorporated by reference in their entireties. Various linker sequences are known in the art, including, without limitation, glycine serine (GS) linkers such as $(GS)_n$, $(GSGGS)_n$ (SEQ ID NO:3), $(GGGS)_n$ (SEQ ID NO:4), and $(GGGGS)_n$ (SEQ ID NO:5), where n represents an integer of at least 1. Exemplary linker sequences can comprise amino acid sequences including, without limitation, GGSG (SEQ ID NO:6), GGSGG (SEQ ID NO:7), GSGSG (SEQ ID NO:8), GSGGG (SEQ ID NO:9), GGGSG (SEQ ID NO:10), GSSSG (SEQ ID NO: 11), GGGGS (SEQ ID NO:12), GGGGSGGGGSGGGGS (SEQ ID NO:13) and the like. Those of skill in the art would be able to select the appropriate linker sequence for use in the present invention. In one embodiment, an antigen binding domain of the present invention comprises a heavy chain variable region (VH) and a light chain variable region (VL), wherein the VH and VL is separated by the linker sequence having the amino acid sequence GGGGSGGGGSGGGGS (SEQ ID NO:13), which may be encoded by the nucleic acid sequence GGTGGCGGTGGCTCGGGCGGTGGTGGGTCGGGTG GCGGCGGATCT (SEQ ID NO:14).

Despite removal of the constant regions and the introduction of a linker, scFv proteins retain the specificity of the original immunoglobulin. Single chain Fv polypeptide antibodies can be expressed from a nucleic acid comprising VH- and VL-encoding sequences as described by Huston, et al. (Proc. Nat. Acad. Sci. USA, 85:5879-5883, 1988). See, also, U.S. Pat. Nos. 5,091,513, 5,132,405 and 4,956,778; and U.S. Patent Publication Nos. 20050196754 and 20050196754. Antagonistic scFvs having inhibitory activity have been described (see, e.g., Zhao et al., Hybridoma (Larchmt) 2008 27(6):455-51; Peter et al., J Cachexia Sarcopenia Muscle 2012 Aug. 12; Shieh et al., J Imunol 2009 183(4):2277-85; Giomarelli et al., Thromb Haemost 2007 97(6):955-63; Fife et al., J Clin Invst 2006 116(8):2252-61; Brocks et al., Immunotechnology 1997 3(3):173-84; Moosmayer et al., Ther Immunol 1995 2(10:31-40). Agonistic scFvs having stimulatory activity have been described (see, e.g., Peter et al., J Bioi Chem 2003 25278(38):36740-7; Xie et al., Nat Biotech 1997 15(8):768-71; Ledbetter et al., Crit Rev Immunol 1997 17(5-6):427-55; Ho et al., BioChim Biophys Acta 2003 1638(3):257-66).

As used herein, "Fab" refers to a fragment of an antibody structure that binds to an antigen but is monovalent and does not have a Fc portion, for example, an antibody digested by the enzyme papain yields two Fab fragments and an Fc fragment (e.g., a heavy (H) chain constant region; Fc region that does not bind to an antigen).

As used herein, "F(ab')2" refers to an antibody fragment generated by pepsin digestion of whole IgG antibodies, wherein this fragment has two antigen binding (ab') (bivalent) regions, wherein each (ab') region comprises two separate amino acid chains, a part of a H chain and a light (L) chain linked by an S—S bond for binding an antigen and where the remaining H chain portions are linked together. A "F(ab')2" fragment can be split into two individual Fab' fragments.

In some embodiments, the antigen binding domain may be derived from the same species in which the CAR will ultimately be used. For example, for use in humans, the antigen binding domain of the CAR may comprise a human antibody or a fragment thereof. In some embodiments, the antigen binding domain may be derived from a different species in which the CAR will ultimately be used. For example, for use in humans, the antigen binding domain of the CAR may comprise a murine antibody or a fragment thereof.

As described herein, a CAR of the present disclosure having affinity for MISIIR on a target cell (e.g. cancer cell) may comprise a target-specific binding domain. In some embodiments, the target-specific binding domain is a murine target-specific binding domain, e.g., the target-specific binding domain is of murine origin. In some embodiments, the target-specific binding domain is a human target-specific binding domain, e.g., the target-specific binding domain is of human origin. In one embodiment, a CAR of the present disclosure having affinity for MISIIR on a target cell may comprise a MISIIR binding domain.

In some embodiments, a CAR of the present disclosure may have affinity for one or more target antigens on one or more target cells. In some embodiments, a CAR may have affinity for one or more target antigens on a target cell. In such embodiments, the CAR is a bispecific CAR, or a multi-specific CAR. In some embodiments, the CAR comprises one or more target-specific binding domains that confer affinity for one or more target antigens. In some embodiments, the CAR comprises one or more target-specific binding domains that confer affinity for the same target antigen. For example, a CAR comprising one or more target-specific binding domains having affinity for the same target antigen could bind distinct epitopes of the target antigen. When a plurality of target-specific binding domains is present in a CAR, the binding domains may be arranged in tandem and may be separated by linker peptides. For example, in a CAR comprising two target-specific binding domains, the binding domains are connected to each other covalently on a single polypeptide chain, through an oligo- or polypeptide linker, an Fc hinge region, or a membrane hinge region.

In certain embodiments, the MISIIR binding domain comprises the amino acid sequence set forth in SEQ ID NO: 15. In certain embodiments, the MISIIR binding domain is encoded by the nucleotide sequence set forth in SEQ ID NO: 16.

Tolerable variations of the MISIIR binding domain will be known to those of skill in the art, while maintaining specific binding to MISIIR. For example, in some embodiments the MISIIR binding domain comprises an amino acid sequence that has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to the amino acid sequences set forth in SEQ ID NO: 15. For example, in some embodiments the MISIIR binding domain is encoded by a nucleic acid sequence that has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to any of the nucleic acid sequences set forth in SEQ ID NO: 16.

```
MISIIR scFv amino acid sequence
(linker is underlined
(SEQ ID NO: 15):
AQVQLVQSGTEVKRPGASVKISCRATGYTFSDYGISWMRQAPGQGLEWM

GWISAYNGNTNYAQKLQGRVTMTTDTSTSTAYMELRSIRYDDTAVYYCA

RDGRRGSGIYWGVYYYNGMDVWGQGTTVTVSSGGGGSGGGGSGGGGSQPV

LTQPPSASGTPGORVTISCSGSRSNIGRNTVNWYQQVPGMAPKLLIYSN

NQRPSGVPDRFSGSKSGTSASLAISGLQSEDEADYYCAAWDDSLNGVVF

GGGTKLTVLGQPKAAPS
```

```
MISIIR scFv nucleotide sequence: (SEQ ID NO: 16):
GCCCAGGTGCAGCTGGTGCAGTCTGGAACTGAGGTGAAGAGGCCTGGGG

CCTCAGTGAAGATCTCCTGCAGGGCTACTGGTTACACCTTTAGTGATTA

TGGTATCAGTTGGATGCGACAGGCCCCTGGACAAGGGCTTGAGTGGATG

GGATGGATCAGCGCTTACAATGGTAACACAAACTATGCACAGAAGCTCC

AGGGCAGAGTCACCATGACCACAGACACGTCCACGAGCACAGCCTACAT

GGAGCTGAGGAGCCTCAGATATGACGACACGGCCGTATATTACTGTGCG

AGAGATGGGAGGCGTGGTTCGGGTATTTACTGGGGTGTGTATTATTACA

ACGGTATGGACGTCTGGGGCCAAGGGACCACGGTCACCGTCTCCTCAGG

TGGCGGCGGTTCCGGAGGTGGTGGTTCTGGCGGTGGTGGCAGTCAGCCT

GTGCTGACTCAGCCACCCTCAGCGTCTGGGACCCCCGGGCAGAGGGTCA

CCATCTCTTGTTCTGGAAGCAGGTCCAACATCGGAAGGAATACCGTAAA

CTGGTATCAGCAGGTCCCAGGAATGGCCCCCAAACTCCTCATCTATAGT

AATAATCAGCGGCCCTCAGGGGTCCCTGACCGATTCTCTGGCTCCAAGT

CTGGCACCTCAGCCTCCCTGGCCATCAGTGGGCTCCAGTCTGAGGATGA

GGCTGATTATTACTGTGCAGCATGGGATGACAGTCTGAATGGTGTGGTA

TTCGGCGGAGGGACCAAGCTGACCGTCCTAGGTCAGCCCAAGGCCGCCC

CCTCG
```

Transmembrane Domain

CARs of the present invention may comprise a transmembrane domain that connects the antigen binding domain of the CAR to the intracellular domain of the CAR. The transmembrane domain of a subject CAR is a region that is capable of spanning the plasma membrane of a cell (e.g., an immune cell or precursor thereof). The transmembrane domain is for insertion into a cell membrane, e.g., a eukaryotic cell membrane. In some embodiments, the transmembrane domain is interposed between the antigen binding domain and the intracellular domain of a CAR.

In some embodiments, the transmembrane domain is naturally associated with one or more of the domains in the CAR. In some embodiments, the transmembrane domain can be selected or modified by one or more amino acid substitutions to avoid binding of such domains to the transmembrane domains of the same or different surface membrane proteins, to minimize interactions with other members of the receptor complex.

The transmembrane domain may be derived either from a natural or a synthetic source. Where the source is natural, the domain may be derived from any membrane-bound or transmembrane protein, e.g., a Type I transmembrane protein. Where the source is synthetic, the transmembrane domain may be any artificial sequence that facilitates insertion of the CAR into a cell membrane, e.g., an artificial hydrophobic sequence. Examples of the transmembrane domain of particular use in this invention include, without limitation, transmembrane domains derived from (i.e. comprise at least the transmembrane region(s) of) the alpha, beta or zeta chain of the T cell receptor, CD28, CD3 epsilon, CD45, CD4, CD5, CD7, CD8, CD9, CD16, CD22, CD33, CD37, CD64, CD80, CD86, CD134 (OX-40), CD137 (4-1BB), CD154 (CD40L), Toll-like receptor 1 (TLR1), TLR2, TLR3, TLR4, TLR5, TLR6, TLR7, TLR8, and TLR9. In some embodiments, the transmembrane domain may be synthetic, in which case it will comprise predominantly hydrophobic residues such as leucine and valine. Preferably a triplet of phenylalanine, tryptophan and valine will be found at each end of a synthetic transmembrane domain.

The transmembrane domains described herein can be combined with any of the antigen binding domains described herein, any of the intracellular domains described herein, or any of the other domains described herein that may be included in a subject CAR.

In certain embodiments, the transmembrane domain of the CAR comprises a CD8 alpha domain.

In certain embodiments, the transmembrane domain of the CAR comprises the amino acid sequence set forth in SEQ ID NO: 17. In certain embodiments, the transmembrane domain of the CAR is encoded by the nucleotide sequence set forth in SEQ ID NO: 18.

Tolerable variations of the transmembrane domain will be known to those of skill in the art. For example, in some embodiments the transmembrane domain comprises an amino acid sequence that has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity to the amino acid sequences set forth in SEQ ID NO: 17. For example, in some embodiments the transmembrane domain is encoded by a nucleic acid sequence that has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity to any of the nucleic acid sequences set forth in SEQ ID NO: 18.

```
CD8a transmembrane domain amino acid sequence
(SEQ ID NO: 17):
IYIWAPLAGTCGVLLLSLVITLYC CD8a transmembrane domain nucleotide sequence:
(SEQ ID NO: 18):
Atctacatctgggcgcccttggccgggacttgtggg gtccttctcctgtcactggttatcaccctttactgc
```

In some embodiments, the transmembrane domain further comprises a hinge region. A subject CAR of the present invention may also include a hinge region. The hinge region of the CAR is a hydrophilic region which is located between the antigen binding domain and the transmembrane domain. In some embodiments, this domain facilitates proper protein folding for the CAR. The hinge region is an optional component for the CAR. The hinge region may include a domain selected from Fc fragments of antibodies, hinge regions of antibodies, CH2 regions of antibodies, CH3 regions of antibodies, artificial hinge sequences or combinations thereof. Examples of hinge regions include, without limitation, a CD8a hinge, artificial hinges made of polypeptides which may be as small as, three glycines (Gly), as well as CH1 and CH3 domains of IgGs (such as human IgG4).

In some embodiments, a subject CAR of the present disclosure includes a hinge region that connects the antigen binding domain with the transmembrane domain, which, in turn, connects to the intracellular domain. The hinge region is preferably capable of supporting the antigen binding domain to recognize and bind to the target antigen on the target cells (see, e.g., Hudecek et al., *Cancer Immunol. Res.* (2015) 3(2): 125-135). In some embodiments, the hinge region is a flexible domain, thus allowing the antigen binding domain to have a structure to optimally recognize the specific structure and density of the target antigens on a cell such as tumor cell (Hudecek et al., supra). The flexibility of the hinge region permits the hinge region to adopt many different conformations.

In some embodiments, the hinge region is an immunoglobulin heavy chain hinge region. In some embodiments, the hinge region is a hinge region polypeptide derived from a receptor (e.g., a CD8-derived hinge region).

The hinge region can have a length of from about 4 amino acids to about 50 amino acids, e.g., from about 4 aa to about 10 aa, from about 10 aa to about 15 aa, from about 15 aa to about 20 aa, from about 20 aa to about 25 aa, from about 25 aa to about 30 aa, from about 30 aa to about 40 aa, or from about 40 aa to about 50 aa. In some embodiments, the hinge region can have a length of greater than 5 aa, greater than 10 aa, greater than 15 aa, greater than 20 aa, greater than 25 aa, greater than 30 aa, greater than 35 aa, greater than 40 aa, greater than 45 aa, greater than 50 aa, greater than 55 aa, or more.

Suitable hinge regions can be readily selected and can be of any of a number of suitable lengths, such as from 1 amino acid (e.g., Gly) to 20 amino acids, from 2 amino acids to 15 amino acids, from 3 amino acids to 12 amino acids, including 4 amino acids to 10 amino acids, 5 amino acids to 9 amino acids, 6 amino acids to 8 amino acids, or 7 amino acids to 8 amino acids, and can be 1, 2, 3, 4, 5, 6, or 7 amino acids. Suitable hinge regions can have a length of greater than 20 amino acids (e.g., 30, 40, 50, 60 or more amino acids).

For example, hinge regions include glycine polymers $(G)_n$, glycine-serine polymers (including, for example, $(GS)_n$, $(GSGGS)_n$ (SEQ ID NO:3) and $(GGGS)_n$ (SEQ ID NO:4), where n is an integer of at least one), glycine-alanine polymers, alanine-serine polymers, and other flexible linkers known in the art. Glycine and glycine-serine polymers can be used; both Gly and Ser are relatively unstructured, and therefore can serve as a neutral tether between components. Glycine polymers can be used; glycine accesses significantly more phi-psi space than even alanine, and is much less restricted than residues with longer side chains (see, e.g., Scheraga, *Rev. Computational. Chem.* (1992) 2: 73-142). Exemplary hinge regions can comprise amino acid sequences including, but not limited to, GGSG (SEQ ID NO:6), GGSGG (SEQ ID NO:7), GSGSG (SEQ ID NO:8), GSGGG (SEQ ID NO:9), GGGSG (SEQ ID NO:10), GSSSG (SEQ ID NO: 11), and the like.

In some embodiments, the hinge region is an immunoglobulin heavy chain hinge region. Immunoglobulin hinge region amino acid sequences are known in the art; see, e.g., Tan et al., *Proc. Natl. Acad. Sci. USA* (1990) 87(1):162-166; and Huck et al., *Nucleic Acid Res.* (1986) 14(4): 1779-1789. As non-limiting examples, an immunoglobulin hinge region can include one of the following amino acid sequences: DKTHT (SEQ ID NO:23); CPPC (SEQ ID NO:24); CPEPKSCDTPPPCPR (SEQ ID NO:25) (see, e.g., Glaser et al., *J. Biol. Chem.* (2005) 280:41494-41503); ELKTPLGDTTHT (SEQ ID NO:26); KSCDKTHTCP (SEQ ID NO:27); KCCVDCP (SEQ ID NO:28); KYGPPCP (SEQ ID NO:29); EPKSCDKTHTCPPCP (SEQ ID NO:30) (human IgG1 hinge); ERKCCVECPPCP (SEQ ID NO:31) (human IgG2 hinge); ELKTPLGDTTHTCPRCP (SEQ ID NO:32) (human IgG3 hinge); SPNMVPHAHHAQ (SEQ ID NO:33) (human IgG4 hinge); and the like.

The hinge region can comprise an amino acid sequence of a human IgG1, IgG2, IgG3, or IgG4, hinge region. In one embodiment, the hinge region can include one or more amino acid substitutions and/or insertions and/or deletions compared to a wild-type (naturally-occurring) hinge region. For example, His229 of human IgG1 hinge can be substituted with Tyr, so that the hinge region comprises the sequence EPKSCDKTYTCPPCP (SEQ ID NO:34); see, e.g., Yan et al., *J. Biol. Chem.* (2012) 287: 5891-5897. In one embodiment, the hinge region can comprise an amino acid sequence derived from human CD8, or a variant thereof.

Intracellular Domain

A subject CAR of the present invention also includes an intracellular domain. The terms "intracellular domain" and "intracellular signaling domain" are used interchangeably herein. The intracellular domain of the CAR is responsible for activation of at least one of the effector functions of the cell in which the CAR is expressed (e.g., immune cell). The intracellular domain transduces the effector function signal and directs the cell (e.g., immune cell) to perform its specialized function, e.g., harming and/or destroying a target cell.

Examples of an intracellular domain for use in the invention include, but are not limited to, the cytoplasmic portion of a surface receptor, co-stimulatory molecule, and any molecule that acts in concert to initiate signal transduction in the T cell, as well as any derivative or variant of these elements and any synthetic sequence that has the same functional capability.

Examples of the intracellular domain include, without limitation, the ζ chain of the T cell receptor complex or any of its homologs, e.g., η chain, FcsRIγ and β chains, MB 1 (IgA) chain, B29 (Ig) chain, etc., human CD3 zeta chain, CD3 polypeptides (Δ, δ and ε), syk family tyrosine kinases (Syk, ZAP 70, etc.), src family tyrosine kinases (Lck, Fyn, Lyn, etc.), and other molecules involved in T cell transduction, such as CD2, CD5 and CD28. In one embodiment, the intracellular signaling domain may be human CD3 zeta chain, FcγRIII, FcsRI, cytoplasmic tails of Fc receptors, an immunoreceptor tyrosine-based activation motif (ITAM) bearing cytoplasmic receptors, and combinations thereof.

In one embodiment, the intracellular domain of the CAR includes any portion of one or more co-stimulatory molecules, such as at least one signaling domain from CD2, CD3, CD8, CD27, CD28, ICOS, 4-1BB, PD-1, any derivative or variant thereof, any synthetic sequence thereof that has the same functional capability, and any combination thereof.

Other examples of the intracellular domain include a fragment or domain from one or more molecules or receptors including, but not limited to, TCR, CD3 zeta, CD3 gamma, CD3 delta, CD3 epsilon, CD86, common FcR gamma, FcR beta (Fc Epsilon RIb), CD79a, CD79b, Fcgamma RIIa, DAP10, DAP12, T cell receptor (TCR), CD8, CD27, CD28, 4-1BB (CD137), OX9, OX40, CD30, CD40, PD-1, ICOS, a KIR family protein, lymphocyte function-associated antigen-1 (LFA-1), CD2, CD7, LIGHT, NKG2C, B7-H3, a ligand that specifically binds with CD83, CDS, ICAM-1, GITR, BAFFR, HVEM (LIGHTR), SLAMF7, NKp80 (KLRF1), CD127, CD160, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, CD1 id, ITGAE, CD103, ITGAL, CD11a, LFA-1, ITGAM, CDlib, ITGAX, CD1 Ic, ITGB1, CD29, ITGB2, CD18, LFA-1, ITGB7, TNFR2, TRANCE/RANKL, DNAM1 (CD226), SLAMF4 (CD244, 2B4), CD84, CD96 (Tactile), CEACAM1, CRT AM, Ly9 (CD229), CD160 (BY55), PSGL1, CD100 (SEMA4D), CD69, SLAMF6 (NTB-A, Ly108), SLAM (SLAMFI, CD150, IPO-3), BLAME (SLAMF8), SELPLG (CD162), LTBR, LAT, GADS, SLP-76, PAG/Cbp, NKp44, NKp30, NKp46, NKG2D, Toll-like receptor 1 (TLR1), TLR2, TLR3, TLR4, TLR5, TLR6, TLR7, TLR8, TLR9, other co-stimulatory molecules described herein, any derivative, variant, or fragment thereof, any synthetic sequence of a co-stimulatory molecule that has the same functional capability, and any combination thereof.

Additional examples of intracellular domains include, without limitation, intracellular signaling domains of several types of various other immune signaling receptors, including, but not limited to, first, second, and third generation T cell signaling proteins including CD3, B7 family costimulatory, and Tumor Necrosis Factor Receptor (TNFR) superfamily receptors (see, e.g., Park and Brentjens, J. Clin. Oncol. (2015) 33(6): 651-653). Additionally, intracellular signaling domains may include signaling domains used by NK and NKT cells (see, e.g., Hermanson and Kaufman, Front. Immunol. (2015) 6: 195) such as signaling domains of NKp30 (B7-H6) (see, e.g., Zhang et al., J. Immunol. (2012) 189(5): 2290-2299), and DAP 12 (see, e.g., Topfer et al., J. Immunol. (2015) 194(7): 3201-3212), NKG2D, NKp44, NKp46, DAP10, and CD3z.

Intracellular domains suitable for use in a subject CAR of the present invention include any desired signaling domain that provides a distinct and detectable signal (e.g., increased production of one or more cytokines by the cell; change in transcription of a target gene; change in activity of a protein; change in cell behavior, e.g., cell death; cellular proliferation; cellular differentiation; cell survival; modulation of cellular signaling responses; etc.) in response to activation of the CAR (i.e., activated by antigen and dimerizing agent). In some embodiments, the intracellular signaling domain includes at least one (e.g., one, two, three, four, five, six, etc.) ITAM motifs as described below. In some embodiments, the intracellular signaling domain includes DAP10/CD28 type signaling chains. In some embodiments, the intracellular signaling domain is not covalently attached to the membrane bound CAR, but is instead diffused in the cytoplasm.

Intracellular signaling domains suitable for use in a subject CAR of the present invention include immunoreceptor tyrosine-based activation motif (ITAM)-containing intracellular signaling polypeptides. In some embodiments, an ITAM motif is repeated twice in an intracellular signaling domain, where the first and second instances of the ITAM motif are separated from one another by 6 to 8 amino acids. In one embodiment, the intracellular signaling domain of a subject CAR comprises 3 ITAM motifs.

In some embodiments, intracellular signaling domains includes the signaling domains of human immunoglobulin receptors that contain immunoreceptor tyrosine based activation motifs (ITAMs) such as, but not limited to, Fcgam-maRI, FcgammaRIIA, FcgammaRIIC, FcgammaRIIIA, FcRL5 (see, e.g., Gillis et al., Front. Immunol. (2014) 5:254).

A suitable intracellular signaling domain can be an ITAM motif-containing portion that is derived from a polypeptide that contains an ITAM motif. For example, a suitable intracellular signaling domain can be an ITAM motif-containing domain from any ITAM motif-containing protein. Thus, a suitable intracellular signaling domain need not contain the entire sequence of the entire protein from which it is derived. Examples of suitable ITAM motif-containing polypeptides include, but are not limited to: DAP12, FCERIG (Fc epsilon receptor I gamma chain), CD3D (CD3 delta), CD3E (CD3 epsilon), CD3G (CD3 gamma), CD3Z (CD3 zeta), and CD79A (antigen receptor complex-associated protein alpha chain).

In one embodiment, the intracellular signaling domain is derived from DAP12 (also known as TYROBP; TYRO protein tyrosine kinase binding protein; KARAP; PLOSL; DNAX-activation protein 12; KAR-associated protein; TYRO protein tyrosine kinase-binding protein; killer activating receptor associated protein; killer-activating receptor-associated protein; etc.). In one embodiment, the intracellular signaling domain is derived from FCERIG (also known as FCRG; Fc epsilon receptor I gamma chain; Fc receptor gamma-chain; fc-epsilon RI-gamma; fcRgamma; fceR1 gamma; high affinity immunoglobulin epsilon receptor subunit gamma; immunoglobulin E receptor, high affinity, gamma chain; etc.). In one embodiment, the intracellular signaling domain is derived from T-cell surface glycoprotein CD3 delta chain (also known as CD3D; CD3-DELTA; T3D; CD3 antigen, delta subunit; CD3 delta; CD3d antigen, delta polypeptide (TiT3 complex); OKT3, delta chain; T-cell receptor T3 delta chain; T-cell surface glycoprotein CD3 delta chain; etc.). In one embodiment, the intracellular signaling domain is derived from T-cell surface glycoprotein CD3 epsilon chain (also known as CD3e, T-cell surface antigen T3/Leu-4 epsilon chain, T-cell surface glycoprotein CD3 epsilon chain, AI504783, CD3, CD3epsilon, T3e, etc.). In one embodiment, the intracellular signaling domain is derived from T-cell surface glycoprotein CD3 gamma chain (also known as CD3G, T-cell receptor T3 gamma chain, CD3-GAMMA, T3G, gamma polypeptide (TiT3 complex), etc.). In one embodiment, the intracellular signaling domain is derived from T-cell surface glycoprotein CD3 zeta chain (also known as CD3Z, T-cell receptor T3 zeta chain, CD247, CD3-ZETA, CD3H, CD3Q, T3Z, TCRZ, etc.). In one embodiment, the intracellular signaling domain is derived from CD79A (also known as B-cell antigen receptor complex-associated protein alpha chain; CD79a antigen (immunoglobulin-associated alpha); MB-1 membrane glycoprotein; ig-alpha; membrane-bound immunoglobulin-associated protein; surface IgM-associated protein; etc.). In one embodiment, an intracellular signaling domain suitable for use in an FN3 CAR of the present disclosure includes a DAP10/CD28 type signaling chain. In one embodiment, an intracellular signaling domain suitable for use in an FN3 CAR of the present disclosure includes a ZAP70 polypeptide. In some embodiments, the intracellular signaling domain includes a cytoplasmic signaling domain of TCR zeta, FcR gamma, FcR beta, CD3 gamma, CD3 delta, CD3 epsilon, CD5, CD22, CD79a, CD79b, or CD66d. In one embodiment, the intracellular signaling domain in the CAR includes a cytoplasmic signaling domain of human CD3 zeta.

While usually the entire intracellular signaling domain can be employed, in many cases it is not necessary to use the entire chain. To the extent that a truncated portion of the intracellular signaling domain is used, such truncated portion may be used in place of the intact chain as long as it transduces the effector function signal. The intracellular signaling domain includes any truncated portion of the intracellular signaling domain sufficient to transduce the effector function signal.

The intracellular signaling domains described herein can be combined with any of the antigen binding domains described herein, any of the transmembrane domains described herein, or any of the other domains described herein that may be included in the CAR.

In certain exemplary embodiments, the CAR comprises an intracellular domain comprising CD27. In certain exemplary embodiments, the CAR comprises an intracellular domain comprising CD27 and CD3 zeta.

In certain embodiments, the intracellular domain of the CAR comprises the amino acid sequence set forth in SEQ ID NO: 19. In certain embodiments, the intracellular domain of the CAR comprises the amino acid sequence set forth in SEQ ID NO: 21. In certain embodiments, the intracellular domain of the CAR comprises the amino acid sequences set forth in SEQ ID NO: 19 and SEQ ID NO: 21. In certain embodiments, the intracellular domain of the CAR is encoded by the nucleotide sequence set forth in SEQ ID NO: 20. In certain embodiments, the intracellular domain of the CAR is encoded by the nucleotide sequence set forth in SEQ ID NO: 22. In certain embodiments, the intracellular domain of the CAR is encoded by the nucleotide sequences set forth in SEQ ID NO: 20 and SEQ ID NO: 22.

Tolerable variations of the intracellular domain will be known to those of skill in the art. For example, in some embodiments the transmembrane domain comprises an amino acid sequence that has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity to the amino acid sequences set forth in SEQ ID NO: 19 and/or SEQ ID NO: 21. For example, in some embodiments the transmembrane domain is encoded by a nucleic acid sequence that has at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% sequence identity to any of the nucleic acid sequences set forth in SEQ ID NO: 20 and/or SEQ ID NO: 22.

```
CD27 intracellular domain amino acid
sequence (SEQ ID NO: 19):
QRRKYRSNKGESPVEPAEPCRYSCPREEEGSTIPIQEDY

RKPEPACSP

CP27 intracellular domain nucleotide
sequence (SEQ ID NO: 20):
caacgaaggaaatatagatcaaacaaaggagaaagtcctg tggagcctgcagagccttgtcgttacagctgccccaggga ggaggagggcagcaccatccccatccaggaggattaccga aaaccggagcctgcctgctccccc
```

-continued

```
CD3 zeta intracellular domain amino acid
sequence (SEQ ID NO: 21):
RVKFSRSADAPAYQQGQNQLYNELNLGRREEYDVLDKRRG

RDPEMGGKPRRKNPQEGLYNELQKDKMAEAYSEIGMKGERR

RGKGHDGLYQGLSTATKDTYDALHMQALPPR

CD3 zeta intracellular domain nucleotide
sequence (SEQ ID NO: 22):
agagtgaagttcagcaggagcgcagacgcccccgcgtac cagcagggccagaaccagctctataacgagctcaatcta ggacgaagagaggagtacgatgttttggacaagagacgt ggccgggaccctgagatggggggaaagccgagaaggaag aaccctcaggaaggcctgtacaatgaactgcagaaagat aagatggcggaggcctacagtgagattgggatgaaagg cgagcgccggaggggcaaggggcacgatggcctttacca gggtctcagtacagccaccaaggacacctacgacgccct tcacatgcaggccctgcccctcgctaa
```

In certain embodiments, the CAR comprises an antigen binding domain having affinity for MISIIR, a CD8α hinge domain, a CD8α transmembrane domain, a CD27 intracellular domain, and a CD3 zeta intracellular domain.

C. Modified Immune Cells

The present invention provides compositions and methods for modified immune cells or precursors thereof (e.g., modified T cells) comprising a chimeric antigen receptor (CAR) specific for Müllerian inhibiting substance type 2 receptor (MISIIR). Also provided are modified immune cells or precursor cell thereof comprising a nucleic acid encoding a CAR specific for Müllerian inhibiting substance type 2 receptor (MISIIR).

In some embodiments, the cells, compositions, and methods provide for the modified immune cells (e.g. CAR T cells) to be adoptively transferred. In some embodiments, the modifications are performed ex vivo on primary cells, such as primary immune cells (e.g. T cells) from a subject. In some aspects, methods of producing or generating such modified T cells include introducing into a population of cells containing immune cells (e.g. T cells) one or more nucleic acids encoding a recombinant receptor (e.g. exogenous CAR). As used herein, the term "introducing" encompasses a variety of methods of introducing DNA into a cell, either in vitro or in vivo, such methods including transformation, transduction, transfection (e.g. electroporation), and infection. Vectors are useful for introducing DNA encoding molecules into cells. Possible vectors include plasmid vectors and viral vectors. Viral vectors include retroviral vectors, lentiviral vectors, or other vectors such as adenoviral vectors or adeno-associated vectors.

The population of cells containing T cells can be cells that have been obtained from a subject, such as obtained from a peripheral blood mononuclear cells (PBMC) sample, an unfractionated T cell sample, a lymphocyte sample, a white blood cell sample, an apheresis product, or a leukapheresis product. In some embodiments, T cells can be separated or selected to enrich T cells in the population using positive or negative selection and enrichment methods. In some embodiments, the population contains CD4+, CD8+ or CD4+ and CD8+ T cells.

D. Methods of Treatment

The modified cells (e.g., CAR T cells) described herein may be included in a composition for immunotherapy. The composition may include a pharmaceutical composition and further include a pharmaceutically acceptable carrier. A therapeutically effective amount of the pharmaceutical composition comprising the modified T cells may be administered.

In one aspect, the invention includes a method for adoptive cell transfer therapy comprising administering to a subject in need thereof a modified T cell of the present invention. In another aspect, the invention includes a method of treating a disease or condition in a subject comprising administering to a subject in need thereof a population of modified T cells. In certain embodiments, the disease to be treated is cancer.

Methods for administration of immune cells for adoptive cell therapy are known and may be used in connection with the provided methods and compositions. For example, adoptive T cell therapy methods are described, e.g., in US Patent Application Publication No. 2003/0170238 to Gruenberg et al; U.S. Pat. No. 4,690,915 to Rosenberg; Rosenberg (2011) Nat Rev Clin Oncol. 8(10):577-85). See, e.g., Themeli et al. (2013) Nat Biotechnol. 31(10): 928-933; Tsukahara et al. (2013) Biochem Biophys Res Commun 438(1): 84-9; Davila et al. (2013) PLoS ONE 8(4): e61338. In some embodiments, the cell therapy, e.g., adoptive T cell therapy is carried out by autologous transfer, in which the cells are isolated and/or otherwise prepared from the subject who is to receive the cell therapy, or from a sample derived from such a subject. Thus, in some aspects, the cells are derived from a subject, e.g., patient, in need of a treatment and the cells, following isolation and processing are administered to the same subject.

In some embodiments, the cell therapy, e.g., adoptive T cell therapy, is carried out by allogeneic transfer, in which the cells are isolated and/or otherwise prepared from a subject other than a subject who is to receive or who ultimately receives the cell therapy, e.g., a first subject. In such embodiments, the cells then are administered to a different subject, e.g., a second subject, of the same species. In some embodiments, the first and second subjects are genetically identical. In some embodiments, the first and second subjects are genetically similar. In some embodiments, the second subject expresses the same HLA class or supertype as the first subject.

In some embodiments, the subject has been treated with a therapeutic agent targeting the disease or condition, e.g. the tumor, prior to administration of the cells or composition containing the cells. In some aspects, the subject is refractory or non-responsive to the other therapeutic agent. In some embodiments, the subject has persistent or relapsed disease, e.g., following treatment with another therapeutic intervention, including chemotherapy, radiation, and/or hematopoietic stem cell transplantation (HSCT), e.g., allogenic HSCT. In some embodiments, the administration effectively treats the subject despite the subject having become resistant to another therapy.

In some embodiments, the subject is responsive to the other therapeutic agent, and treatment with the therapeutic agent reduces disease burden. In some aspects, the subject is initially responsive to the therapeutic agent, but exhibits a relapse of the disease or condition over time. In some embodiments, the subject has not relapsed. In some such embodiments, the subject is determined to be at risk for relapse, such as at a high risk of relapse, and thus the cells are administered prophylactically, e.g., to reduce the likelihood of or prevent relapse. In some aspects, the subject has not received prior treatment with another therapeutic agent.

The modified immune cells of the present invention can be administered to an animal, preferably a mammal, even more preferably a human, to treat a cancer. In addition, the cells of the present invention can be used for the treatment of any condition related to a cancer, especially a cell-mediated immune response against a tumor cell(s), where it is desirable to treat or alleviate the disease. The types of cancers to be treated with the modified cells or pharmaceutical compositions of the invention include, carcinoma, blastoma, and sarcoma, and certain leukemia or lymphoid malignancies, benign and malignant tumors, and malignancies e.g., sarcomas, carcinomas, and melanomas. Other exemplary cancers include but are not limited breast cancer, prostate cancer, ovarian cancer, cervical cancer, skin cancer, pancreatic cancer, colorectal cancer, renal cancer, liver cancer, brain cancer, lymphoma, leukemia, lung cancer, thyroid cancer, and the like. The cancers may be non-solid tumors (such as hematological tumors) or solid tumors. Adult tumors/cancers and pediatric tumors/cancers are also included. In one embodiment, the cancer is a solid tumor or a hematological tumor. In one embodiment, the cancer is a carcinoma. In one embodiment, the cancer is a sarcoma. In one embodiment, the cancer is a leukemia. In one embodiment the cancer is a solid tumor. In one embodiment, the cancer is ovarian cancer. In one embodiment, the cancer is endometrial cancer Solid tumors are abnormal masses of tissue that usually do not contain cysts or liquid areas. Solid tumors can be benign or malignant. Different types of solid tumors are named for the type of cells that form them (such as sarcomas, carcinomas, and lymphomas). Examples of solid tumors, such as sarcomas and carcinomas, include fibrosarcoma, myxosarcoma, liposarcoma, chondrosarcoma, osteosarcoma, and other sarcomas, synovioma, mesothelioma, Ewing's tumor, leiomyosarcoma, rhabdomyosarcoma, colon carcinoma, lymphoid malignancy, pancreatic cancer, breast cancer, lung cancers, ovarian cancer, prostate cancer, hepatocellular carcinoma, squamous cell carcinoma, basal cell carcinoma, adenocarcinoma, sweat gland carcinoma, medullary thyroid carcinoma, papillary thyroid carcinoma, pheochromocytomas sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, seminoma, bladder carcinoma, melanoma, and CNS tumors (such as a glioma (such as brainstem glioma and mixed gliomas), glioblastoma (also known as glioblastoma multiforme) astrocytoma, CNS lymphoma, germinoma, medulloblastoma, Schwannoma craniopharyogioma, ependymoma, pinealoma, hemangioblastoma, acoustic neuroma, oligodendroglioma, menangioma, neuroblastoma, retinoblastoma and brain metastases).

Carcinomas that can be amenable to therapy by a method disclosed herein include, but are not limited to, esophageal carcinoma, hepatocellular carcinoma, basal cell carcinoma (a form of skin cancer), squamous cell carcinoma (various tissues), bladder carcinoma, including transitional cell carcinoma (a malignant neoplasm of the bladder), bronchogenic carcinoma, colon carcinoma, colorectal carcinoma, gastric carcinoma, lung carcinoma, including small cell carcinoma and non-small cell carcinoma of the lung, adrenocortical carcinoma, thyroid carcinoma, pancreatic carcinoma, breast carcinoma, ovarian carcinoma, prostate carcinoma, adenocarcinoma, sweat gland carcinoma, sebaceous gland carcinoma, papillary carcinoma, papillary adenocarcinoma, cystadenocarcinoma, medullary carcinoma, renal cell carcinoma, ductal carcinoma in situ or bile duct carcinoma, choriocarcinoma, seminoma, embryonal carcinoma, Wilm's tumor, cervical carcinoma, uterine carcinoma, testicular carcinoma, osteogenic carcinoma, epithelial carcinoma, and nasopharyngeal carcinoma, ovarian cancer, endometrial cancer, uterine sarcoma, cervical carcinoma, breast cancer, lung cancer, prostate cancer, ocular melanoma, and any MISIR-expressing tumor.

Sarcomas that can be amenable to therapy by a method disclosed herein include, but are not limited to, fibrosarcoma, myxosarcoma, liposarcoma, chondrosarcoma, chordoma, osteogenic sarcoma, osteosarcoma, angiosarcoma, endotheliosarcoma, lymphangiosarcoma, lymphangioendotheliosarcoma, synovioma, mesothelioma, Ewing's sarcoma, leiomyosarcoma, rhabdomyosarcoma, and other soft tissue sarcomas.

In certain exemplary embodiments, the modified immune cells of the invention are used to treat a myeloma, or a condition related to myeloma. Examples of myeloma or conditions related thereto include, without limitation, light chain myeloma, non-secretory myeloma, monoclonal gammopathy of undertermined significance (MGUS), plasmacytoma (e.g., solitary, multiple solitary, extramedullary plasmacytoma), amyloidosis, and multiple myeloma. In one embodiment, a method of the present disclosure is used to treat multiple myeloma. In one embodiment, a method of the present disclosure is used to treat refractory myeloma. In one embodiment, a method of the present disclosure is used to treat relapsed myeloma.

In certain exemplary embodiments, the modified immune cells of the invention are used to treat a melanoma, or a condition related to melanoma. Examples of melanoma or conditions related thereto include, without limitation, superficial spreading melanoma, nodular melanoma, lentigo maligna melanoma, acral lentiginous melanoma, amelanotic melanoma, or melanoma of the skin (e.g., cutaneous, eye, vulva, vagina, rectum melanoma). In one embodiment, a method of the present disclosure is used to treat cutaneous melanoma. In one embodiment, a method of the present disclosure is used to treat refractory melanoma. In one embodiment, a method of the present disclosure is used to treat relapsed melanoma.

In yet other exemplary embodiments, the modified immune cells of the invention are used to treat a sarcoma, or a condition related to sarcoma. Examples of sarcoma or conditions related thereto include, without limitation, angiosarcoma, chondrosarcoma, Ewing's sarcoma, fibrosarcoma, gastrointestinal stromal tumor, leiomyosarcoma, liposarcoma, malignant peripheral nerve sheath tumor, osteosarcoma, pleomorphic sarcoma, rhabdomyosarcoma, and synovial sarcoma. In one embodiment, a method of the present disclosure is used to treat synovial sarcoma. In one embodiment, a method of the present disclosure is used to treat liposarcoma such as myxoid/round cell liposarcoma, differentiated/dedifferentiated liposarcoma, and pleomorphic liposarcoma. In one embodiment, a method of the present disclosure is used to treat myxoid/round cell liposarcoma. In one embodiment, a method of the present disclosure is used to treat a refractory sarcoma. In one embodiment, a method of the present disclosure is used to treat a relapsed sarcoma.

The cells of the invention to be administered may be autologous, with respect to the subject undergoing therapy.

The administration of the cells of the invention may be carried out in any convenient manner known to those of skill in the art. The cells of the present invention may be administered to a subject by aerosol inhalation, injection, ingestion, transfusion, implantation or transplantation. The compositions described herein may be administered to a patient transarterially, subcutaneously, intradermally, intra- tumorally, intranodally, intramedullary, intramuscularly, by intravenous (i.v.) injection, or intraperitoneally. In other instances, the cells of the invention are injected directly into a site of inflammation in the subject, a local disease site in the subject, alymph node, an organ, a tumor, and the like.

In some embodiments, the cells are administered at a desired dosage, which in some aspects includes a desired dose or number of cells or cell type(s) and/or a desired ratio of cell types. Thus, the dosage of cells in some embodiments is based on a total number of cells (or number per kg body weight) and a desired ratio of the individual populations or sub-types, such as the CD4+ to CD8+ ratio. In some embodiments, the dosage of cells is based on a desired total number (or number per kg of body weight) of cells in the individual populations or of individual cell types. In some embodiments, the dosage is based on a combination of such features, such as a desired number of total cells, desired ratio, and desired total number of cells in the individual populations.

In some embodiments, the populations or sub-types of cells, such as $CD8^+$ and $CD4^+$ T cells, are administered at or within a tolerated difference of a desired dose of total cells, such as a desired dose of T cells. In some aspects, the desired dose is a desired number of cells or a desired number of cells per unit of body weight of the subject to whom the cells are administered, e.g., cells/kg. In some aspects, the desired dose is at or above a minimum number of cells or minimum number of cells per unit of body weight. In some aspects, among the total cells, administered at the desired dose, the individual populations or sub-types are present at or near a desired output ratio (such as $CD4^+$ to $CD8^+$ ratio), e.g., within a certain tolerated difference or error of such a ratio.

In some embodiments, the cells are administered at or within a tolerated difference of a desired dose of one or more of the individual populations or sub-types of cells, such as a desired dose of CD4+ cells and/or a desired dose of CD8+ cells. In some aspects, the desired dose is a desired number of cells of the sub-type or population, or a desired number of such cells per unit of body weight of the subject to whom the cells are administered, e.g., cells/kg. In some aspects, the desired dose is at or above a minimum number of cells of the population or subtype, or minimum number of cells of the population or sub-type per unit of body weight. Thus, in some embodiments, the dosage is based on a desired fixed dose of total cells and a desired ratio, and/or based on a desired fixed dose of one or more, e.g., each, of the indi- vidual sub-types or sub-populations. Thus, in some embodi- ments, the dosage is based on a desired fixed or minimum dose of T cells and a desired ratio of $CD4^+$ to $CD8^+$ cells, and/or is based on a desired fixed or minimum dose of $CD4^+$ and/or $CD8^+$ cells.

In certain embodiments, the cells, or individual popula- tions of sub-types of cells, are administered to the subject at a range of about one million to about 100 billion cells, such as, e.g., 1 million to about 50 billion cells (e.g., about 5 million cells, about 25 million cells, about 500 million cells, about 1 billion cells, about 5 billion cells, about 20 billion cells, about 30 billion cells, about 40 billion cells, or a range defined by any two of the foregoing values), such as about 10 million to about 100 billion cells (e.g., about 20 million cells, about 30 million cells, about 40 million cells, about 60 million cells, about 70 million cells, about 80 million cells, about 90 million cells, about 10 billion cells, about 25 billion cells, about 50 billion cells, about 75 billion cells, about 90 billion cells, or a range defined by any two of the foregoing values), and in some cases about 100 million cells to about 50 billion cells (e.g., about 120 million cells, about 250 million cells, about 350 million cells, about 450 million cells, about 650 million cells, about 800 million cells, about 900 million cells, about 3 billion cells, about 30 billion cells, about 45 billion cells) or any value in between these ranges.

In some embodiments, the dose of total cells and/or dose of individual sub-populations of cells is within a range of between at or about $1\times10^5$ cells/kg to about $1\times10^{11}$ cells/kg $10^4$ and at or about $10^{11}$ cells/kilograms (kg) body weight, such as between $10^5$ and $10^6$ cells/kg body weight, for example, at or about $1\times10^5$ cells/kg, $1.5\times10^5$ cells/kg, $2\times10^5$ cells/kg, or $1\times10^6$ cells/kg body weight. For example, in some embodiments, the cells are administered at, or within a certain range of error of, between at or about $10^4$ and at or about $10^9$ T cells/kilograms (kg) body weight, such as between $10^5$ and $10^6$ T cells/kg body weight, for example, at or about $1\times10^5$ T cells/kg, $1.5\times10^5$ T cells/kg, $2\times10^5$ T cells/kg, or $1\times10^6$ T cells/kg body weight. In other exem- plary embodiments, a suitable dosage range of modified cells for use in a method of the present disclosure includes, without limitation, from about $1\times10^5$ cells/kg to about $1\times10^6$ cells/kg, from about $1\times10^6$ cells/kg to about $1\times10^7$ cells/kg, from about $1\times10^7$ cells/kg about $1\times10^8$ cells/kg, from about $1\times10^8$ cells/kg about $1\times10^9$ cells/kg, from about $1\times10^9$ cells/kg about $1\times10^{10}$ cells/kg, from about $1\times10^{10}$ cells/kg about $1\times10^{11}$ cells/kg. In an exemplary embodiment, a suitable dosage for use in a method of the present disclosure is about $1\times10^8$ cells/kg. In an exemplary embodiment, a suitable dosage for use in a method of the present disclosure is about $1\times10^7$ cells/kg. In other embodiments, a suitable dosage is from about $1\times10^7$ total cells to about $5\times10^7$ total cells. In some embodiments, a suitable dosage is from about $1\times10^8$ total cells to about $5\times10^8$ total cells. In some embodi- ments, a suitable dosage is from about $1.4\times10^7$ total cells to about $1.1\times10^9$ total cells. In an exemplary embodiment, a suitable dosage for use in a method of the present disclosure is about $7\times10^9$ total cells.

In some embodiments, the cells are administered at or within a certain range of error of between at or about $10^4$ and at or about $10^9$ $CD4^+$ and/or $CD8^+$ cells/kilograms (kg) body weight, such as between $10^5$ and $10^6$ $CD4^+$ and/or $CD8^+$ cells/kg body weight, for example, at or about $1\times10^5$ $CD4^+$ and/or CD8 cells/kg, $1.5\times10^5$ $CD4^+$ and/or $CD8^+$ cells/kg, $2\times10^5$ $CD4^+$ and/or $CD8^+$ cells/kg, or $1\times10^6$ CD4~ and/or $CD8^+$ cells/kg body weight. In some embodiments, the cells are administered at or within a certain range of error of, greater than, and/or at least about $1\times10^6$, about $2.5\times10^6$, about $7.5\times10^6$, or about $9\times10^6$ $CD4^+$ cells, and/or at least about $1\times10^6$, about $2.5\times10^6$, about $5\times10^6$, about $7.5\times10^6$, or about $9\times10^6$ CD8+ cells, and/or at least about $1\times10^6$, about $2.5\times10^6$, about $5\times10^6$, about $7.5\times10^6$, or about $9\times10^6$ T cells. In some embodiments, the cells are administered at or within a certain range of error of between about $10^8$ and $10^{12}$ or between about $10^{10}$ and $10^{11}$ T cells, between about $10^8$ and $10^{12}$ or between about $10^{10}$ and $10^{11}$ $CD4^+$ cells, and/or between about $10^8$ and $10^{12}$ or between about $10^{10}$ and $10^{11}$ $CD8^+$ cells.

In some embodiments, the cells are administered at or within a tolerated range of a desired output ratio of multiple cell populations or sub-types, such as CD4+ and CD8+ cells or sub-types. In some aspects, the desired ratio can be a specific ratio or can be a range of ratios, for example, in some embodiments, the desired ratio (e.g., ratio of $CD4^+$ to CD8$^+$ cells) is between at or about 5:1 and at or about 5:1 (or greater than about 1:5 and less than about 5:1), or between at or about 1:3 and at or about 3:1 (or greater than about 1:3 and less than about 3:1), such as between at or about 2:1 and at or about 1:5 (or greater than about 1:5 and less than about 2:1, such as at or about 5:1, 4.5:1, 4:1, 3.5:1, 3:1, 2.5:1, 2:1, 1.9:1, 1.8:1, 1.7:1, 1.6:1, 1.5:1, 1.4:1, 1.3:1, 1.2:1, 1.1:1, 1:1, 1:1.1, 1:1.2, 1:1.3, 1:1.4, 1:1.5, 1:1.6, 1:1.7, 1:1.8, 1:1.9:1:2, 1:2.5, 1:3, 1:3.5, 1:4, 1:4.5, or 1:5. In some aspects, the tolerated difference is within about 1%, about 2%, about 3%, about 4% about 5%, about 10%, about 15%, about 20%, about 25%, about 30%, about 35%, about 40%, about 45%, about 50% of the desired ratio, including any value in between these ranges.

In some embodiments, a dose of modified cells is administered to a subject in need thereof, in a single dose or multiple doses. In some embodiments, a dose of modified cells is administered in multiple doses, e.g., once a week or every 7 days, once every 2 weeks or every 14 days, once every 3 weeks or every 21 days, once every 4 weeks or every 28 days. In an exemplary embodiment, a single dose of modified cells is administered to a subject in need thereof. In an exemplary embodiment, a single dose of modified cells is administered to a subject in need thereof by rapid intravenous infusion.

For the prevention or treatment of disease, the appropriate dosage may depend on the type of disease to be treated, the type of cells or recombinant receptors, the severity and course of the disease, whether the cells are administered for preventive or therapeutic purposes, previous therapy, the subject's clinical history and response to the cells, and the discretion of the attending physician. The compositions and cells are in some embodiments suitably administered to the subject at one time or over a series of treatments.

In some embodiments, the cells are administered as part of a combination treatment, such as simultaneously with or sequentially with, in any order, another therapeutic intervention, such as an antibody or engineered cell or receptor or agent, such as a cytotoxic or therapeutic agent. The cells in some embodiments are co-administered with one or more additional therapeutic agents or in connection with another therapeutic intervention, either simultaneously or sequentially in any order. In some contexts, the cells are co-administered with another therapy sufficiently close in time such that the cell populations enhance the effect of one or more additional therapeutic agents, or vice versa. In some embodiments, the cells are administered prior to the one or more additional therapeutic agents. In some embodiments, the cells are administered after the one or more additional therapeutic agents. In some embodiments, the one or more additional agents include a cytokine, such as IL-2, for example, to enhance persistence. In some embodiments, the methods comprise administration of a chemotherapeutic agent.

In certain embodiments, the modified cells of the invention (e.g., a modified cell comprising a CAR) may be administered to a subject in combination with an immune checkpoint antibody (e.g., an anti-PD1, anti-CTLA-4, or anti-PDL1 antibody). For example, the modified cell may be administered in combination with an antibody or antibody fragment targeting, for example, PD-1 (programmed death 1 protein). Examples of anti-PD-1 antibodies include, but are not limited to, pembrolizumab (KEYTRUDA®, formerly lambrolizumab, also known as MK-3475), and nivolumab (BMS-936558, MDX-1106, ONO-4538, OPDIVA®) or an antigen-binding fragment thereof. In certain embodiments, the modified cell may be administered in combination with an anti-PD-L1 antibody or antigen-binding fragment thereof. Examples of anti-PD-L1 antibodies include, but are not limited to, BMS-936559, MPDL3280A (TECEN-TRIQ®, Atezolizumab), and MEDI4736 (Durvalumab, Imfinzi). In certain embodiments, the modified cell may be administered in combination with an anti-CTLA-4 antibody or antigen-binding fragment thereof. An example of an anti-CTLA-4 antibody includes, but is not limited to, Ipili-mumab (trade name Yervoy). Other types of immune checkpoint modulators may also be used including, but not limited to, small molecules, siRNA, miRNA, and CRISPR systems. Immune checkpoint modulators may be administered before, after, or concurrently with the modified cell comprising the CAR. In certain embodiments, combination treatment comprising an immune checkpoint modulator may increase the therapeutic efficacy of a therapy comprising a modified cell of the present invention.

Following administration of the cells, the biological activity of the engineered cell populations in some embodiments is measured, e.g., by any of a number of known methods. Parameters to assess include specific binding of an engineered or natural T cell or other immune cell to antigen, in vivo, e.g., by imaging, or ex vivo, e.g., by ELISA or flow cytometry. In certain embodiments, the ability of the engineered cells to destroy target cells can be measured using any suitable method known in the art, such as cytotoxicity assays described in, for example, Kochenderfer et al., J. Immunotherapy, 32(7): 689-702 (2009), and Herman et al. J. Immunological Methods, 285(1): 25-40 (2004). In certain embodiments, the biological activity of the cells is measured by assaying expression and/or secretion of one or more cytokines, such as CD 107a, IFNγ, IL-2, and TNF. In some aspects the biological activity is measured by assessing clinical outcome, such as reduction in tumor burden or load.

In certain embodiments, the subject is provided a secondary treatment. Secondary treatments include but are not limited to chemotherapy, radiation, surgery, and medications.

In some embodiments, the subject can be administered a conditioning therapy prior to CAR T cell therapy. In some embodiments, the conditioning therapy comprises administering an effective amount of cyclophosphamide to the subject. In some embodiments, the conditioning therapy comprises administering an effective amount of fludarabine to the subject. In preferred embodiments, the conditioning therapy comprises administering an effective amount of a combination of cyclophosphamide and fludarabine to the subject. Administration of a conditioning therapy prior to CAR T cell therapy may increase the efficacy of the CAR T cell therapy. Methods of conditioning patients for T cell therapy are described in U.S. Pat. No. 9,855,298, which is incorporated herein by reference in its entirety.

In some embodiments, a specific dosage regimen of the present disclosure includes a lymphodepletion step prior to the administration of the modified T cells. In an exemplary embodiment, the lymphodepletion step includes administration of cyclophosphamide and/or fludarabine.

In some embodiments, the lymphodepletion step includes administration of cyclophosphamide at a dose of between about 200 mg/m$^2$/day and about 2000 mg/m$^2$/day (e.g., 200 mg/m$^2$/day, 300 mg/m$^2$/day, or 500 mg/m$^2$/day). In an exemplary embodiment, the dose of cyclophosphamide is about 300 mg/m$^2$/day. In some embodiments, the lymphodepletion step includes administration of fludarabine at a dose of between about 20 mg/m$^2$/day and about 900 mg/m$^2$/day (e.g., 20 mg/m$^2$/day, 25 mg/m$^2$/day, 30 mg/m$^2$/day, or 60 mg/m²/day). In an exemplary embodiment, the dose of fludarabine is about 30 mg/m²/day.

In some embodiment, the lymphodepletion step includes administration of cyclophosphamide at a dose of between about 200 mg/m²/day and about 2000 mg/m²/day (e.g., 200 mg/m²/day, 300 mg/m²/day, or 500 mg/m²/day), and fludarabine at a dose of between about 20 mg/m²/day and about 900 mg/m²/day (e.g., 20 mg/m²/day, 25 mg/m²/day, 30 mg/m²/day, or 60 mg/m²/day). In an exemplary embodiment, the lymphodepletion step includes administration of cyclophosphamide at a dose of about 300 mg/m²/day, and fludarabine at a dose of about 30 mg/m²/day.

In an exemplary embodiment, the dosing of cyclophosphamide is 300 mg/m²/day over three days, and the dosing of fludarabine is 30 mg/m²/day over three days.

Dosing of lymphodepletion chemotherapy may be scheduled on Days −6 to −4 (with a −1 day window, i.e., dosing on Days −7 to −5) relative to T cell (e.g., CAR-T, TCR-T, a modified T cell, etc.) infusion on Day 0.

In an exemplary embodiment, for a subject having cancer, the subject receives lymphodepleting chemotherapy including 300 mg/m² of cyclophosphamide by intravenous infusion 3 days prior to administration of the modified T cells. In an exemplary embodiment, for a subject having cancer, the subject receives lymphodepleting chemotherapy including 300 mg/m² of cyclophosphamide by intravenous infusion for 3 days prior to administration of the modified T cells.

In an exemplary embodiment, for a subject having cancer, the subject receives lymphodepleting chemotherapy including fludarabine at a dose of between about 20 mg/m²/day and about 900 mg/m²/day (e.g., 20 mg/m²/day, 25 mg/m²/day, 30 mg/m²/day, or 60 mg/m²/day). In an exemplary embodiment, for a subject having cancer, the subject receives lymphodepleting chemotherapy including fludarabine at a dose of 30 mg/m² for 3 days.

In an exemplary embodiment, for a subject having cancer, the subject receives lymphodepleting chemotherapy including cyclophosphamide at a dose of between about 200 mg/m²/day and about 2000 mg/m²/day (e.g., 200 mg/m²/day, 300 mg/m²/day, or 500 mg/m²/day), and fludarabine at a dose of between about 20 mg/m²/day and about 900 mg/m²/day (e.g., 20 mg/m²/day, 25 mg/m²/day, 30 mg/m²/day, or 60 mg/m²/day). In an exemplary embodiment, for a subject having cancer, the subject receives lymphodepleting chemotherapy including cyclophosphamide at a dose of about 300 mg/m²/day, and fludarabine at a dose of 30 mg/m² for 3 days.

Cells of the invention can be administered in dosages and routes and at times to be determined in appropriate preclinical and clinical experimentation and trials. Cell compositions may be administered multiple times at dosages within these ranges. Administration of the cells of the invention may be combined with other methods useful to treat the desired disease or condition as determined by those of skill in the art.

It is known in the art that one of the adverse effects following infusion of CAR T cells is the onset of immune activation, known as cytokine release syndrome (CRS). CRS is immune activation resulting in elevated inflammatory cytokines. CRS is a known on-target toxicity, development of which likely correlates with efficacy. Clinical and laboratory measures range from mild CRS (constitutional symptoms and/or grade-2 organ toxicity) to severe CRS (sCRS; grade≥3 organ toxicity, aggressive clinical intervention, and/or potentially life threatening). Clinical features include: high fever, malaise, fatigue, myalgia, nausea, anorexia, tachycardia/hypotension, capillary leak, cardiac dysfunction, renal impairment, hepatic failure, and disseminated intravascular coagulation. Dramatic elevations of cytokines including interferon-gamma, granulocyte macrophage colony-stimulating factor, IL-10, and IL-6 have been shown following CAR T-cell infusion. One CRS signature is elevation of cytokines including IL-6 (severe elevation), IFN-gamma, TNF-alpha (moderate), and IL-2 (mild). Elevations in clinically available markers of inflammation including ferritin and C-reactive protein (CRP) have also been observed to correlate with the CRS syndrome. The presence of CRS generally correlates with expansion and progressive immune activation of adoptively transferred cells. It has been demonstrated that the degree of CRS severity is dictated by disease burden at the time of infusion as patients with high tumor burden experience a more sCRS.

Accordingly, the invention provides for, following the diagnosis of CRS, appropriate CRS management strategies to mitigate the physiological symptoms of uncontrolled inflammation without dampening the antitumor efficacy of the engineered cells (e.g., CAR T cells). CRS management strategies are known in the art. For example, systemic corticosteroids may be administered to rapidly reverse symptoms of sCRS (e.g., grade 3 CRS) without compromising initial antitumor response.

In some embodiments, an anti-IL-6R antibody may be administered. An example of an anti-IL-6R antibody is the Food and Drug Administration-approved monoclonal antibody tocilizumab, also known as atlizumab (marketed as Actemra, or RoActemra). Tocilizumab is a humanized monoclonal antibody against the interleukin-6 receptor (IL-6R). Administration of tocilizumab has demonstrated near-immediate reversal of CRS.

CRS is generally managed based on the severity of the observed syndrome and interventions are tailored as such. CRS management decisions may be based upon clinical signs and symptoms and response to interventions, not solely on laboratory values alone.

Mild to moderate cases generally are treated with symptom management with fluid therapy, non-steroidal anti-inflammatory drug (NSAID) and antihistamines as needed for adequate symptom relief. More severe cases include patients with any degree of hemodynamic instability; with any hemodynamic instability, the administration of tocilizumab is recommended. The first-line management of CRS may be tocilizumab, in some embodiments, at the labeled dose of 8 mg/kg IV over 60 minutes (not to exceed 800 mg/dose); tocilizumab can be repeated Q8 hours. If suboptimal response to the first dose of tocilizumab, additional doses of tocilizumab may be considered. Tocilizumab can be administered alone or in combination with corticosteroid therapy. Patients with continued or progressive CRS symptoms, inadequate clinical improvement in 12-18 hours or poor response to tocilizumab, may be treated with high-dose corticosteroid therapy, generally hydrocortisone 100 mg IV or methylprednisolone 1-2 mg/kg. In patients with more severe hemodynamic instability or more severe respiratory symptoms, patients may be administered high-dose corticosteroid therapy early in the course of the CRS. CRS management guidance may be based on published standards (Lee et al. (2019) *Biol Blood Marrow Transplant*, doi.org/10.1016/j.bbmt.2018.12.758; Neelapu et al. (2018) *Nat Rev Clin Oncology*, 15:47; Teachey et al. (2016) *Cancer Discov*, 6(6):664-679).

Features consistent with Macrophage Activation Syndrome (MAS) or Hemophagocytic lymphohistiocytosis (HLH) have been observed in patients treated with CAR-T therapy (Henter, 2007), coincident with clinical manifestations of the CRS. MAS appears to be a reaction to immune activation that occurs from the CRS, and should therefore be considered a manifestation of CRS. MAS is similar to HLH (also a reaction to immune stimulation). The clinical syndrome of MAS is characterized by high grade non-remitting fever, cytopenias affecting at least two of three lineages, and hepatosplenomegaly. It is associated with high serum ferritin, soluble interleukin-2 receptor, and triglycerides, and a decrease of circulating natural killer (NK) activity.

In one aspect, the invention includes a method of treating cancer in a subject in need thereof, comprising administering to the subject any one of the modified immune or precursor cells disclosed herein. Yet another aspect of the invention includes a method of treating cancer in a subject in need thereof, comprising administering to the subject a modified immune or precursor cell generated by any one of the methods disclosed herein.

Still another aspect of the invention includes a method of treating a disease or disorder in a subject in need thereof, comprising administering to the subject a modified T cell comprising a chimeric antigen receptor (CAR) comprising affinity for Müllerian inhibiting substance type 2 receptor (MISIIR).

In certain embodiments, the subject is administered a CAR comprising an antigen binding domain having affinity for MISIIR, a CD8α hinge domain, a CD8α transmembrane domain, a CD27 intracellular domain, and a CD3 zeta intracellular domain.

In certain embodiments, the T cell is a human cell. In certain embodiments, the T cell is autologous.

E. Methods of Producing Modified Immune Cells

In some embodiments, the CAR is introduced into a cell by an expression vector. Expression vectors comprising a nucleic acid sequence encoding a CAR of the present invention are provided herein. Suitable expression vectors include lentivirus vectors, gamma retrovirus vectors, foamy virus vectors, adeno associated virus (AAV) vectors, adenovirus vectors, engineered hybrid viruses, naked DNA, including but not limited to transposon mediated vectors, such as Sleeping Beauty, Piggybak, and Integrases such as Phi31. Some other suitable expression vectors include Herpes simplex virus (HSV) and retrovirus expression vectors.

In certain embodiments, the nucleic acid encoding a CAR is introduced into the cell via viral transduction. In certain embodiments, the viral transduction comprises contacting the immune or precursor cell with a viral vector comprising the nucleic acid encoding a CAR. In certain embodiments, the viral vector is an adeno-associated viral (AAV) vector.

Adenovirus expression vectors are based on adenoviruses, which have a low capacity for integration into genomic DNA but a high efficiency for transfecting host cells. Adenovirus expression vectors contain adenovirus sequences sufficient to: (a) support packaging of the expression vector and (b) to ultimately express the CAR in the host cell. In some embodiments, the adenovirus genome is a 36 kb, linear, double stranded DNA, where a foreign DNA sequence (e.g., a nucleic acid encoding a CAR) may be inserted to substitute large pieces of adenoviral DNA in order to make the expression vector of the present invention (see, e.g., Danthinne and Imperiale, Gene Therapy (2000) 7(20): 1707-1714).

Another expression vector is based on an adeno associated virus (AAV), which takes advantage of the adenovirus coupled systems. This AAV expression vector has a high frequency of integration into the host genome. It can infect nondividing cells, thus making it useful for delivery of genes into mammalian cells, for example, in tissue cultures or in vivo. The AAV vector has a broad host range for infectivity. Details concerning the generation and use of AAV vectors are described in U.S. Pat. Nos. 5,139,941 and 4,797,368.

Retrovirus expression vectors are capable of integrating into the host genome, delivering a large amount of foreign genetic material, infecting a broad spectrum of species and cell types and being packaged in special cell lines. The retroviral vector is constructed by inserting a nucleic acid (e.g., a nucleic acid encoding a CAR) into the viral genome at certain locations to produce a virus that is replication defective. Though the retroviral vectors are able to infect a broad variety of cell types, integration and stable expression of the CAR requires the division of host cells.

Lentiviral vectors are derived from lentiviruses, which are complex retroviruses that, in addition to the common retroviral genes gag, pol, and env, contain other genes with regulatory or structural function (see, e.g., U.S. Pat. Nos. 6,013,516 and 5,994,136). Some examples of lentiviruses include the Human Immunodeficiency Viruses (HIV-1, HIV-2) and the Simian Immunodeficiency Virus (SIV). Lentiviral vectors have been generated by multiply attenuating the HIV virulence genes, for example, the genes env, vif, vpr, vpu and nef are deleted making the vector biologically safe. Lentiviral vectors are capable of infecting non-dividing cells and can be used for both in vivo and ex vivo gene transfer and expression, e.g., of a nucleic acid encoding a CAR (see, e.g., U.S. Pat. No. 5,994,136).

Expression vectors including a nucleic acid of the present disclosure can be introduced into a host cell by any means known to persons skilled in the art. The expression vectors may include viral sequences for transfection, if desired. Alternatively, the expression vectors may be introduced by fusion, electroporation, biolistics, transfection, lipofection, or the like. The host cell may be grown and expanded in culture before introduction of the expression vectors, followed by the appropriate treatment for introduction and integration of the vectors. The host cells are then expanded and may be screened by virtue of a marker present in the vectors. Various markers that may be used are known in the art, and may include hprt, neomycin resistance, thymidine kinase, hygromycin resistance, etc. As used herein, the terms "cell," "cell line," and "cell culture" may be used interchangeably. In some embodiments, the host cell an immune cell or precursor thereof, e.g., a T cell, an NK cell, or an NKT cell.

The present invention also provides genetically engineered cells which include and stably express a CAR of the present disclosure. In some embodiments, the genetically engineered cells are genetically engineered T-lymphocytes (T cells), naive T cells (TN), memory T cells (for example, central memory T cells (TCM), effector memory cells (TEM)), natural killer cells (NK cells), and macrophages capable of giving rise to therapeutically relevant progeny. In certain embodiments, the genetically engineered cells are autologous cells.

Modified cells (e.g., comprising a CAR) may be produced by stably transfecting host cells with an expression vector including a nucleic acid of the present disclosure. Additional methods for generating a modified cell of the present disclosure include, without limitation, chemical transformation methods (e.g., using calcium phosphate, dendrimers, liposomes and/or cationic polymers), non-chemical transformation methods (e.g., electroporation, optical transformation, gene electrotransfer and/or hydrodynamic delivery) and/or particle-based methods (e.g., impalefection, using a gene gun and/or magnetofection). Transfected cells expressing a CAR of the present disclosure may be expanded ex vivo.

Physical methods for introducing an expression vector into host cells include calcium phosphate precipitation, lipofection, particle bombardment, microinjection, electroporation, and the like. Methods for producing cells including vectors and/or exogenous nucleic acids are well-known in the art. See, e.g., Sambrook et al. (2001), Molecular Cloning: A Laboratory Manual, Cold Spring Harbor Laboratory, New York. Chemical methods for introducing an expression vector into a host cell include colloidal dispersion systems, such as macromolecule complexes, nanocapsules, microspheres, beads, and lipid-based systems including oil-in-water emulsions, micelles, mixed micelles, and liposomes.

Lipids suitable for use can be obtained from commercial sources. For example, dimyristyl phosphatidylcholine ("DMPC") can be obtained from Sigma, St. Louis, MO; dicetyl phosphate ("DCP") can be obtained from K & K Laboratories (Plainview, NY); cholesterol ("Choi") can be obtained from Calbiochem-Behring; dimyristyl phosphatidylglycerol ("DMPG") and other lipids may be obtained from Avanti Polar Lipids, Inc. (Birmingham, AL). Stock solutions of lipids in chloroform or chloroform/methanol can be stored at about −20° C. Chloroform may be used as the only solvent since it is more readily evaporated than methanol. "Liposome" is a generic term encompassing a variety of single and multilamellar lipid vehicles formed by the generation of enclosed lipid bilayers or aggregates. Liposomes can be characterized as having vesicular structures with a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh et al., 1991 Glycobiology 5: 505-10). Compositions that have different structures in solution than the normal vesicular structure are also encompassed. For example, the lipids may assume a micellar structure or merely exist as non-uniform aggregates of lipid molecules. Also contemplated are lipofectamine-nucleic acid complexes.

Regardless of the method used to introduce exogenous nucleic acids into a host cell or otherwise expose a cell to the inhibitor of the present invention, in order to confirm the presence of the nucleic acids in the host cell, a variety of assays may be performed. Such assays include, for example, molecular biology assays well known to those of skill in the art, such as Southern and Northern blotting, RT-PCR and PCR; biochemistry assays, such as detecting the presence or absence of a particular peptide, e.g., by immunological means (ELISAs and Western blots) or by assays described herein to identify agents falling within the scope of the invention.

In one embodiment, the nucleic acids introduced into the host cell are RNA. In another embodiment, the RNA is mRNA that comprises in vitro transcribed RNA or synthetic RNA. The RNA may be produced by in vitro transcription using a polymerase chain reaction (PCR)-generated template. DNA of interest from any source can be directly converted by PCR into a template for in vitro mRNA synthesis using appropriate primers and RNA polymerase. The source of the DNA may be, for example, genomic DNA, plasmid DNA, phage DNA, cDNA, synthetic DNA sequence or any other appropriate source of DNA.

PCR may be used to generate a template for in vitro transcription of mRNA which is then introduced into cells. Methods for performing PCR are well known in the art. Primers for use in PCR are designed to have regions that are substantially complementary to regions of the DNA to be used as a template for the PCR. "Substantially complementary," as used herein, refers to sequences of nucleotides where a majority or all of the bases in the primer sequence are complementary. Substantially complementary sequences are able to anneal or hybridize with the intended DNA target under annealing conditions used for PCR. The primers can be designed to be substantially complementary to any portion of the DNA template. For example, the primers can be designed to amplify the portion of a gene that is normally transcribed in cells (the open reading frame), including 5' and 3' UTRs. The primers may also be designed to amplify a portion of a gene that encodes a particular domain of interest. In one embodiment, the primers are designed to amplify the coding region of a human cDNA, including all or portions of the 5' and 3' UTRs. Primers useful for PCR are generated by synthetic methods that are well known in the art. "Forward primers" are primers that contain a region of nucleotides that are substantially complementary to nucleotides on the DNA template that are upstream of the DNA sequence that is to be amplified. "Upstream" is used herein to refer to a location 5, to the DNA sequence to be amplified relative to the coding strand. "Reverse primers" are primers that contain a region of nucleotides that are substantially complementary to a double-stranded DNA template that are downstream of the DNA sequence that is to be amplified. "Downstream" is used herein to refer to a location 3' to the DNA sequence to be amplified relative to the coding strand.

Chemical structures that have the ability to promote stability and/or translation efficiency of the RNA may also be used. The RNA preferably has 5' and 3' UTRs. In one embodiment, the 5' UTR is between zero and 3000 nucleotides in length. The length of 5' and 3' UTR sequences to be added to the coding region can be altered by different methods, including, but not limited to, designing primers for PCR that anneal to different regions of the UTRs. Using this approach, one of ordinary skill in the art can modify the 5' and 3' UTR lengths required to achieve optimal translation efficiency following transfection of the transcribed RNA.

The 5' and 3' UTRs can be the naturally occurring, endogenous 5' and 3' UTRs for the gene of interest. Alternatively, UTR sequences that are not endogenous to the gene of interest can be added by incorporating the UTR sequences into the forward and reverse primers or by any other modifications of the template. The use of UTR sequences that are not endogenous to the gene of interest can be useful for modifying the stability and/or translation efficiency of the RNA. For example, it is known that AU-rich elements in 3' UTR sequences can decrease the stability of mRNA. Therefore, 3' UTRs can be selected or designed to increase the stability of the transcribed RNA based on properties of UTRs that are well known in the art.

In one embodiment, the 5' UTR can contain the Kozak sequence of the endogenous gene. Alternatively, when a 5' UTR that is not endogenous to the gene of interest is being added by PCR as described above, a consensus Kozak sequence can be redesigned by adding the 5' UTR sequence. Kozak sequences can increase the efficiency of translation of some RNA transcripts, but does not appear to be required for all RNAs to enable efficient translation. The requirement for Kozak sequences for many mRNAs is known in the art. In other embodiments the 5' UTR can be derived from an RNA virus whose RNA genome is stable in cells. In other embodiments various nucleotide analogues can be used in the 3' or 5' UTR to impede exonuclease degradation of the mRNA.

To enable synthesis of RNA from a DNA template without the need for gene cloning, a promoter of transcription should be attached to the DNA template upstream of the sequence to be transcribed. When a sequence that functions as a promoter for an RNA polymerase is added to the 5' end of the forward primer, the RNA polymerase promoter becomes incorporated into the PCR product upstream of the open reading frame that is to be transcribed. In one embodiment, the promoter is a T7 polymerase promoter, as described elsewhere herein. Other useful promoters include, but are not limited to, T3 and SP6 RNA polymerase promoters. Consensus nucleotide sequences for T7, T3 and SP6 promoters are known in the art.

In one embodiment, the mRNA has both a cap on the 5' end and a 3' poly(A) tail which determine ribosome binding, initiation of translation and stability mRNA in the cell. On a circular DNA template, for instance, plasmid DNA, RNA polymerase produces a long concatameric product which is not suitable for expression in eukaryotic cells. The transcription of plasmid DNA linearized at the end of the 3' UTR results in normal sized mRNA which is not effective in eukaryotic transfection even if it is polyadenylated after transcription.

On a linear DNA template, phage T7 RNA polymerase can extend the 3' end of the transcript beyond the last base of the template (Schenborn and Mierendorf, Nuc Acids Res., 13:6223-36 (1985); Nacheva and Berzal-Herranz, Eur. J. Biochem., 270:1485-65 (2003).

The polyA/T segment of the transcriptional DNA template can be produced during PCR by using a reverse primer containing a polyT tail, such as 100T tail (size can be 50-5000 T), or after PCR by any other method, including, but not limited to, DNA ligation or in vitro recombination. Poly(A) tails also provide stability to RNAs and reduce their degradation. Generally, the length of a poly(A) tail positively correlates with the stability of the transcribed RNA. In one embodiment, the poly(A) tail is between 100 and 5000 adenosines.

Poly(A) tails of RNAs can be further extended following in vitro transcription with the use of a poly(A) polymerase, such as E. coli polyA polymerase (E-PAP). In one embodiment, increasing the length of a poly(A) tail from 100 nucleotides to between 300 and 400 nucleotides results in about a two-fold increase in the translation efficiency of the RNA. Additionally, the attachment of different chemical groups to the 3' end can increase mRNA stability. Such attachment can contain modified/artificial nucleotides, aptamers and other compounds. For example, ATP analogs can be incorporated into the poly(A) tail using poly(A) polymerase. ATP analogs can further increase the stability of the RNA.

5' caps also provide stability to RNA molecules. In a preferred embodiment, RNAs produced by the methods disclosed herein include a 5' cap. The 5' cap is provided using techniques known in the art and described herein (Cougot, et al., Trends in Biochem. Sci., 29:436-444 (2001); Stepinski, et al., RNA, 7:1468-95 (2001); Elango, et al., Biochim. Biophys. Res. Commun., 330:958-966 (2005)).

In some embodiments, the RNA is electroporated into the cells, such as in vitro transcribed RNA. Any solutes suitable for cell electroporation, which can contain factors facilitating cellular permeability and viability such as sugars, peptides, lipids, proteins, antioxidants, and surfactants can be included.

In some embodiments, a nucleic acid encoding a CAR of the present disclosure will be RNA, e.g., in vitro synthesized RNA. Methods for in vitro synthesis of RNA are known in the art; any known method can be used to synthesize RNA comprising a sequence encoding a CAR. Methods for introducing RNA into a host cell are known in the art. See, e.g., Zhao et al. Cancer Res. (2010) 15: 9053. Introducing RNA comprising a nucleotide sequence encoding a CAR into a host cell can be carried out in vitro, ex vivo or in vivo. For example, a host cell (e.g., an NK cell, a cytotoxic T lymphocyte, etc.) can be electroporated in vitro or ex vivo with RNA comprising a nucleotide sequence encoding a CAR.

The disclosed methods can be applied to the modulation of T cell activity in basic research and therapy, in the fields of cancer, stem cells, acute and chronic infections, and autoimmune diseases, including the assessment of the ability of the genetically modified T cell to kill a target cancer cell.

The methods also provide the ability to control the level of expression over a wide range by changing, for example, the promoter or the amount of input RNA, making it possible to individually regulate the expression level. Furthermore, the PCR-based technique of mRNA production greatly facilitates the design of the mRNAs with different structures and combination of their domains.

One advantage of RNA transfection methods of the invention is that RNA transfection is essentially transient and a vector-free. An RNA transgene can be delivered to a lymphocyte and expressed therein following a brief in vitro cell activation, as a minimal expressing cassette without the need for any additional viral sequences. Under these conditions, integration of the transgene into the host cell genome is unlikely. Cloning of cells is not necessary because of the efficiency of transfection of the RNA and its ability to uniformly modify the entire lymphocyte population.

Genetic modification of T cells with in vitro-transcribed RNA (IVT-RNA) makes use of two different strategies both of which have been successively tested in various animal models. Cells are transfected with in vitro-transcribed RNA by means of lipofection or electroporation. It is desirable to stabilize IVT-RNA using various modifications in order to achieve prolonged expression of transferred IVT-RNA.

Some IVT vectors are known in the literature which are utilized in a standardized manner as template for in vitro transcription and which have been genetically modified in such a way that stabilized RNA transcripts are produced. Currently protocols used in the art are based on a plasmid vector with the following structure: a 5' RNA polymerase promoter enabling RNA transcription, followed by a gene of interest which is flanked either 3' and/or 5' by untranslated regions (UTR), and a 3' polyadenyl cassette containing 50-70 A nucleotides. Prior to in vitro transcription, the circular plasmid is linearized downstream of the polyadenyl cassette by type II restriction enzymes (recognition sequence corresponds to cleavage site). The polyadenyl cassette thus corresponds to the later poly(A) sequence in the transcript. As a result of this procedure, some nucleotides remain as part of the enzyme cleavage site after linearization and extend or mask the poly(A) sequence at the 3' end. It is not clear, whether this nonphysiological overhang affects the amount of protein produced intracellularly from such a construct.

In another aspect, the RNA construct is delivered into the cells by electroporation. See, e.g., the formulations and methodology of electroporation of nucleic acid constructs into mammalian cells as taught in US 2004/0014645, US 2005/0052630A1, US 2005/0070841A1, US 2004/

0059285A1, US 2004/0092907A1. The various parameters including electric field strength required for electroporation of any known cell type are generally known in the relevant research literature as well as numerous patents and applications in the field. See e.g., U.S. Pat. Nos. 6,678,556, 7,171, 264, and 7,173,116. Apparatus for therapeutic application of electroporation are available commercially, e.g., the MedPulser™ DNA Electroporation Therapy System (Inovio/Genetronics, San Diego, Calif.), and are described in patents such as U.S. Pat. Nos. 6,567,694; 6,516,223, 5,993, 434, 6,181,964, 6,241,701, and 6,233,482: electroporation may also be used for transfection of cells in vitro as described e.g. in US20070128708A1. Electroporation may also be utilized to deliver nucleic acids into cells in vitro. Accordingly, electroporation-mediated administration into cells of nucleic acids including expression constructs utilizing any of the many available devices and electroporation systems known to those of skill in the art presents an exciting new means for delivering an RNA of interest to a target cell.

In some embodiments, the immune cells (e.g. T cells) can be incubated or cultivated prior to, during and/or subsequent to introducing the nucleic acid molecule encoding the CAR. In some embodiments, the cells (e.g. T cells) can be incubated or cultivated prior to, during or subsequent to the introduction of the nucleic acid molecule encoding the CAR, such as prior to, during or subsequent to the transduction of the cells with a viral vector (e.g. lentiviral vector) encoding the CAR. In some embodiments, the cells (e.g. T cells) can be incubated or cultivated prior to, during or subsequent to the introduction of the CAR, such as prior to, during or subsequent to contacting the cells with the agent or prior to, during or subsequent to delivering the agent into the cells, e.g. via electroporation. In some embodiments, the method includes activating or stimulating cells with a stimulating or activating agent (e.g. anti-CD3/anti-CD28 antibodies) prior to introducing the nucleic acid molecule encoding the CAR.

In some embodiments, prior to the introducing of the agent, the cells are allowed to rest, e.g. by removal of any stimulating or activating agent. In some embodiments, prior to introducing the agent, the stimulating or activating agent and/or cytokines are not removed. Those of skill in the art will be able to determine the order in which each of the one or more nucleic acid sequences are introduced into the host cell.

F. Nucleic Acids and Expression Vectors

The present disclosure provides a nucleic acid encoding a CAR. In some embodiments, a nucleic acid of the present disclosure is provided for the production of a CAR as described herein, e.g., in a mammalian cell. In some embodiments, a nucleic acid of the present disclosure provides for amplification of the CAR-encoding nucleic acid.

In some embodiments, a nucleic acid of the present disclosure may be operably linked to a transcriptional control element, e.g., a promoter, and enhancer, etc. Suitable promoter and enhancer elements are known to those of skill in the art.

In certain embodiments, the nucleic acid encoding a CAR is in operable linkage with a promoter. In certain embodiments, the promoter is a phosphoglycerate kinase-1 (PGK) promoter. In certain embodiments, the promoter is an EF-1α promoter.

For expression in a bacterial cell, suitable promoters include, but are not limited to, lacI, lacZ, T3, T7, gpt, lambda P and trc. For expression in a eukaryotic cell, suitable promoters include, but are not limited to, light and/or heavy chain immunoglobulin gene promoter and enhancer elements; cytomegalovirus immediate early promoter; herpes simplex virus thymidine kinase promoter; early and late SV40 promoters; promoter present in long terminal repeats from a retrovirus; mouse metallothionein-I promoter; and various art-known tissue specific promoters. Suitable reversible promoters, including reversible inducible promoters are known in the art. Such reversible promoters may be isolated and derived from many organisms, e.g., eukaryotes and prokaryotes. Modification of reversible promoters derived from a first organism for use in a second organism, e.g., a first prokaryote and a second a eukaryote, a first eukaryote and a second a prokaryote, etc., is well known in the art. Such reversible promoters, and systems based on such reversible promoters but also comprising additional control proteins, include, but are not limited to, alcohol regulated promoters (e.g., alcohol dehydrogenase I (alcA) gene promoter, promoters responsive to alcohol transactivator proteins (AlcR), etc.), tetracycline regulated promoters, (e.g., promoter systems including TetActivators, TetON, TetOFF, etc.), steroid regulated promoters (e.g., rat glucocorticoid receptor promoter systems, human estrogen receptor promoter systems, retinoid promoter systems, thyroid promoter systems, ecdysone promoter systems, mifepristone promoter systems, etc.), metal regulated promoters (e.g., metallothionein promoter systems, etc.), pathogenesis-related regulated promoters (e.g., salicylic acid regulated promoters, ethylene regulated promoters, benzothiadiazole regulated promoters, etc.), temperature regulated promoters (e.g., heat shock inducible promoters (e.g., HSP-70, HSP-90, soybean heat shock promoter, etc.), light regulated promoters, synthetic inducible promoters, and the like.

In some embodiments, the promoter is a CD8 cell-specific promoter, a CD4 cell-specific promoter, a neutrophil-specific promoter, or an NK-specific promoter. For example, a CD4 gene promoter can be used; see, e.g., Salmon et al. Proc. Natl. Acad. Sci. USA (1993) 90:7739; and Marodon et al. (2003) Blood 101:3416. As another example, a CD8 gene promoter can be used. NK cell-specific expression can be achieved by use of an NcrI (p46) promoter; see, e.g., Eckelhart et al. Blood (2011) 117:1565.

For expression in a yeast cell, a suitable promoter is a constitutive promoter such as an ADH1 promoter, a PGK1 promoter, an ENO promoter, a PYK1 promoter and the like; or a regulatable promoter such as a GAL1 promoter, a GAL10 promoter, an ADH2 promoter, a PHO5 promoter, a CUP1 promoter, a GALT promoter, a MET25 promoter, a MET3 promoter, a CYC1 promoter, a HIS3 promoter, an ADH1 promoter, a PGK promoter, a GAPDH promoter, an ADC1 promoter, a TRP1 promoter, a URA3 promoter, a LEU2 promoter, an ENO promoter, a TP1 promoter, and AOX1 (e.g., for use in Pichia). Selection of the appropriate vector and promoter is well within the level of ordinary skill in the art. Suitable promoters for use in prokaryotic host cells include, but are not limited to, a bacteriophage T7 RNA polymerase promoter; a trp promoter; a lac operon promoter; a hybrid promoter, e.g., a lac/tac hybrid promoter, a tac/trc hybrid promoter, a trp/lac promoter, a T7/lac promoter; a trc promoter; a tac promoter, and the like; an araBAD promoter; in vivo regulated promoters, such as an ssaG promoter or a related promoter (see, e.g., U.S. Patent Publication No. 20040131637), a pagC promoter (Pulkkinen and Miller, J. Bacteriol. (1991) 173(1): 86-93; Alpuche-Aranda et al., Proc. Natl. Acad. Sci. USA (1992) 89(21): 10079-83), a nirB promoter (Harborne et al. Mol. Micro. (1992) 6:2805-2813), and the like (see, e.g., Dunstan et al., Infect. Immun. (1999)

67:5133-5141; McKelvie et al., Vaccine (2004) 22:3243-3255; and Chatfield et al., Biotechnol. (1992) 10:888-892); a sigma70 promoter, e.g., a consensus sigma70 promoter (see, e.g., GenBank Accession Nos. AX798980, AX798961, and AX798183); a stationary phase promoter, e.g., a dps promoter, an spv promoter, and the like; a promoter derived from the pathogenicity island SPI-2 (see, e.g., WO96/17951); an actA promoter (see, e.g., Shetron-Rama et al., Infect. Immun. (2002) 70:1087-1096); an rpsM promoter (see, e.g., Valdivia and Falkow Mol. Microbiol. (1996). 22:367); a tet promoter (see, e.g., Hillen, W. and Wissmann, A. (1989) In Saenger, W. and Heinemann, U. (eds), Topics in Molecular and Structural Biology, Protein—Nucleic Acid Interaction. Macmillan, London, UK, Vol. 10, pp. 143-162); an SP6 promoter (see, e.g., Melton et al., Nucl. Acids Res. (1984) 12:7035); and the like. Suitable strong promoters for use in prokaryotes such as *Escherichia coli* include, but are not limited to Trc, Tac, T5, T7, and PLambda. Non-limiting examples of operators for use in bacterial host cells include a lactose promoter operator (LacI repressor protein changes conformation when contacted with lactose, thereby preventing the Lad repressor protein from binding to the operator), a tryptophan promoter operator (when complexed with tryptophan, TrpR repressor protein has a conformation that binds the operator; in the absence of tryptophan, the TrpR repressor protein has a conformation that does not bind to the operator), and a tac promoter operator (see, e.g., deBoer et al., Proc. Natl. Acad. Sci. U.S.A. (1983) 80:21-25).

Other examples of suitable promoters include the immediate early cytomegalovirus (CMV) promoter sequence. This promoter sequence is a strong constitutive promoter sequence capable of driving high levels of expression of any polynucleotide sequence operatively linked thereto. Other constitutive promoter sequences may also be used, including, but not limited to a simian virus 40 (SV40) early promoter, a mouse mammary tumor virus (MMTV) or human immunodeficiency virus (HIV) long terminal repeat (LTR) promoter, a MoMuLV promoter, an avian leukemia virus promoter, an Epstein-Barr virus immediate early promoter, a Rous sarcoma virus promoter, the EF-1 alpha promoter, as well as human gene promoters such as, but not limited to, an actin promoter, a myosin promoter, a hemoglobin promoter, and a creatine kinase promoter. Further, the invention should not be limited to the use of constitutive promoters. Inducible promoters are also contemplated as part of the invention. The use of an inducible promoter provides a molecular switch capable of turning on expression of the polynucleotide sequence which it is operatively linked when such expression is desired, or turning off the expression when expression is not desired. Examples of inducible promoters include, but are not limited to a metallothionine promoter, a glucocorticoid promoter, a progesterone promoter, and a tetracycline promoter.

In some embodiments, the locus or construct or transgene containing the suitable promoter is irreversibly switched through the induction of an inducible system. Suitable systems for induction of an irreversible switch are well known in the art, e.g., induction of an irreversible switch may make use of a Cre-lox-mediated recombination (see, e.g., Fuhrmann-Benzakein, et al., Proc. Natl. Acad. Sci. USA (2000) 28:e99, the disclosure of which is incorporated herein by reference). Any suitable combination of recombinase, endonuclease, ligase, recombination sites, etc. known to the art may be used in generating an irreversibly switchable promoter. Methods, mechanisms, and requirements for performing site-specific recombination, described elsewhere herein, find use in generating irreversibly switched promoters and are well known in the art, see, e.g., Grindley et al. Annual Review of Biochemistry (2006) 567-605; and Tropp, Molecular Biology (2012) (Jones & Bartlett Publishers, Sudbury, Mass.), the disclosures of which are incorporated herein by reference.

In some embodiments, a nucleic acid of the present disclosure further comprises a nucleic acid sequence encoding a CAR inducible expression cassette. In one embodiment, the CAR inducible expression cassette is for the production of a transgenic polypeptide product that is released during CAR signaling. See, e.g., Chmielewski and Abken, Expert Opin. Biol. Ther. (2015) 15(8): 1145-1154; and Abken, Immunotherapy (2015) 7(5): 535-544. In some embodiments, a nucleic acid of the present disclosure further comprises a nucleic acid sequence encoding a cytokine operably linked to a T-cell activation responsive promoter. In some embodiments, the cytokine operably linked to a T-cell activation responsive promoter is present on a separate nucleic acid sequence. In one embodiment, the cytokine is IL-12.

A nucleic acid of the present disclosure may be present within an expression vector and/or a cloning vector. An expression vector can include a selectable marker, an origin of replication, and other features that provide for replication and/or maintenance of the vector. Suitable expression vectors include, e.g., plasmids, viral vectors, and the like. Large numbers of suitable vectors and promoters are known to those of skill in the art; many are commercially available for generating a subject recombinant construct. The following vectors are provided by way of example, and should not be construed in anyway as limiting: Bacterial: pBs, phagescript, PsiX174, pBluescript SK, pBs KS, pNH8a, pNH16a, pNH18a, pNH46a (Stratagene, La Jolla, Calif., USA); pTrc99A, pKK223-3, pKK233-3, pDR540, and pRIT5 (Pharmacia, Uppsala, Sweden). Eukaryotic: pWLneo, pSV2cat, pOG44, PXR1, pSG (Stratagene) pSVK3, pBPV, pMSG and pSVL (Pharmacia).

Expression vectors generally have convenient restriction sites located near the promoter sequence to provide for the insertion of nucleic acid sequences encoding heterologous proteins. A selectable marker operative in the expression host may be present. Suitable expression vectors include, but are not limited to, viral vectors (e.g. viral vectors based on vaccinia virus; poliovirus; adenovirus (see, e.g., Li et al., Invest. Opthalmol. Vis. Sci. (1994) 35: 2543-2549: Borras et al., Gene Ther. (1999) 6: 515-524; Li and Davidson, Proc. Natl. Acad. Sci. USA (1995) 92: 7700-7704; Sakamoto et al., H. Gene Ther. (1999) 5: 1088-1097; WO 94/12649, WO 93/03769; WO 93/19191; WO 94/28938; WO 95/11984 and WO 95/00655); adeno-associated virus (see, e.g., Ali et al., Hum. Gene Ther. (1998) 9: 81-86, Flannery et al., Proc. Natl. Acad. Sci. USA (1997) 94: 6916-6921; Bennett et al., Invest. Opthalmol. Vis. Sci. (1997) 38: 2857-2863; Jomary et al., Gene Ther. (1997) 4:683 690, Rolling et al., Hum. Gene Ther. (1999) 10: 641-648: Ali et al., Hum. Mol. Genet. (1996) 5: 591-594; Srivastava in WO 93/09239, Samulski et al., J. Vir. (1989) 63: 3822-3828; Mendelson et al., Virol. (1988) 166: 154-165; and Flotte et al., Proc. Natl. Acad. Sci. USA (1993) 90: 10613-10617): SV40; herpes simplex virus; human immunodeficiency virus (see, e.g., Miyoshi et al., Proc. Natl. Acad. Sci. USA (1997) 94: 10319-23; Takahashi et al., J. Virol. (1999) 73: 7812-7816); a retroviral vector (e.g., Murine Leukemia Virus, spleen necrosis virus, and vectors derived from retroviruses such as Rous Sarcoma Virus, Harvey Sarcoma Virus, avian leukosis virus, human immunodeficiency virus, myeloproliferative sarcoma virus, and mammary tumor virus); and the like.

Additional expression vectors suitable for use are, e.g., without limitation, a lentivirus vector, a gamma retrovirus vector, a foamy virus vector, an adeno-associated virus vector, an adenovirus vector, a pox virus vector, a herpes virus vector, an engineered hybrid virus vector, a transposon mediated vector, and the like. Viral vector technology is well known in the art and is described, for example, in Sambrook et al., 2012, Molecular Cloning: A Laboratory Manual, volumes 1-4, Cold Spring Harbor Press, NY), and in other virology and molecular biology manuals. Viruses, which are useful as vectors include, but are not limited to, retroviruses, adenoviruses, adeno-associated viruses, herpes viruses, and lentiviruses.

In general, a suitable vector contains an origin of replication functional in at least one organism, a promoter sequence, convenient restriction endonuclease sites, and one or more selectable markers, (e.g., WO 01/96584; WO 01/29058; and U.S. Pat. No. 6,326,193).

In some embodiments, an expression vector (e.g., a lentiviral vector) may be used to introduce the CAR into an immune cell or precursor thereof (e.g., a T cell). Accordingly, an expression vector (e.g., a lentiviral vector) of the present invention may comprise a nucleic acid encoding for a CAR. In some embodiments, the expression vector (e.g., lentiviral vector) will comprise additional elements that will aid in the functional expression of the CAR encoded therein. In some embodiments, an expression vector comprising a nucleic acid encoding for a CAR further comprises a mammalian promoter. In one embodiment, the vector further comprises an elongation-factor-1-alpha promoter (EF-1α promoter). Use of an EF-1α promoter may increase the efficiency in expression of downstream transgenes (e.g., a CAR encoding nucleic acid sequence). Physiologic promoters (e.g., an EF-1α promoter) may be less likely to induce integration mediated genotoxicity, and may abrogate the ability of the retroviral vector to transform stem cells. Other physiological promoters suitable for use in a vector (e.g., lentiviral vector) are known to those of skill in the art and may be incorporated into a vector of the present invention. In some embodiments, the vector (e.g., lentiviral vector) further comprises a non-requisite cis acting sequence that may improve titers and gene expression. One non-limiting example of a non-requisite cis acting sequence is the central polypurine tract and central termination sequence (cPPT/CTS) which is important for efficient reverse transcription and nuclear import. Other non-requisite cis acting sequences are known to those of skill in the art and may be incorporated into a vector (e.g., lentiviral vector) of the present invention. In some embodiments, the vector further comprises a post-transcriptional regulatory element. Posttranscriptional regulatory elements may improve RNA translation, improve transgene expression and stabilize RNA transcripts. One example of a posttranscriptional regulatory element is the woodchuck hepatitis virus posttranscriptional regulatory element (WPRE). Accordingly, in some embodiments a vector for the present invention further comprises a WPRE sequence. Various posttranscriptional regulator elements are known to those of skill in the art and may be incorporated into a vector (e.g., lentiviral vector) of the present invention. A vector of the present invention may further comprise additional elements such as a rev response element (RRE) for RNA transport, packaging sequences, and 5' and 3' long terminal repeats (LTRs). The term "long terminal repeat" or "LTR" refers to domains of base pairs located at the ends of retroviral DNAs which comprise U3, R and U5 regions. LTRs generally provide functions required for the expression of retroviral genes (e.g., promotion, initiation and polyadenylation of gene transcripts) and to viral replication. In one embodiment, a vector (e.g., lentiviral vector) of the present invention includes a 3' U3 deleted LTR. Accordingly, a vector (e.g., lentiviral vector) of the present invention may comprise any combination of the elements described herein to enhance the efficiency of functional expression of transgenes. For example, a vector (e.g., lentiviral vector) of the present invention may comprise a WPRE sequence, cPPT sequence, RRE sequence, 5'LTR, 3' U3 deleted LTR' in addition to a nucleic acid encoding for a CAR.

Vectors of the present invention may be self-inactivating vectors. As used herein, the term "self-inactivating vector" refers to vectors in which the 3' LTR enhancer promoter region (U3 region) has been modified (e.g., by deletion or substitution). A self-inactivating vector may prevent viral transcription beyond the first round of viral replication. Consequently, a self-inactivating vector may be capable of infecting and then integrating into a host genome (e.g., a mammalian genome) only once, and cannot be passed further. Accordingly, self-inactivating vectors may greatly reduce the risk of creating a replication-competent virus.

In some embodiments, a nucleic acid of the present invention may be RNA, e.g., in vitro synthesized RNA. Methods for in vitro synthesis of RNA are known to those of skill in the art; any known method can be used to synthesize RNA comprising a sequence encoding a CAR of the present disclosure. Methods for introducing RNA into a host cell are known in the art. See, e.g., Zhao et al. Cancer Res. (2010) 15: 9053. Introducing RNA comprising a nucleotide sequence encoding a CAR of the present disclosure into a host cell can be carried out in vitro, ex vivo or in vivo. For example, a host cell (e.g., an NK cell, a cytotoxic T lymphocyte, etc.) can be electroporated in vitro or ex vivo with RNA comprising a nucleotide sequence encoding a CAR of the present disclosure.

In order to assess the expression of a polypeptide or portions thereof, the expression vector to be introduced into a cell may also contain either a selectable marker gene or a reporter gene, or both, to facilitate identification and selection of expressing cells from the population of cells sought to be transfected or infected through viral vectors. In some embodiments, the selectable marker may be carried on a separate piece of DNA and used in a co-transfection procedure. Both selectable markers and reporter genes may be flanked with appropriate regulatory sequences to enable expression in the host cells. Useful selectable markers include, without limitation, antibiotic-resistance genes.

Reporter genes are used for identifying potentially transfected cells and for evaluating the functionality of regulatory sequences. In general, a reporter gene is a gene that is not present in or expressed by the recipient organism or tissue and that encodes a polypeptide whose expression is manifested by some easily detectable property, e.g., enzymatic activity. Expression of the reporter gene is assessed at a suitable time after the DNA has been introduced into the recipient cells. Suitable reporter genes may include, without limitation, genes encoding luciferase, beta-galactosidase, chloramphenicol acetyl transferase, secreted alkaline phosphatase, or the green fluorescent protein gene (e.g., Ui-Tei et al., 2000 FEBS Letters 479: 79-82).

G. Sources of Immune Cells

In certain embodiments, a source of immune cells is obtained from a subject for ex vivo manipulation. Sources of target cells for ex vivo manipulation may also include, e.g., autologous or heterologous donor blood, cord blood, or bone marrow. For example the source of immune cells may be from the subject to be treated with the modified immune cells of the invention, e.g., the subject's blood, the subject's cord blood, or the subject's bone marrow. Non-limiting examples of subjects include humans, dogs, cats, mice, rats, and transgenic species thereof. Preferably, the subject is a human.

Immune cells can be obtained from a number of sources, including blood, peripheral blood mononuclear cells, bone marrow, lymph node tissue, spleen tissue, umbilical cord, lymph, or lymphoid organs. Immune cells are cells of the immune system, such as cells of the innate or adaptive immunity, e.g., myeloid or lymphoid cells, including lymphocytes, typically T cells and/or NK cells. Other exemplary cells include stem cells, such as multipotent and pluripotent stem cells, including induced pluripotent stem cells (iPSCs). In some aspects, the cells are human cells. With reference to the subject to be treated, the cells may be allogeneic and/or autologous. The cells typically are primary cells, such as those isolated directly from a subject and/or isolated from a subject and frozen.

In certain embodiments, the immune cell is a T cell, e.g., a CD8+ T cell (e.g., a CD8+ naive T cell, central memory T cell, or effector memory T cell), a CD4+ T cell, a natural killer T cell (NKT cells), a regulatory T cell (Treg), a stem cell memory T cell, a lymphoid progenitor cell a hematopoietic stem cell, a natural killer cell (NK cell) or a dendritic cell. In some embodiments, the cells are monocytes or granulocytes, e.g., myeloid cells, macrophages, neutrophils, dendritic cells, mast cells, eosinophils, and/or basophils. In an embodiment, the target cell is an induced pluripotent stem (iPS) cell or a cell derived from an iPS cell, e.g., an iPS cell generated from a subject, manipulated to alter (e.g., induce a mutation in) or manipulate the expression of one or more target genes, and differentiated into, e.g., a T cell, e.g., a CD8+ T cell (e.g., a CD8+ naive T cell, central memory T cell, or effector memory T cell), a CD4+ T cell, a stem cell memory T cell, a lymphoid progenitor cell or a hematopoietic stem cell.

In some embodiments, the cells include one or more subsets of T cells or other cell types, such as whole T cell populations, CD4+ cells, CD8+ cells, and subpopulations thereof, such as those defined by function, activation state, maturity, potential for differentiation, expansion, recirculation, localization, and/or persistence capacities, antigen-specificity, type of antigen receptor, presence in a particular organ or compartment, marker or cytokine secretion profile, and/or degree of differentiation. Among the sub-types and subpopulations of T cells and/or of CD4+ and/or of CD8+ T cells are naive T (TN) cells, effector T cells (TEFF), memory T cells and sub-types thereof, such as stem cell memory T (TSCM), central memory T (TCM), effector memory T (TEM), or terminally differentiated effector memory T cells, tumor-infiltrating lymphocytes (TIL), immature T cells, mature T cells, helper T cells, cytotoxic T cells, mucosa-associated invariant T (MAIT) cells, naturally occurring and adaptive regulatory T (Treg) cells, helper T cells, such as TH1 cells, TH2 cells, TH3 cells, TH17 cells, TH9 cells, TH22 cells, follicular helper T cells, alpha/beta T cells, and delta/gamma T cells. In certain embodiments, any number of T cell lines available in the art, may be used.

In some embodiments, the methods include isolating immune cells from the subject, preparing, processing, culturing, and/or engineering them. In some embodiments, preparation of the engineered cells includes one or more culture and/or preparation steps. The cells for engineering as described may be isolated from a sample, such as a biological sample, e.g., one obtained from or derived from a subject. In some embodiments, the subject from which the cell is isolated is one having the disease or condition or in need of a cell therapy or to which cell therapy will be administered. The subject in some embodiments is a human in need of a particular therapeutic intervention, such as the adoptive cell therapy for which cells are being isolated, processed, and/or engineered. Accordingly, the cells in some embodiments are primary cells, e.g., primary human cells. The samples include tissue, fluid, and other samples taken directly from the subject, as well as samples resulting from one or more processing steps, such as separation, centrifugation, genetic engineering (e.g. transduction with viral vector), washing, and/or incubation. The biological sample can be a sample obtained directly from a biological source or a sample that is processed. Biological samples include, but are not limited to, body fluids, such as blood, plasma, serum, cerebrospinal fluid, synovial fluid, urine and sweat, tissue and organ samples, including processed samples derived therefrom.

In some aspects, the sample from which the cells are derived or isolated is blood or a blood-derived sample, or is or is derived from an apheresis or leukapheresis product. Exemplary samples include whole blood, peripheral blood mononuclear cells (PBMCs), leukocytes, bone marrow, thymus, tissue biopsy, tumor, leukemia, lymphoma, lymph node, gut associated lymphoid tissue, mucosa associated lymphoid tissue, spleen, other lymphoid tissues, liver, lung, stomach, intestine, colon, kidney, pancreas, breast, bone, prostate, cervix, testes, ovaries, tonsil, or other organ, and/or cells derived therefrom. Samples include, in the context of cell therapy, e.g., adoptive cell therapy, samples from autologous and allogeneic sources.

In some embodiments, the cells are derived from cell lines, e.g., T cell lines. The cells in some embodiments are obtained from a xenogeneic source, for example, from mouse, rat, non-human primate, and pig. In some embodiments, isolation of the cells includes one or more preparation and/or non-affinity based cell separation steps. In some examples, cells are washed, centrifuged, and/or incubated in the presence of one or more reagents, for example, to remove unwanted components, enrich for desired components, lyse or remove cells sensitive to particular reagents. In some examples, cells are separated based on one or more property, such as density, adherent properties, size, sensitivity and/or resistance to particular components.

In some examples, cells from the circulating blood of a subject are obtained, e.g., by apheresis or leukapheresis. The samples, in some aspects, contain lymphocytes, including T cells, monocytes, granulocytes, B cells, other nucleated white blood cells, red blood cells, and/or platelets, and in some aspects contains cells other than red blood cells and platelets. In some embodiments, the blood cells collected from the subject are washed, e.g., to remove the plasma fraction and to place the cells in an appropriate buffer or media for subsequent processing steps. In some embodiments, the cells are washed with phosphate buffered saline (PBS). In some aspects, a washing step is accomplished by tangential flow filtration (TFF) according to the manufacturer's instructions. In some embodiments, the cells are resuspended in a variety of biocompatible buffers after washing. In certain embodiments, components of a blood cell sample are removed and the cells directly resuspended in culture media. In some embodiments, the methods include density-based cell separation methods, such as the preparation of white blood cells from peripheral blood by lysing the red blood cells and centrifugation through a Percoll or Ficoll gradient.

In one embodiment, immune are obtained cells from the circulating blood of an individual are obtained by apheresis or leukapheresis. The apheresis product typically contains lymphocytes, including T cells, monocytes, granulocytes, B cells, other nucleated white blood cells, red blood cells, and platelets. The cells collected by apheresis may be washed to remove the plasma fraction and to place the cells in an appropriate buffer or media, such as phosphate buffered saline (PBS) or wash solution lacks calcium and may lack magnesium or may lack many if not all divalent cations, for subsequent processing steps. After washing, the cells may be resuspended in a variety of biocompatible buffers, such as, for example, Ca-free, Mg-free PBS. Alternatively, the undesirable components of the apheresis sample may be removed and the cells directly resuspended in culture media.

In some embodiments, the isolation methods include the separation of different cell types based on the expression or presence in the cell of one or more specific molecules, such as surface markers, e.g., surface proteins, intracellular markers, or nucleic acid. In some embodiments, any known method for separation based on such markers may be used. In some embodiments, the separation is affinity- or immunoaffinity-based separation. For example, the isolation in some aspects includes separation of cells and cell populations based on the cells' expression or expression level of one or more markers, typically cell surface markers, for example, by incubation with an antibody or binding partner that specifically binds to such markers, followed generally by washing steps and separation of cells having bound the antibody or binding partner, from those cells having not bound to the antibody or binding partner.

Such separation steps can be based on positive selection, in which the cells having bound the reagents are retained for further use, and/or negative selection, in which the cells having not bound to the antibody or binding partner are retained. In some examples, both fractions are retained for further use. In some aspects, negative selection can be particularly useful where no antibody is available that specifically identifies a cell type in a heterogeneous population, such that separation is best carried out based on markers expressed by cells other than the desired population. The separation need not result in 100% enrichment or removal of a particular cell population or cells expressing a particular marker. For example, positive selection of or enrichment for cells of a particular type, such as those expressing a marker, refers to increasing the number or percentage of such cells, but need not result in a complete absence of cells not expressing the marker. Likewise, negative selection, removal, or depletion of cells of a particular type, such as those expressing a marker, refers to decreasing the number or percentage of such cells, but need not result in a complete removal of all such cells.

In some examples, multiple rounds of separation steps are carried out, where the positively or negatively selected fraction from one step is subjected to another separation step, such as a subsequent positive or negative selection. In some examples, a single separation step can deplete cells expressing multiple markers simultaneously, such as by incubating cells with a plurality of antibodies or binding partners, each specific for a marker targeted for negative selection. Likewise, multiple cell types can simultaneously be positively selected by incubating cells with a plurality of antibodies or binding partners expressed on the various cell types.

In some embodiments, one or more of the T cell populations is enriched for or depleted of cells that are positive for (marker+) or express high levels (marker$^{high}$) of one or more particular markers, such as surface markers, or that are negative for (marker−) or express relatively low levels (marker$^{low}$) of one or more markers. For example, in some aspects, specific subpopulations of T cells, such as cells positive or expressing high levels of one or more surface markers, e.g., CD28+, CD62L+, CCR7+, CD27+, CD127+, CD4+, CD8+, CD45RA+, and/or CD45RO+ T cells, are isolated by positive or negative selection techniques. In some cases, such markers are those that are absent or expressed at relatively low levels on certain populations of T cells (such as non-memory cells) but are present or expressed at relatively higher levels on certain other populations of T cells (such as memory cells). In one embodiment, the cells (such as the CD8+ cells or the T cells, e.g., CD3+ cells) are enriched for (i.e., positively selected for) cells that are positive or expressing high surface levels of CD45RO, CCR7, CD28, CD27, CD44, CD 127, and/or CD62L and/or depleted of (e.g., negatively selected for) cells that are positive for or express high surface levels of CD45RA. In some embodiments, cells are enriched for or depleted of cells positive or expressing high surface levels of CD 122, CD95, CD25, CD27, and/or IL7-Ra (CD 127). In some examples, CD8+ T cells are enriched for cells positive for CD45RO (or negative for CD45RA) and for CD62L. For example, CD3+, CD28+ T cells can be positively selected using CD3/CD28 conjugated magnetic beads (e.g., DYNA-BEADS® M-450 CD3/CD28 T Cell Expander).

In some embodiments, T cells are separated from a PBMC sample by negative selection of markers expressed on non-T cells, such as B cells, monocytes, or other white blood cells, such as CD 14. In some aspects, a CD4+ or CD8+ selection step is used to separate CD4+ helper and CD8+ cytotoxic T cells. Such CD4+ and CD8+ populations can be further sorted into sub-populations by positive or negative selection for markers expressed or expressed to a relatively higher degree on one or more naive, memory, and/or effector T cell subpopulations. In some embodiments, CD8+ cells are further enriched for or depleted of naive, central memory, effector memory, and/or central memory stem cells, such as by positive or negative selection based on surface antigens associated with the respective subpopulation. In some embodiments, enrichment for central memory T (TCM) cells is carried out to increase efficacy, such as to improve long-term survival, expansion, and/or engraftment following administration, which in some aspects is particularly robust in such sub-populations. In some embodiments, combining TCM-enriched CD8+ T cells and CD4+ T cells further enhances efficacy.

In some embodiments, memory T cells are present in both CD62L+ and CD62L− subsets of CD8+ peripheral blood lymphocytes. PBMC can be enriched for or depleted of CD62L-CD8+ and/or CD62L+CD8+ fractions, such as using anti-CD8 and anti-CD62L antibodies. In some embodiments, a CD4+ T cell population and a CD8+ T cell sub-population, e.g., a sub-population enriched for central memory (TCM) cells. In some embodiments, the enrichment for central memory T (TCM) cells is based on positive or high surface expression of CD45RO, CD62L, CCR7, CD28, CD3, and/or CD 127; in some aspects, it is based on negative selection for cells expressing or highly expressing CD45RA and/or granzyme B. In some aspects, isolation of a CD8+ population enriched for TCM cells is carried out by depletion of cells expressing CD4, CD 14, CD45RA, and positive selection or enrichment for cells expressing CD62L. In one aspect, enrichment for central memory T (TCM) cells is carried out starting with a negative fraction of cells selected based on CD4 expression, which is subjected to a negative selection based on expression of CD 14 and CD45RA, and a positive selection based on CD62L. Such selections in some aspects are carried out simultaneously and in other aspects are carried out sequentially, in either order. In some aspects, the same CD4 expression-based selection step used in preparing the CD8+ cell population or subpopulation, also is used to generate the CD4+ cell population or sub-population, such that both the positive and negative fractions from the CD4-based separation are retained and used in subsequent steps of the methods, optionally following one or more further positive or negative selection steps.

CD4+ T helper cells are sorted into naive, central memory, and effector cells by identifying cell populations that have cell surface antigens. CD4+ lymphocytes can be obtained by standard methods. In some embodiments, naive CD4+ T lymphocytes are CD45RO−, CD45RA+, CD62L+, CD4+ T cells. In some embodiments, central memory CD4+ cells are CD62L+ and CD45RO+. In some embodiments, effector CD4+ cells are CD62L− and CD45RO. In one example, to enrich for CD4+ cells by negative selection, a monoclonal antibody cocktail typically includes antibodies to CD14, CD20, CD11b, CD16, HLA-DR, and CD8. In some embodiments, the antibody or binding partner is bound to a solid support or matrix, such as a magnetic bead or paramagnetic bead, to allow for separation of cells for positive and/or negative selection.

In some embodiments, the cells are incubated and/or cultured prior to or in connection with genetic engineering. The incubation steps can include culture, cultivation, stimulation, activation, and/or propagation. In some embodiments, the compositions or cells are incubated in the presence of stimulating conditions or a stimulatory agent. Such conditions include those designed to induce proliferation, expansion, activation, and/or survival of cells in the population, to mimic antigen exposure, and/or to prime the cells for genetic engineering, such as for the introduction of a recombinant antigen receptor. The conditions can include one or more of particular media, temperature, oxygen content, carbon dioxide content, time, agents, e.g., nutrients, amino acids, antibiotics, ions, and/or stimulatory factors, such as cytokines, chemokines, antigens, binding partners, fusion proteins, recombinant soluble receptors, and any other agents designed to activate the cells. In some embodiments, the stimulating conditions or agents include one or more agent, e.g., ligand, which is capable of activating an intracellular signaling domain of a TCR complex. In some aspects, the agent turns on or initiates TCR/CD3 intracellular signaling cascade in a T cell. Such agents can include antibodies, such as those specific for a TCR component and/or costimulatory receptor, e.g., anti-CD3, anti-CD28, for example, bound to solid support such as a bead, and/or one or more cytokines. Optionally, the expansion method may further comprise the step of adding anti-CD3 and/or anti CD28 antibody to the culture medium (e.g., at a concentration of at least about 0.5 ng/ml). In some embodiments, the stimulating agents include IL-2 and/or IL-15, for example, an IL-2 concentration of at least about 10 units/ mL.

In another embodiment, T cells are isolated from peripheral blood by lysing the red blood cells and depleting the monocytes, for example, by centrifugation through a PER-COLL™ gradient. Alternatively, T cells can be isolated from an umbilical cord. In any event, a specific subpopulation of T cells can be further isolated by positive or negative selection techniques.

The cord blood mononuclear cells so isolated can be depleted of cells expressing certain antigens, including, but not limited to, CD34, CD8, CD14, CD19, and CD56. Depletion of these cells can be accomplished using an isolated antibody, a biological sample comprising an antibody, such as ascites, an antibody bound to a physical support, and a cell bound antibody.

Enrichment of a T cell population by negative selection can be accomplished using a combination of antibodies directed to surface markers unique to the negatively selected cells. A preferred method is cell sorting and/or selection via negative magnetic immunoadherence or flow cytometry that uses a cocktail of monoclonal antibodies directed to cell surface markers present on the cells negatively selected. For example, to enrich for CD4; cells by negative selection, a monoclonal antibody cocktail typically includes antibodies to CD14, CD20, CD11b, CD16, HLA-DR, and CD8.

For isolation of a desired population of cells by positive or negative selection, the concentration of cells and surface (e.g., particles such as beads) can be varied. In certain embodiments, it may be desirable to significantly decrease the volume in which beads and cells are mixed together (i.e., increase the concentration of cells), to ensure maximum contact of cells and beads. For example, in one embodiment, a concentration of 2 billion cells/ml is used. In one embodiment, a concentration of 1 billion cells/ml is used. In a further embodiment, greater than 100 million cells/ml is used. In a further embodiment, a concentration of cells of 10, 15, 20, 25, 30, 35, 40, 45, or 50 million cells/ml is used. In yet another embodiment, a concentration of cells from 75, 80, 85, 90, 95, or 100 million cells/ml is used. In further embodiments, concentrations of 125 or 150 million cells/ml can be used. Using high concentrations can result in increased cell yield, cell activation, and cell expansion.

T cells can also be frozen after the washing step, which does not require the monocyte-removal step. While not wishing to be bound by theory, the freeze and subsequent thaw step provides a more uniform product by removing granulocytes and to some extent monocytes in the cell population. After the washing step that removes plasma and platelets, the cells may be suspended in a freezing solution. While many freezing solutions and parameters are known in the art and will be useful in this context, in a non-limiting example, one method involves using PBS containing 20% DMSO and 8% human serum albumin, or other suitable cell freezing media. The cells are then frozen to −80° C. at a rate of 1° C. per minute and stored in the vapor phase of a liquid nitrogen storage tank. Other methods of controlled freezing may be used as well as uncontrolled freezing immediately at −20° C. or in liquid nitrogen.

In one embodiment, the population of T cells is comprised within cells such as peripheral blood mononuclear cells, cord blood cells, a purified population of T cells, and a T cell line. In another embodiment, peripheral blood mononuclear cells comprise the population of T cells. In yet another embodiment, purified T cells comprise the population of T cells.

In certain embodiments, T regulatory cells (Tregs) can be isolated from a sample. The sample can include, but is not limited to, umbilical cord blood or peripheral blood. In certain embodiments, the Tregs are isolated by flow-cytometry sorting. The sample can be enriched for Tregs prior to isolation by any means known in the art. The isolated Tregs can be cryopreserved, and/or expanded prior to use. Methods for isolating Tregs are described in U.S. Pat. Nos. 7,754,482, 8,722,400, and 9,555,105, and U.S. patent application Ser. No. 13/639,927, contents of which are incorporated herein in their entirety.

H. Expansion of Immune Cells

Whether prior to or after modification of cells to express a CAR, the cells can be activated and expanded in number using methods as described, for example, in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 5,883,223; 6,905,874; 6,797,514; 6,867,041; and U.S. Publication No. 20060121005. For example, the T cells of the invention may be expanded by contact with a surface having attached thereto an agent that stimulates a CD3/TCR complex associated signal and a ligand that stimulates a co-stimulatory molecule on the surface of the T cells. In particular, T cell populations may be stimulated by contact with an anti-CD3 antibody, or antigen-binding fragment thereof, or an anti-CD2 antibody immobilized on a surface, or by contact with a protein kinase C activator (e.g., bryostatin) in conjunction with a calcium ionophore. For co-stimulation of an accessory molecule on the surface of the T cells, a ligand that binds the accessory molecule is used. For example, T cells can be contacted with an anti-CD3 antibody and an anti-CD28 antibody, under conditions appropriate for stimulating proliferation of the T cells. Examples of an anti-CD28 antibody include 9.3, B-T3, XR-CD28 (Diaclone, Besancon, France) and these can be used in the invention, as can other methods and reagents known in the art (see, e.g., ten Berge et al., Transplant Proc. (1998) 30(8): 3975-3977; Haanen et al., J. Exp. Med. (1999) 190(9): 1319-1328; and Garland et al., J. Immunol. Methods (1999) 227(1-2): 53-63).

Expanding T cells by the methods disclosed herein can be multiplied by about 10 fold, 20 fold, 30 fold, 40 fold, 50 fold, 60 fold, 70 fold, 80 fold, 90 fold, 100 fold, 200 fold, 300 fold, 400 fold, 500 fold, 600 fold, 700 fold, 800 fold, 900 fold, 1000 fold, 2000 fold, 3000 fold, 4000 fold, 5000 fold, 6000 fold, 7000 fold, 8000 fold, 9000 fold, 10,000 fold, 100,000 fold, 1,000,000 fold, 10,000,000 fold, or greater, and any and all whole or partial integers therebetween. In one embodiment, the T cells expand in the range of about 20 fold to about 50 fold.

Following culturing, the T cells can be incubated in cell medium in a culture apparatus for a period of time or until the cells reach confluency or high cell density for optimal passage before passing the cells to another culture apparatus. The culturing apparatus can be of any culture apparatus commonly used for culturing cells in vitro. Preferably, the level of confluence is 70% or greater before passing the cells to another culture apparatus. More preferably, the level of confluence is 90% or greater. A period of time can be any time suitable for the culture of cells in vitro. The T cell medium may be replaced during the culture of the T cells at any time. Preferably, the T cell medium is replaced about every 2 to 3 days. The T cells are then harvested from the culture apparatus whereupon the T cells can be used immediately or cryopreserved to be stored for use at a later time. In one embodiment, the invention includes cryopreserving the expanded T cells. The cryopreserved T cells are thawed prior to introducing nucleic acids into the T cell.

In another embodiment, the method comprises isolating T cells and expanding the T cells. In another embodiment, the invention further comprises cryopreserving the T cells prior to expansion. In yet another embodiment, the cryopreserved T cells are thawed for electroporation with the RNA encoding the chimeric membrane protein.

Another procedure for ex vivo expansion cells is described in U.S. Pat. No. 5,199,942 (incorporated herein by reference). Expansion, such as described in U.S. Pat. No. 5,199,942 can be an alternative or in addition to other methods of expansion described herein. Briefly, ex vivo culture and expansion of T cells comprises the addition to the cellular growth factors, such as those described in U.S. Pat. No. 5,199,942, or other factors, such as flt3-L, IL-1, IL-3 and c-kit ligand. In one embodiment, expanding the T cells comprises culturing the T cells with a factor selected from the group consisting of flt3-L, IL-1, IL-3 and c-kit ligand.

The culturing step as described herein (contact with agents as described herein or after electroporation) can be very short, for example less than 24 hours such as 1, 2, 3, 4, 5, 6, 7, 8, 9, 10, 11, 12, 13, 14, 15, 16, 17, 18, 19, 20, 21, 22, or 23 hours. The culturing step as described further herein (contact with agents as described herein) can be longer, for example 1, 2, 3, 4, 5, 6, 7, 8, 9, 10, 11, 12, 13, 14, or more days.

Various terms are used to describe cells in culture. Cell culture refers generally to cells taken from a living organism and grown under controlled condition. A primary cell culture is a culture of cells, tissues or organs taken directly from an organism and before the first subculture. Cells are expanded in culture when they are placed in a growth medium under conditions that facilitate cell growth and/or division, resulting in a larger population of the cells. When cells are expanded in culture, the rate of cell proliferation is typically measured by the amount of time required for the cells to double in number, otherwise known as the doubling time.

Each round of subculturing is referred to as a passage. When cells are subcultured, they are referred to as having been passaged. A specific population of cells, or a cell line, is sometimes referred to or characterized by the number of times it has been passaged. For example, a cultured cell population that has been passaged ten times may be referred to as a P10 culture. The primary culture, i.e., the first culture following the isolation of cells from tissue, is designated P0. Following the first subculture, the cells are described as a secondary culture (P1 or passage 1). After the second subculture, the cells become a tertiary culture (P2 or passage 2), and so on. It will be understood by those of skill in the art that there may be many population doublings during the period of passaging; therefore the number of population doublings of a culture is greater than the passage number. The expansion of cells (i.e., the number of population doublings) during the period between passaging depends on many factors, including but is not limited to the seeding density, substrate, medium, and time between passaging.

In one embodiment, the cells may be cultured for several hours (about 3 hours) to about 14 days or any hourly integer value in between. Conditions appropriate for T cell culture include an appropriate media (e.g., Minimal Essential Media or RPMI Media 1640 or, X-vivo 15, (Lonza)) that may contain factors necessary for proliferation and viability, including serum (e.g., fetal bovine or human serum), interleukin-2 (IL-2), insulin, IFN-gamma, IL-4, IL-7, GM-CSF, IL-10, IL-12, IL-15, TGF-beta, and TNF-$\alpha$ or any other additives for the growth of cells known to the skilled artisan. Other additives for the growth of cells include, but are not limited to, surfactant, plasmanate, and reducing agents such as N-acetyl-cysteine and 2-mercaptoethanol. Media can include RPMI 1640, AIM-V, DMEM, MEM, $\alpha$-MEM, F-12, X-Vivo 15, and X-Vivo 20, Optimizer, with added amino acids, sodium pyruvate, and vitamins, either serum-free or supplemented with an appropriate amount of serum (or plasma) or a defined set of hormones, and/or an amount of cytokine(s) sufficient for the growth and expansion of T cells. Antibiotics, e.g., penicillin and streptomycin, are included only in experimental cultures, not in cultures of cells that are to be infused into a subject. The target cells are maintained under conditions necessary to support growth, for example, an appropriate temperature (e.g., 37° C.) and atmosphere (e.g., air plus 5% $CO_2$).

The medium used to culture the T cells may include an agent that can co-stimulate the T cells. For example, an agent that can stimulate CD3 is an antibody to CD3, and an agent that can stimulate CD28 is an antibody to CD28. A cell isolated by the methods disclosed herein can be expanded approximately 10 fold, 20 fold, 30 fold, 40 fold, 50 fold, 60 fold, 70 fold, 80 fold, 90 fold, 100 fold, 200 fold, 300 fold, 400 fold, 500 fold, 600 fold, 700 fold, 800 fold, 900 fold, 1000 fold, 2000 fold, 3000 fold, 4000 fold, 5000 fold, 6000 fold, 7000 fold, 8000 fold, 9000 fold, 10,000 fold, 100,000 fold, 1,000,000 fold, 10,000,000 fold, or greater. In one embodiment, the T cells expand in the range of about 20 fold to about 50 fold, or more. In one embodiment, human T regulatory cells are expanded via anti-CD3 antibody coated KT64.86 artificial antigen presenting cells (aAPCs). Methods for expanding and activating T cells can be found in U.S. Pat. Nos. 7,754,482, 8,722,400, and 9,555,105, contents of which are incorporated herein in their entirety.

In one embodiment, the method of expanding the T cells can further comprise isolating the expanded T cells for further applications. In another embodiment, the method of expanding can further comprise a subsequent electroporation of the expanded T cells followed by culturing. The subsequent electroporation may include introducing a nucleic acid encoding an agent, such as a transducing the expanded T cells, transfecting the expanded T cells, or electroporating the expanded T cells with a nucleic acid, into the expanded population of T cells, wherein the agent further stimulates the T cell. The agent may stimulate the T cells, such as by stimulating further expansion, effector function, or another T cell function.

I. Pharmaceutical Compositions and Formulations

Also provided are populations of immune cells of the invention, and compositions containing such cells. Among the compositions are pharmaceutical compositions and formulations for administration, such as for adoptive cell therapy. Also provided are therapeutic methods for administering the cells and compositions to subjects, e.g., patients.

Also provided are compositions including the cells for administration, including pharmaceutical compositions and formulations, such as unit dose form compositions including the number of cells for administration in a given dose or fraction thereof. The pharmaceutical compositions and formulations generally include one or more optional pharmaceutically acceptable carrier or excipient. In some embodiments, the composition includes at least one additional therapeutic agent.

The term "pharmaceutical formulation" refers to a preparation which is in such form as to permit the biological activity of an active ingredient contained therein to be effective, and which contains no additional components which are unacceptably toxic to a subject to which the formulation would be administered. A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative. In some aspects, the choice of carrier is determined in part by the particular cell and/or by the method of administration. Accordingly, there are a variety of suitable formulations. For example, the pharmaceutical composition can contain preservatives. Suitable preservatives may include, for example, methylparaben, propylparaben, sodium benzoate, and benzalkonium chloride. In some aspects, a mixture of two or more preservatives is used. The preservative or mixtures thereof are typically present in an amount of about 0.0001% to about 2% by weight of the total composition. Carriers are described, e.g., by Remington's Pharmaceutical Sciences 16th edition, Osol, A. Ed. (1980). Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG).

Buffering agents in some aspects are included in the compositions. Suitable buffering agents include, for example, citric acid, sodium citrate, phosphoric acid, potassium phosphate, and various other acids and salts. In some aspects, a mixture of two or more buffering agents is used. The buffering agent or mixtures thereof are typically present in an amount of about 0.001% to about 4% by weight of the total composition. Methods for preparing administrable pharmaceutical compositions are known. Exemplary methods are described in more detail in, for example, Remington: The Science and Practice of Pharmacy, Lippincott Williams & Wilkins; 21st ed. (May 1, 2005).

The formulations can include aqueous solutions. The formulation or composition may also contain more than one active ingredient useful for the particular indication, disease, or condition being treated with the cells, preferably those with activities complementary to the cells, where the respective activities do not adversely affect one another. Such active ingredients are suitably present in combination in amounts that are effective for the purpose intended. Thus, in some embodiments, the pharmaceutical composition further includes other pharmaceutically active agents or drugs, such as chemotherapeutic agents, e.g., asparaginase, busulfan, carboplatin, cisplatin, daunorubicin, doxorubicin, fluorouracil, gemcitabine, hydroxyurea, methotrexate, paclitaxel, rituximab, vinblastine, and/or vincristine. The pharmaceutical composition in some embodiments contains the cells in amounts effective to treat or prevent the disease or condition, such as a therapeutically effective or prophylactically effective amount. Therapeutic or prophylactic efficacy in some embodiments is monitored by periodic assessment of treated subjects. The desired dosage can be delivered by a single bolus administration of the cells, by multiple bolus administrations of the cells, or by continuous infusion administration of the cells.

Formulations include those for oral, intravenous, intraperitoneal, subcutaneous, pulmonary, transdermal, intramuscular, intranasal, buccal, sublingual, or suppository administration. In some embodiments, the cell populations are administered parenterally. The term "parenteral," as used herein, includes intravenous, intramuscular, subcutaneous, rectal, vaginal, and intraperitoneal administration. In some embodiments, the cells are administered to the subject using peripheral systemic delivery by intravenous, intraperitoneal, or subcutaneous injection. Compositions in some embodiments are provided as sterile liquid preparations, e.g., isotonic aqueous solutions, suspensions, emulsions, dispersions, or viscous compositions, which may in some aspects be buffered to a selected pH. Liquid preparations are normally easier to prepare than gels, other viscous compositions, and solid compositions. Additionally, liquid compositions are somewhat more convenient to administer, especially by injection. Viscous compositions, on the other hand, can be formulated within the appropriate viscosity range to provide longer contact periods with specific tissues. Liquid or viscous compositions can comprise carriers, which can be a solvent or dispersing medium containing, for example, water, saline, phosphate buffered saline, polyoi (for example, glycerol, propylene glycol, liquid polyethylene glycol) and suitable mixtures thereof.

Sterile injectable solutions can be prepared by incorporating the cells in a solvent, such as in admixture with a suitable carrier, diluent, or excipient such as sterile water, physiological saline, glucose, dextrose, or the like. The compositions can contain auxiliary substances such as wetting, dispersing, or emulsifying agents (e.g., methylcellulose), pH buffering agents, gelling or viscosity enhancing additives, preservatives, flavoring agents, and/or colors, depending upon the route of administration and the preparation desired. Standard texts may in some aspects be consulted to prepare suitable preparations.

Various additives which enhance the stability and sterility of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, and sorbic acid. Prolonged absorption of the injectable pharmaceutical form can be brought about by the use of agents delaying absorption, for example, aluminum monostearate and gelatin.

The formulations to be used for in vivo administration are generally sterile. Sterility may be readily accomplished, e.g., by filtration through sterile filtration membranes.

The contents of the articles, patents, and patent applications, and all other documents and electronically available information mentioned or cited herein, are hereby incorporated by reference in their entirety to the same extent as if each individual publication was specifically and individually indicated to be incorporated by reference. Applicants reserve the right to physically incorporate into this application any and all materials and information from any such articles, patents, patent applications, or other physical and electronic documents.

While the present invention has been described with reference to the specific embodiments thereof, it should be understood by those skilled in the art that various changes may be made and equivalents may be substituted without departing from the true spirit and scope of the invention. It will be readily apparent to those skilled in the art that other suitable modifications and adaptations of the methods described herein may be made using suitable equivalents without departing from the scope of the embodiments disclosed herein. In addition, many modifications may be made to adapt a particular situation, material, composition of matter, process, process step or steps, to the objective, spirit and scope of the present invention. All such modifications are intended to be within the scope of the claims appended hereto. Having now described certain embodiments in detail, the same will be more clearly understood by reference to the following examples, which are included for purposes of illustration only and are not intended to be limiting.

EXPERIMENTAL EXAMPLES

The invention is now described with reference to the following Examples. These Examples are provided for the purpose of illustration only, and the invention is not limited to these Examples, but rather encompasses all variations that are evident as a result of the teachings provided herein.

The materials and methods of the experimental examples are now described.

Cells: All cells were cultured at 37° C. in complete media (CM, RPMI 1640 GlutaMAX, 10% fetal bovine serum, 100 U/mL penicillin, 100 mg/mL streptomycin) and regularly validated to be mycoplasma free. Lentivirus packaging was performed in the immortalized normal fetal renal 293T cell line purchased from ATCC. Ovarian carcinoma cell line C30 was transduced with a lentiviral vector encoding human MISIIR cDNA (Origene, catalog no. RC212425) to generate C30.MISIIR. AN3Ca was purchased from the ATCC. All of the cell lines were stably transduced with GFP-2A-firefly luciferase (fLuc) lentiviral vector. WO19 primary tumor cultures were established from tumor obtained from patients after being passaged in mice in order to expand the tumor as described. WO12 primary tumor cultures were established from tumor obtained from patients at the time of OC debulking surgeries as previously described. Primary tumor cells were grown on Primaria tissue culture flasks (Corning) in hypoxic conditions until required for in vitro experiments.

Anti-MISIIR CAR Construction: All scFvs were polymerase chain reaction (PCR) amplified using the following paired primers:

```
                                        (SEQ ID NO: 35)
TATGGATCCGCC CAGGTGCAGCTGGTGCAGTCTGGAAC
(BamHI)
and (SEQ ID NO: 36)
TAT GCTAGCCGAGGGGGCGGCCTTGGGCTGACCTAG;
(NheI)

(SEQ ID NO: 37)
TATGGATCCGCCCAGGTGCAGCTGGTGGAGTCTGGG
(BamHI)
and (SEQ ID NO: 38)
TATGCTAGCACGTTTGATCTCCAGCTTGG TCCCTCCGC;
(NheI)

(SEQ ID NO: 39)
TATTGATCAGCCGAGGTGCAGCT GGTGCAGTCTGGG
(BclI)
and
```

-continued (SEQ ID NO: 40)
TATGCTAGCCGAGTGGG CAGCCTTGGGCTGACCGAG;
(NheI)

(SEQ ID NO: 41)
TATGGATCCGCC GAGGTGCAGCTGGTGGAGTCTGGG
(BamHI)
and (SEQ ID NO: 42)
TATGCTAGCCGAGGGGGCAGCCTTGGGCTGACCTAGG.
(NheI)

The PCR product was digested and ligated into previously described third-generation pELNS lentiviral vectors containing CD27-CD3Z signaling domains. The resulting constructs were designated pELNS-GM7-27Z, pELNS-GS45-27Z, pELNS-1A-27Z, and pELNS-7A-27Z. pELNS-CD19-27Z was also previously described. A pELNS-GM7-AZ construct, lacking the signaling domains but maintaining the extracellular scFv portion, the transmembrane domain, and a non-functional 5-aa-long intracellular tail, was generated as reported previously. Lentiviral vectors were produced in 293T cells as previously described.

Generation of CAR T Cells: Primary lymphocytes from normal donors were obtained from the University of Pennsylvania Human Immunology Core. T cells were stimulated, transduced, and expanded as previously described. Briefly, CD4 and CD8 T cells were mixed at 1:1 ratio and activated with CD3/CD28 Dynabeads (Invitrogen, Carlsbad, CA, USA) at a bead-to-cell ratio of 3:1. 24 h after activation, T cells were transduced with lentiviral vectors at an MOI of 10 and expanded in CM with IU/mL human IL-2 (Proleukin, Prometheus Laboratories, San Diego, CA, USA) for 10-14 days. Cell size was monitored using a Multisizer-Coulter Counter (Beckman Coulter, Brea, CA, USA). Rested T cells (<300 fL) were cryopreserved or used for functional in vitro and in vivo assays.

Flow Cytometric Analysis: All samples for flow cytometry were labeled in 100 mL of staining buffer (phosphate-buffered saline, 2% fetal bovine serum) at 4° C. In all analyses, singlets were gated on using forward scatter height (FSC-H) versus forward scatter area (FSC-A), followed by gating based on forward versus side scatter characteristics. All experiments were conducted on a BD LSRFortessa flow cytometer (Becton Dickinson, Franklin Lakes, NJ, USA) and analyzed with FlowJo v10 (BD Biosciences, Franklin Lakes, NJ, USA). For all experiments, T cell suspensions were stained with fixable Live/Dead aqua stain (Invitrogen), followed by surface antibody staining. Expression of CAR proteins was detected using biotinylated rabbit anti-human IgG (H+L) (Jackson ImmunoResearch, West Grove, PA, USA; catalog no. 309-065-003), biotinylated recombinant MISIIR, or recombinant control protein FR~ (R&D Systems, Minneapolis, MN, USA), followed by streptavidin-allophycocyanin (APC) (BD Biosciences, Franklin Lakes, NJ, USA; catalog no. 554067). Expression of MISIIR in engineered C30.MISIIR cells was assessed by anti-DYKDDDDK-APC (SEQ ID NO:43) (Miltenyi Biotec, Bergisch Gladbach, Germany; catalog no. 130-101-564). The following antibodies against human molecules were used: anti-CD3-Brilliant Violet (BV)605 (catalog no. 317321), anti-CD3-peridinin chlorophyll protein (PerCP)/Cy5.5 (catalog no. 300327), anti-CD4-fluorescein isothio-cyanate (FITC) (catalog no. 317408), anti-CD4-BV421 (catalog no. 317433), anti-CD8-APC (catalog no. 300911), anti-CD69-Pacific Blue (catalog no. 310919), anti-CD137- phycoerythrin (PE)/Cy7 (catalog no. 309817), and anti-TNF-α-BV650 (catalog no. 502928) from BioLegend (San Diego, CA, USA); anti-CD107a-Alexa Fluor 700 (Alexa700) (catalog no. 561340) and anti-CD8-APC-H7 (catalog no. 561423) from BD Biosciences (Franklin Lakes, NJ, USA); and anti-CD45-PE (catalog no. 12-9459-42), anti-IFN-γ-PE (catalog no. 12-7319-42), and anti-IL-2-PerCP-eFluor 710 (catalog no. 46-7029-42) from eBioscience (Waltham, MA, USA).

In Vitro Co-culture Experiments: Cytokine release assays were performed by co-culture of $1\times10^5$ T cells with either soluble recombinant MISIIR protein at increasing concentrations, or $1\times10^5$ target cells per well in triplicate in 96-well plates in a final volume of 200 mL of CM. After 24 h, co-culture supernatants were assayed for the presence of IFN-γ using an ELISA kit, according to the manufacturer's instructions (BioLegend, San Diego, CA, USA). From the same co-cultures, T cells were collected and stained for T cell markers CD3, CD4, and CD8, as well as surface activation markers CD69 and CD137. For apoptosis assays, tumor cells were co-stained with annexin V-APC and propidium iodide (PI) (BioLegend, San Diego, CA, USA; catalog no. 640912), according to the manufacturer's instructions. For intra-cellular staining, $1\times10^5$ CAR T cells were co-cultured with target cells at 1:1 E:T ratio in triplicate in 200 mL of CM in the presence of anti-CD107a antibody and GolgiStop protein transport inhibitor (BD Biosciences, San Diego, CA, USA). After 5 h, cells were stained with Live/Dead, followed by surface markers CD3, CD4 and CD8, and then fixed and permeabilized by using the Cytofix/Cytoperm fixation/permeabilization kit (BD Biosciences, San Diego, CA, USA: catalog no. 554715) according to the manufacturer's instructions. Finally, cells were stained for intracellular cytokines IFN-γ, TNF-α, and IL-2.

Cytotoxicity Assays: Cytotoxic killing of target tumor cells was assessed using the xCELLigence real-time cell analyzer system (ACEA Biosciences, San Diego, CA, USA). Target tumor cells were plated at $1\times10^4$ cells/well in 96-well plates. After overnight cell adherence, T cells were added at the indicated E:T ratios. Cell index (relative cell impedance) was monitored every 20 min and normalized to the maximum cell index value immediately prior to effector-cell plating. Shaded lines reflect the mean of triplicate wells±SD. Cytotoxicity of CAR T cells cultured with normal primary cells was evaluated in a $^{51}$Cr-release assay. $1\times10^6$ target cells were labeled with $^{51}$Cr (50 mCi) for 1 h at 37° C. $1\times10^4$ labeled target cells were plated in each well of a 96-well plate, and effector cells were added in a volume of 100 μL at the indicated E:T ratios. Cells were co-incubated for 16 h at 37° C., and 30 μL of supernatant was collected and transferred onto the filter of a LumaPlate (PerkinElmer, Waltham, MA, USA). Radioactivity on dried LumaPlate was measured using a β-emission-reading liquid scintillation counter. Percentage specific lysis was determined using the reading of target cells alone and Triton X-100-lysed target cells, corresponding to 0% lysis and 100% lysis, respectively.

Gene-Expression Analysis by RT-PCR: Quantitative real-time PCR was used to analyze expression of MISIR. RNA from frozen cell pellets or tumor samples was extracted with an RNeasy Mini kit (QIAGEN, Hilden, Germany) and reverse transcribed with a high-capacity RNA-to-cDNA kit (Applied Bio-systems, Waltham, MA, USA), according to the manufacturer's in-structions. Quantitative real-time PCR was performed using Taq-Man Universal PCR Master Mix in a ViiA 7 real-time PCR system. The following probes were purchased from Applied Bio-systems: AMHR2 (Hs01086646_g1) and glyceraldehyde-3-phosphate dehydrogenase (GAPDH) (Hs02786624_g1). Target gene expression was calculated by the $2^{-\Delta\Delta CT}$ method for relative quantification after normalization to GAPDH expression.

Xenograft Models: The University of Pennsylvania Institutional Animal Care and Use Committee (IACUC) approved all animal experiments. NSG mice were purchased from The Jackson Laboratory and bred and housed in the vivarium at the University of Pennsylvania in pathogen-free conditions. Xenograft tumors were established by subcutaneous injection of $10\times10^6$ C30.MISIIR, $4\times10^6$ OVCAR3, and $1\times10^6$ OVCAR5 or AN3Ca into the flanks of NSG mice. At indicated days, mice were treated with two intravenous injections of $5\times10^6$ CAR+ T cells on days 0 and 7. Tumors were measured twice a week with caliper, and volumes were calculated as V=½×Length (L)×Width (W)×W. Mice were euthanized when tumor diameter was equivalent to or greater than 2 cm. Bioluminescence imaging was performed by using a Lumina IVIS imaging system and quantified with the Living Image software (PerkinElmer, Waltham, MA, USA). Mice were given an intraperitoneal injection of 150 mg/kg D-luciferin (Caliper Life Sciences, Hopkinton, MA, USA) and imaged under isoflurane anesthesia at the peak of photon emission.

Western Blot: Cells were lysed using radioimmunoprecipitation assay (RIPA) lysis buffer containing protease inhibitor cock-tail (Roche, Basel, Switzerland; catalog no. 5892970001). Protein was quantified using a bicinchoninic acid (BCA) assay (Thermo Scientific, Waltham, MA, USA; catalog no. 23227). 80 µg of protein samples was mixed with Laemmli loading buffer (Bio-Rad, Hercules, CA, USA; catalog no. 161-0737) and 5% β-mercaptoethanol (Bio-Rad, Hercules, CA, USA; catalog no. 60-24-2) and incubated at 95° C. for 5 min. Lysates were loaded in 4%-15% Mini-PROTEAN TGX gels (Bio-Rad, Hercules, CA, USA; catalog no. 456-1033), and gels were run at 150 V for 1 h. A protein ladder (Bio-Rad, Hercules, CA, USA; catalog no. 161-0376) was used. Protein samples were then transferred from gels to a polyvinylidene fluoride (PVDF) membrane (Millipore, Burlington, MA, USA; catalog no. IPVH00010) at 100 V for 1 h. Membranes were blocked and washed with Tris-buffered saline with Tween 20 (TBST) (1% Tween 20) (Bio-Rad, Hercules, CA, USA; catalog no. 170-6435) and incubated with primary human MISIIR antibody (R&D Systems, Minneapolis, MN, USA; catalog no. AF4749) at 0.1 mg/mL and secondary antibody peroxidase-conjugated AffiniPure donkey anti-sheep IgG (H+L) (Jackson ImmunoResearch, West Grove, PA, USA; catalog no. 713-035-147) diluted 1:10,000. Human/mouse/rat GAPDH (R&D Systems, Minneapolis, MN, USA; catalog no. MAB5719) diluted 1:20,000 was used as housekeeping control. Membranes were washed three times in between the primary and secondary antibodies incubation steps. Consequently, membranes were developed using the enhanced chemiluminescence (ECL) prime western blotting detection reagent (GE Healthcare, Chicago, IL, USA; catalog no. RPN2236) and imaged using a GE ImageQuant LAS 4000 series imaging system.

Statistical Analysis: The data are reported as mean±standard deviation (SD) unless otherwise noted. Statistical analysis was performed using one-way ANOVA, two-way ANOVA with a Tukey's or Dunnett's multiple comparisons post hoc test, or unpaired Student's t test when appropriate. In vitro assays were replicated with at least three different normal T cell donors. GraphPad Prism 8.0 software (La Jolla, CA, USA) was used for statistical calculations. $p<0.05$ was considered significant.

The results of the experiments are now described.

Example 1: Generation of Anti-MISIIR CARs

Figures 1A, 1B:
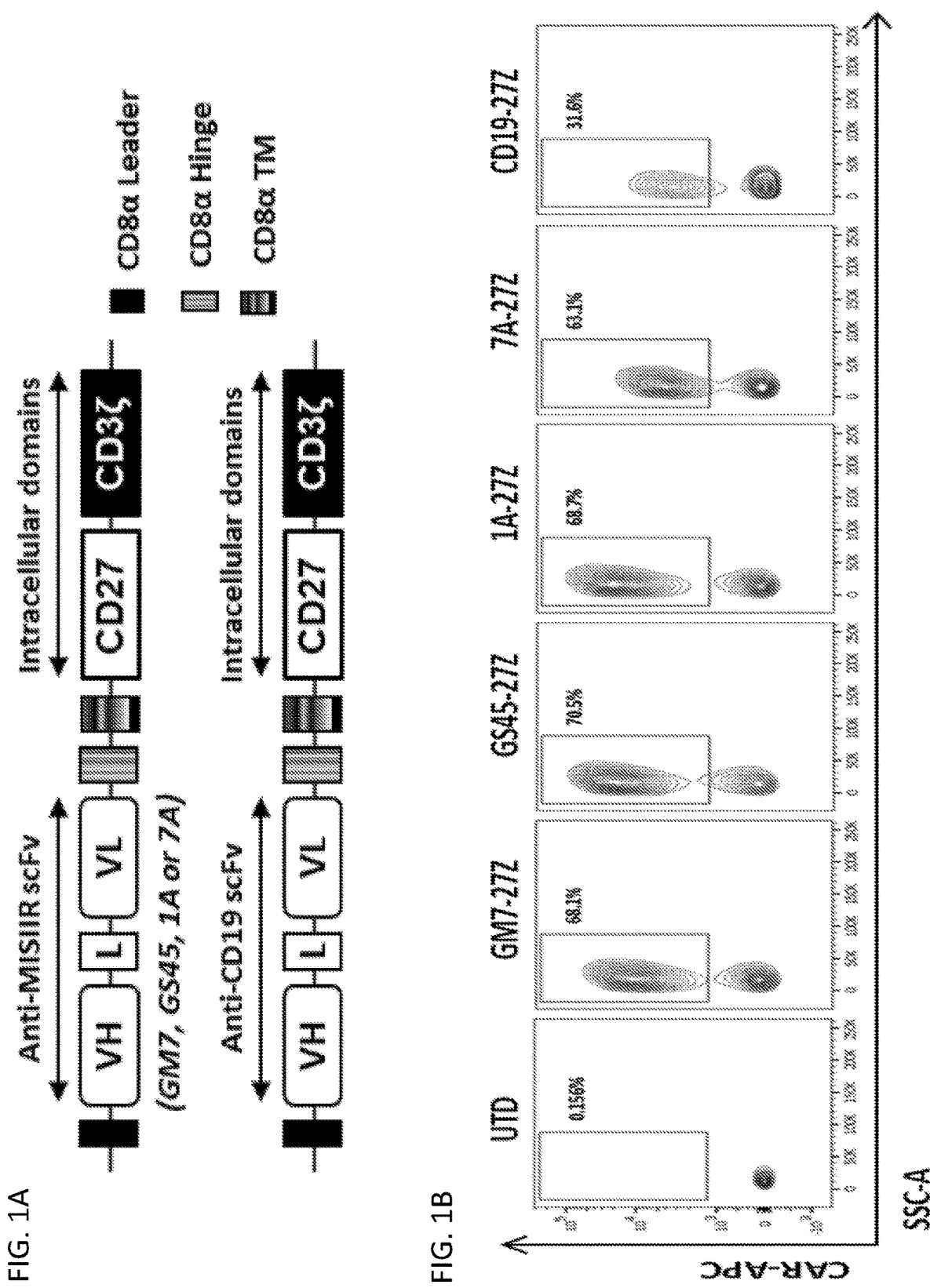
FIGS. 1A-1D depict data showing MISIIR-specific CARs are efficiently expressed on the surface of transduced primary T cells and are able to specifically bind and secrete IFNγ when incubated with recombinant target protein.
Figure 1C:
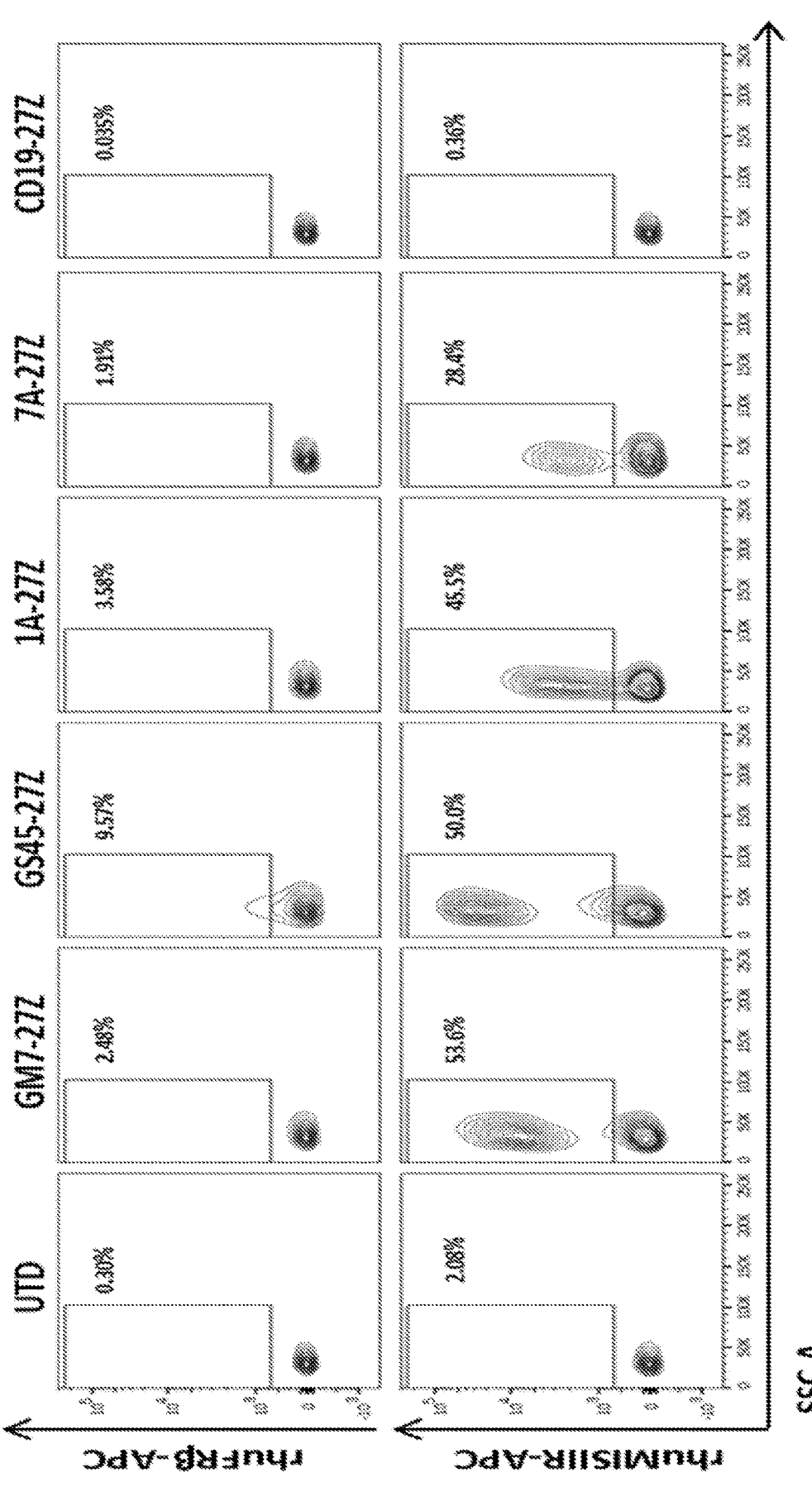
Figure 1D:
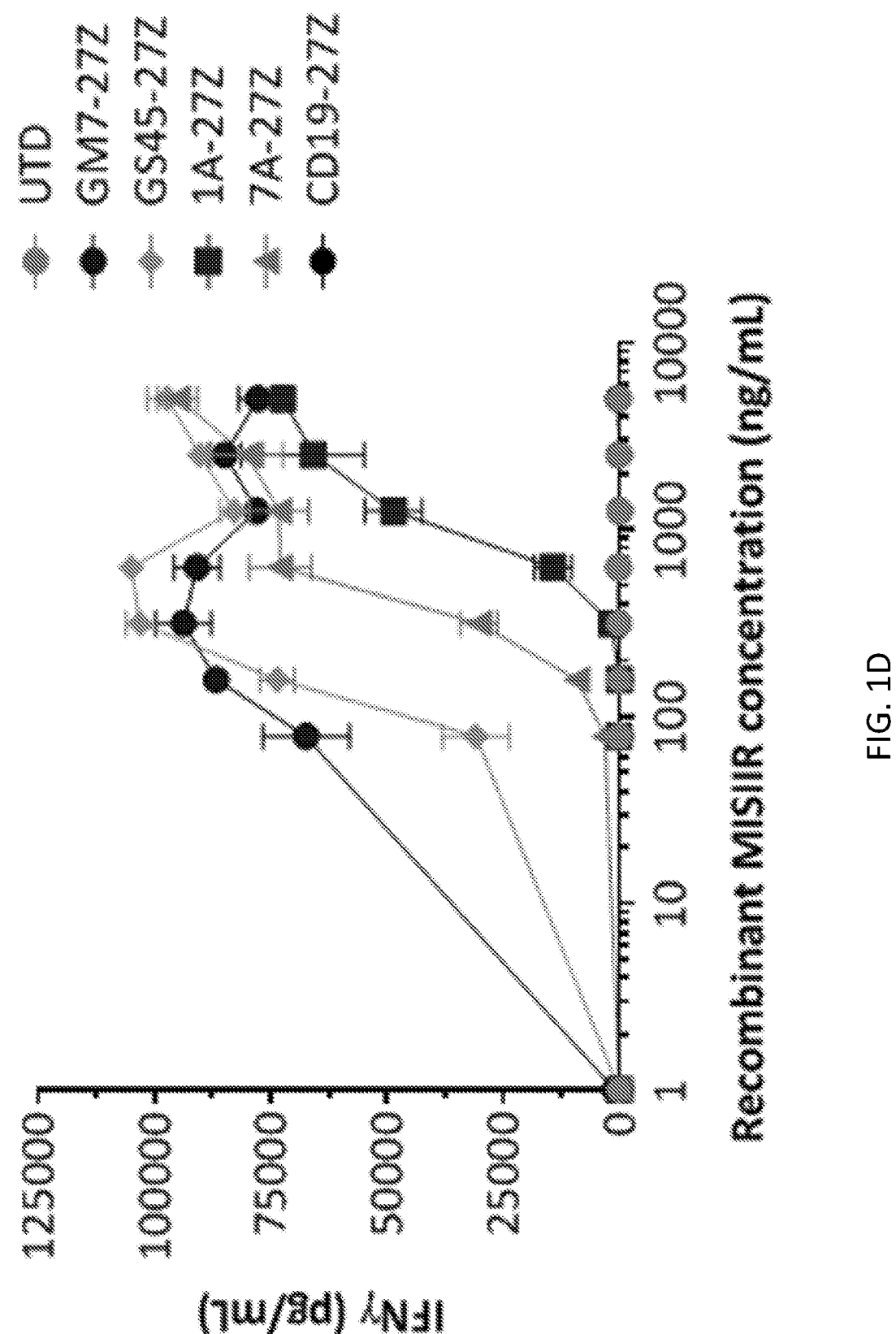

MISIIR-specific CAR T cells were generated herein. Four different human MISIIR-specific single-chain antibody variable fragments (scFvs) were isolated from a phage display library (GM7, GS45, 1A, and 7A) and coupled to CD27 and CD3ζ intracellular signaling domains (FIG. 1A). CARs were expressed on the surface of primary T cells (FIG. 1B) and demonstrated specific binding (FIG. 1C) and dose-dependent IFNγ secretion (FIG. 1D) upon incubation with increasing concentrations of recombinant target protein in vitro.

Figures 2A, 2B:
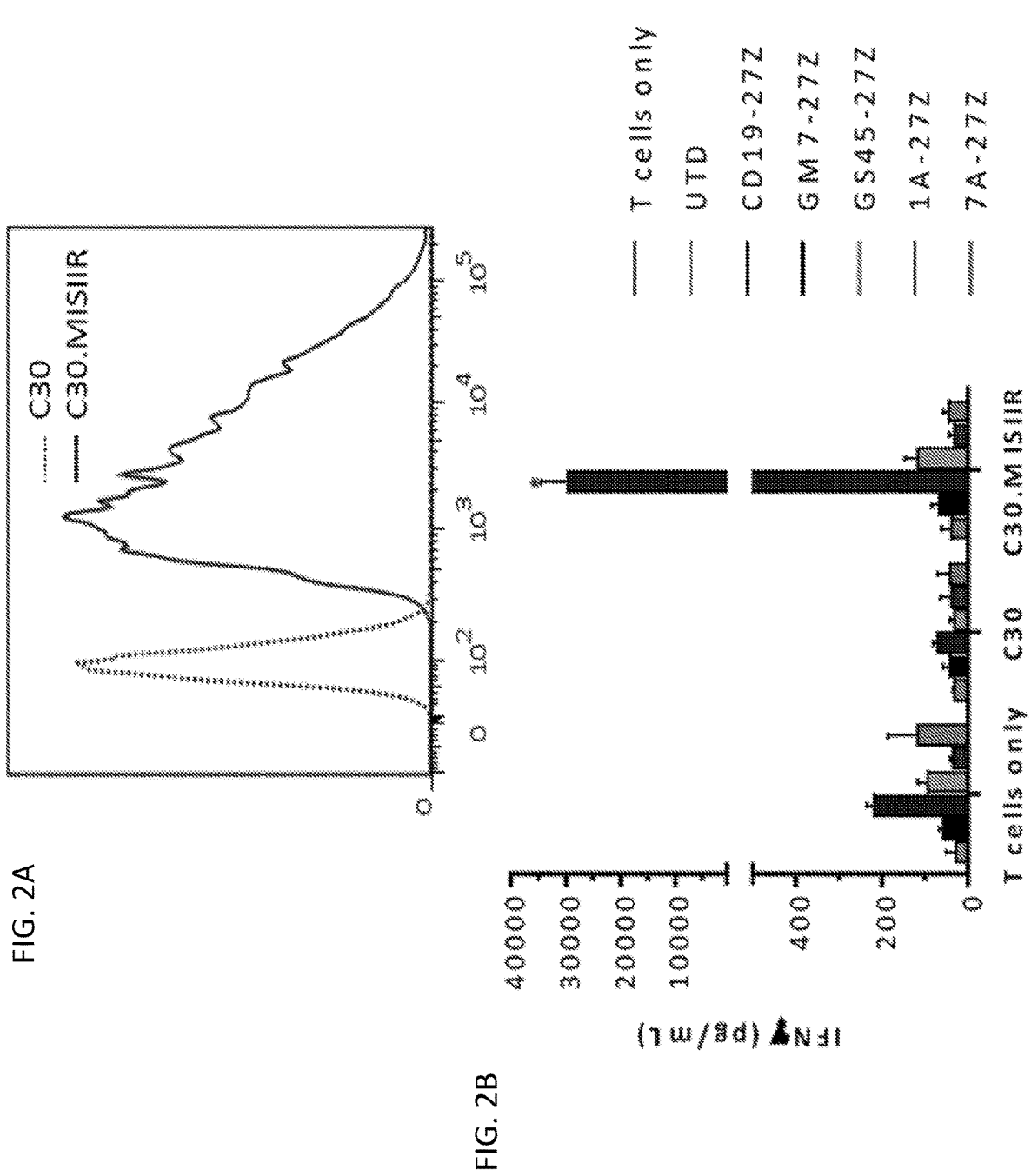
FIGS. 2A-2F depict data demonstrating the GM7-27Z CAR shows specific activation and response against a tumor cell line engineered to express MISIIR.
Figure 2C:
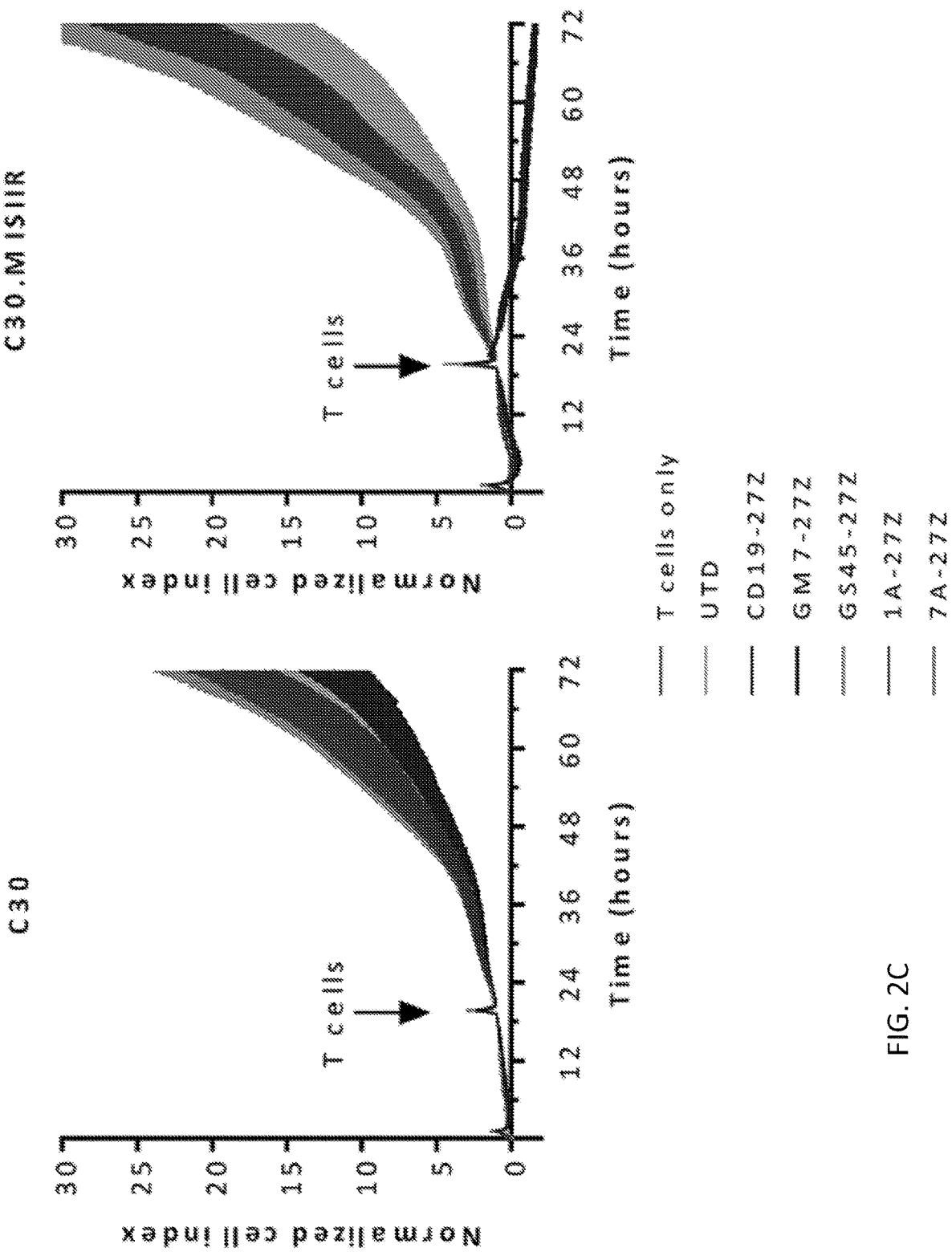
Figure 2D:
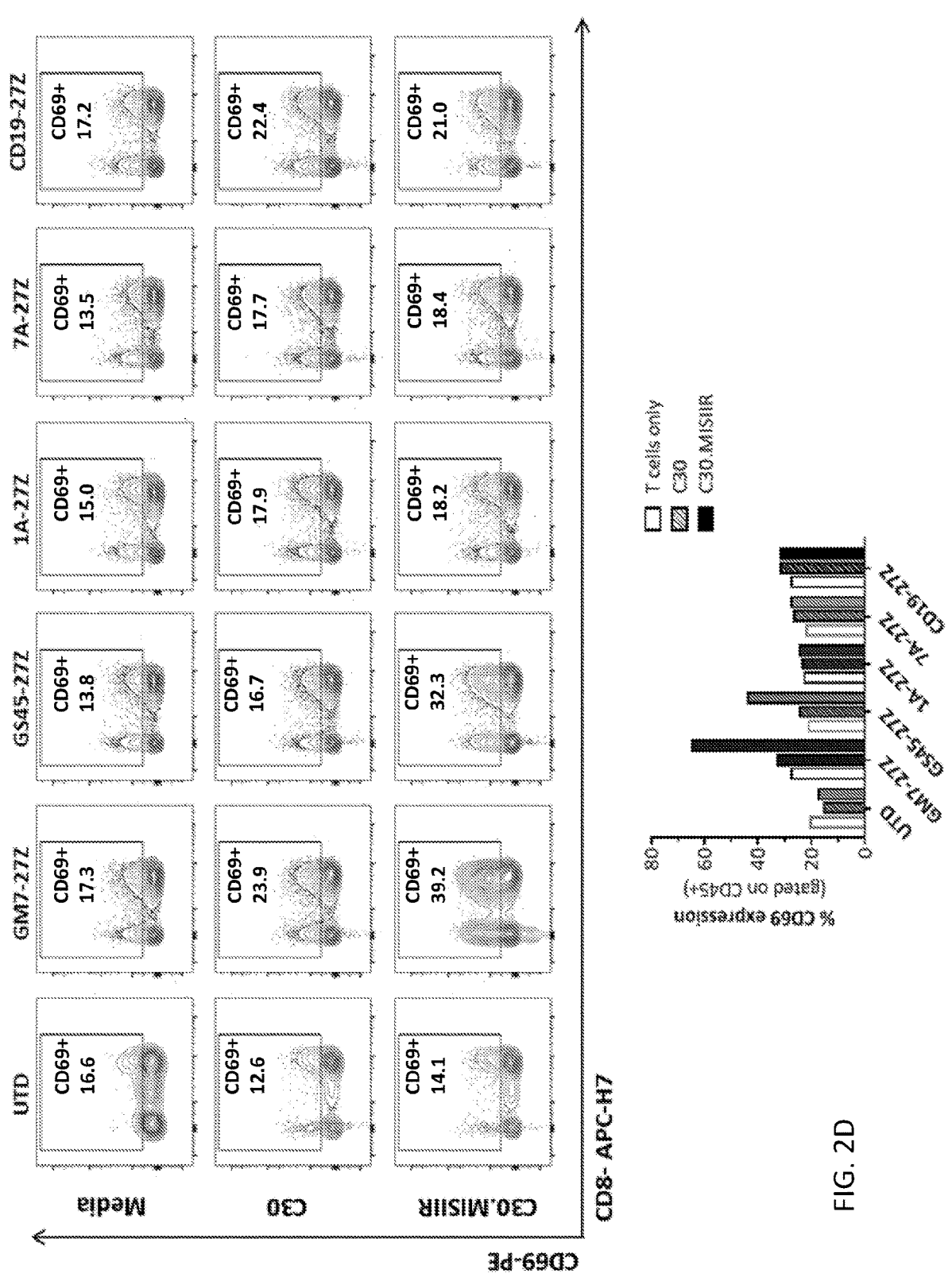
Figure 2E:
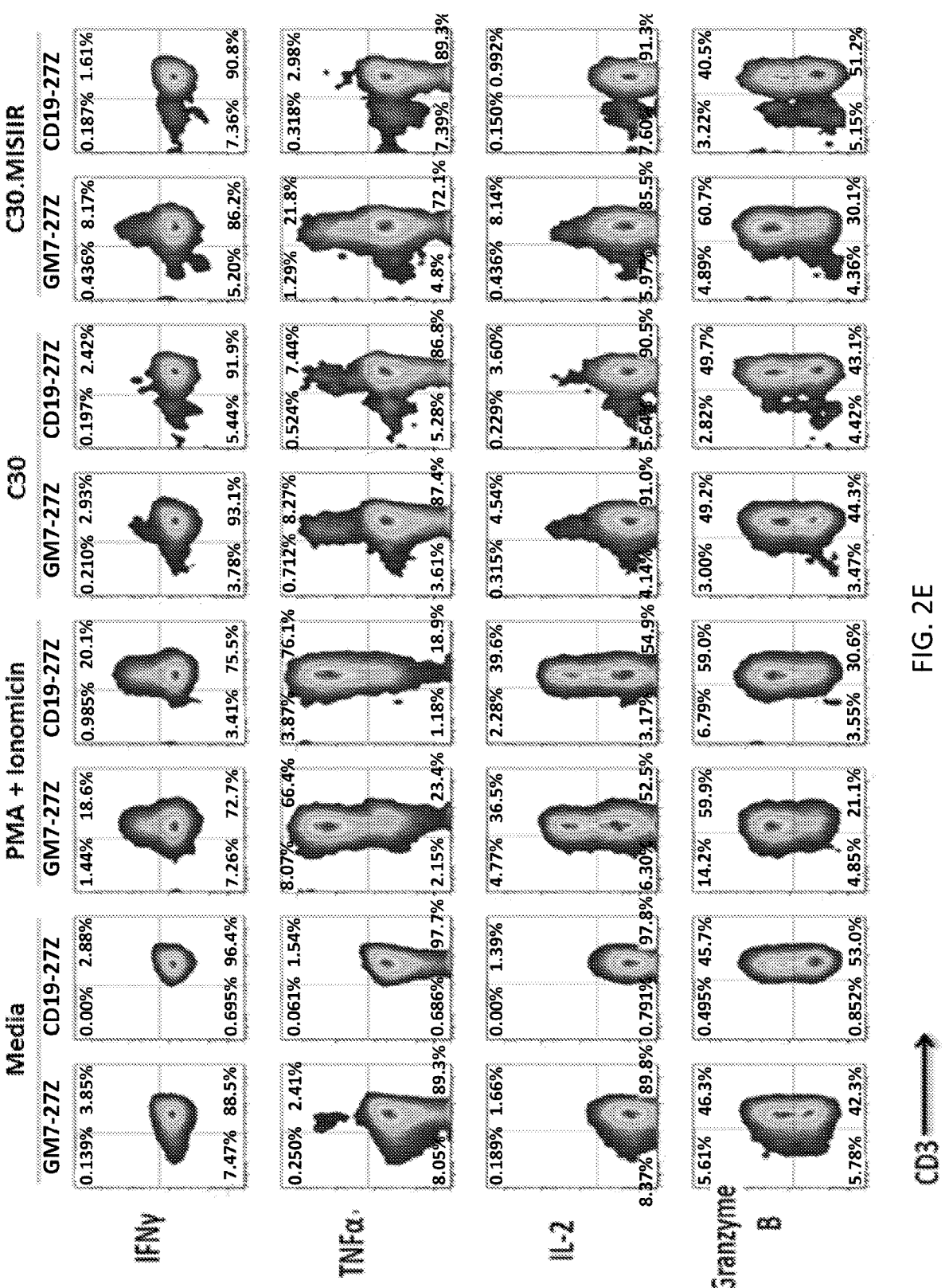
Figure 2F:
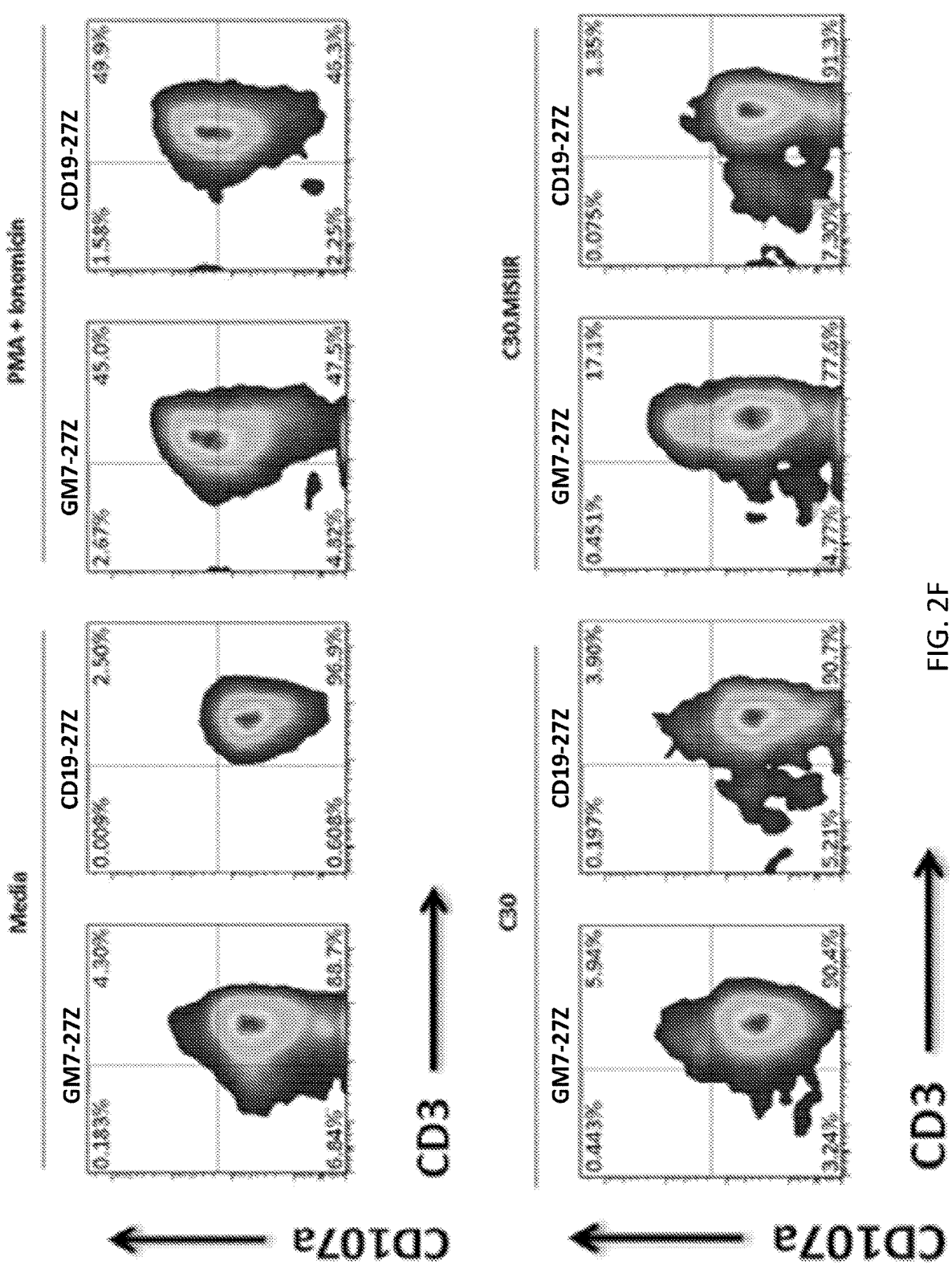
Figures 3A, 3B:
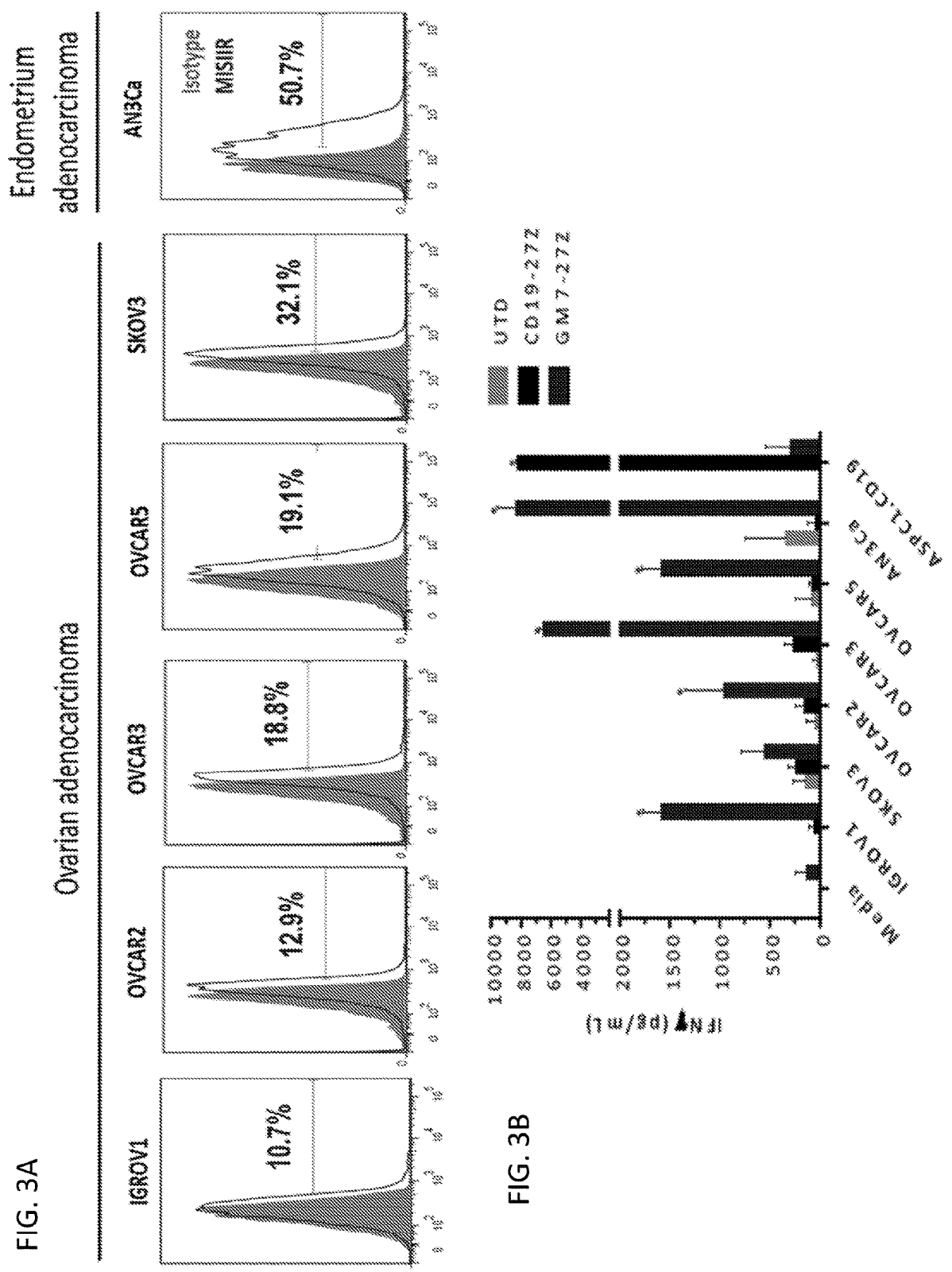
FIGS. 3A-3C depict data demonstrating the antitumor response of GM7-27Z CAR against a panel of tumor cell lines naturally expressing MISIIR.
Figure 3C:
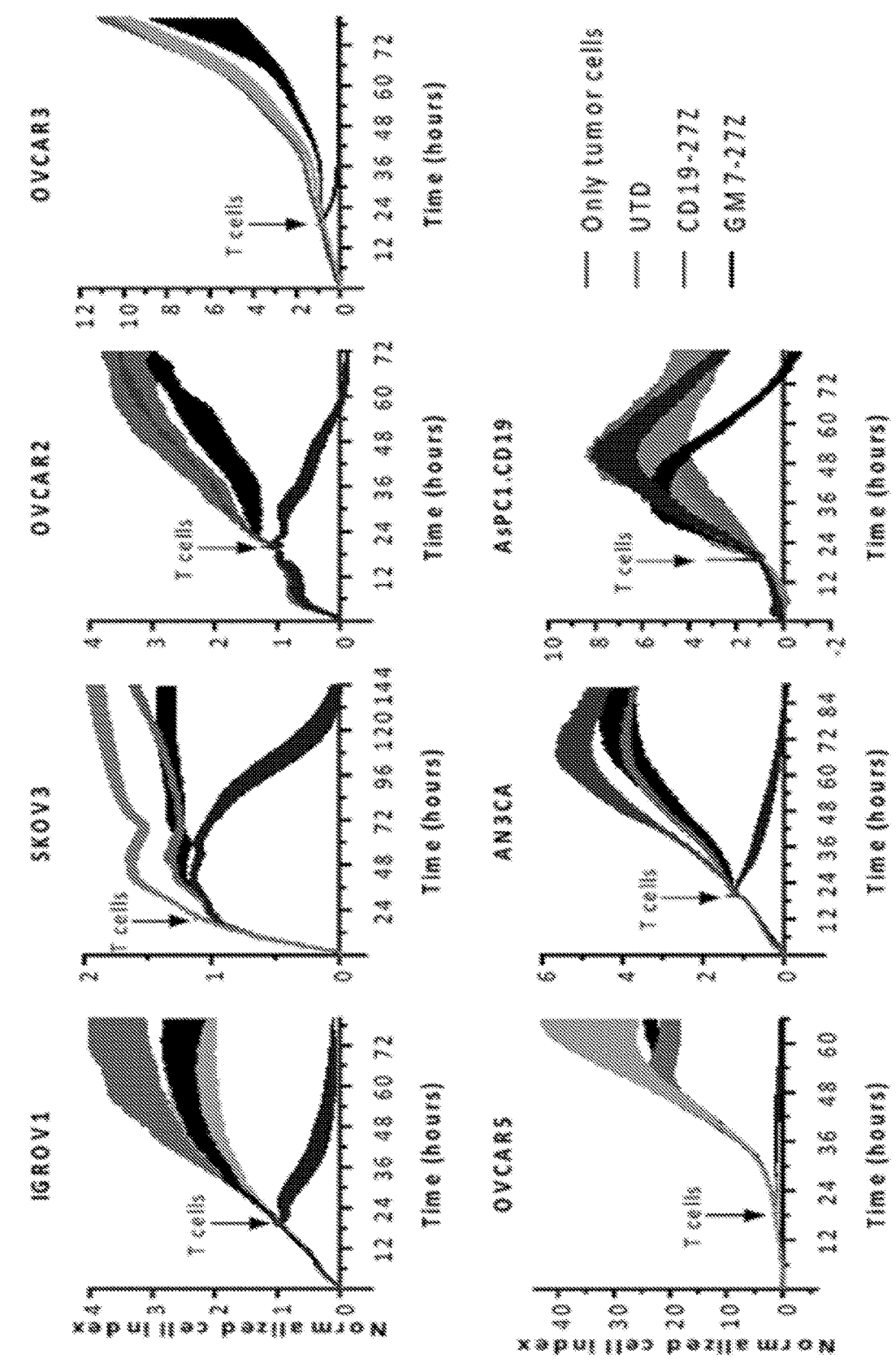
Figure 4:
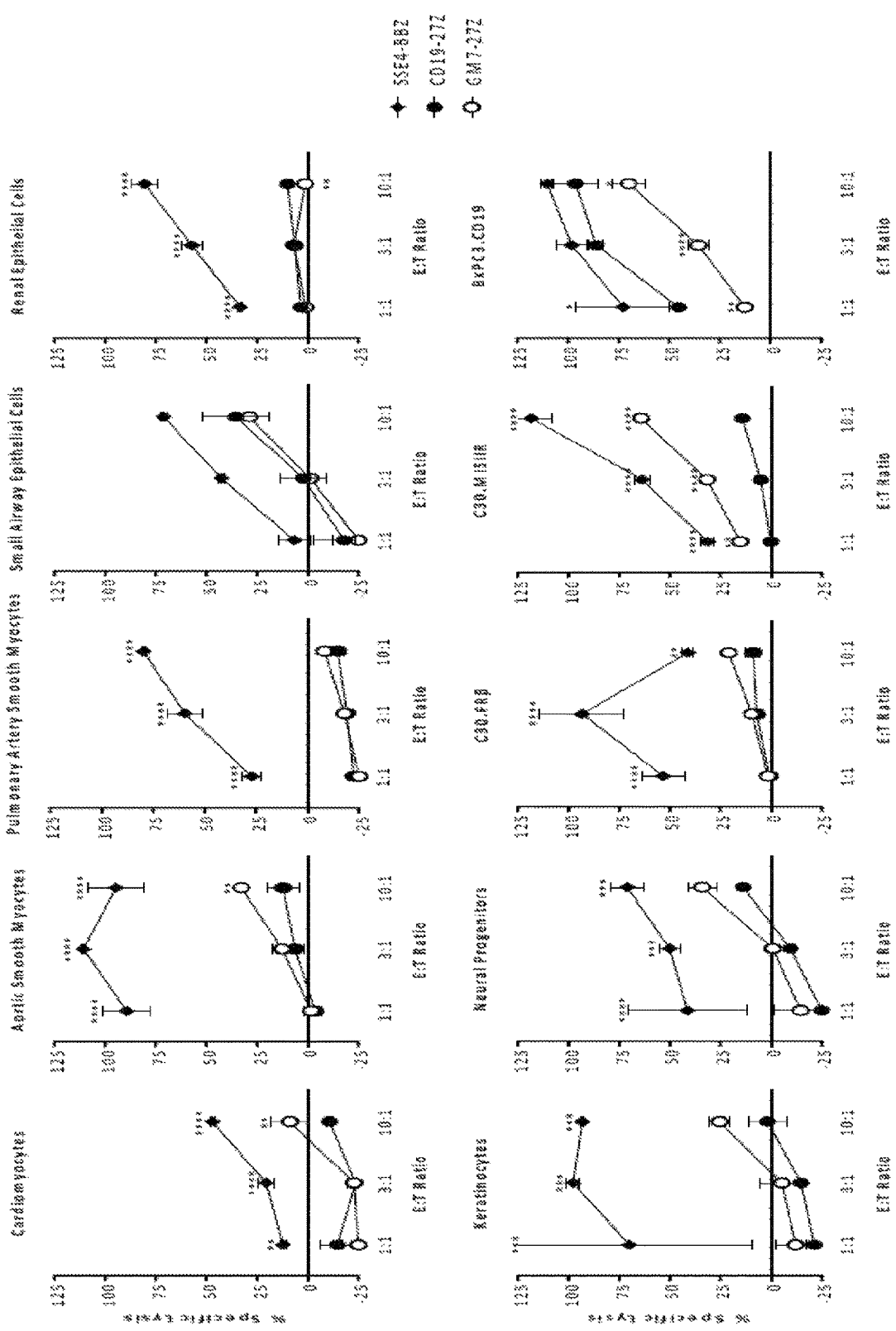
FIG. 4 depicts cytotoxicity data from GM7 CAR T cells co-cultured with a broad panel of normal primary human cells.

The distinct CAR T cell variants were compared in vitro in terms of antigen-specific cytokine secretion and cytotoxicity when co-cultured with antigen-deficient tumor cells (C30) or with target cells engineered to overexpress MISIIR (C30.MISIIR) in order to select the best in class CAR (FIGS. 2A-2F). The selected CAR, namely GM7-27Z, also showed antigen-specific reactivity against a broad range of human tumor cell lines including ovarian and endometrial cancer expressing variable levels of endogenous MISIIR (FIGS. 3A-3C). Importantly, GM7 CAR T cells didn't show any cytotoxicity when co-cultured with a broad panel of normal primary human cells, suggesting a safe profile of targeting MISIIR with CARs (FIG. 4).

Figure 5A:
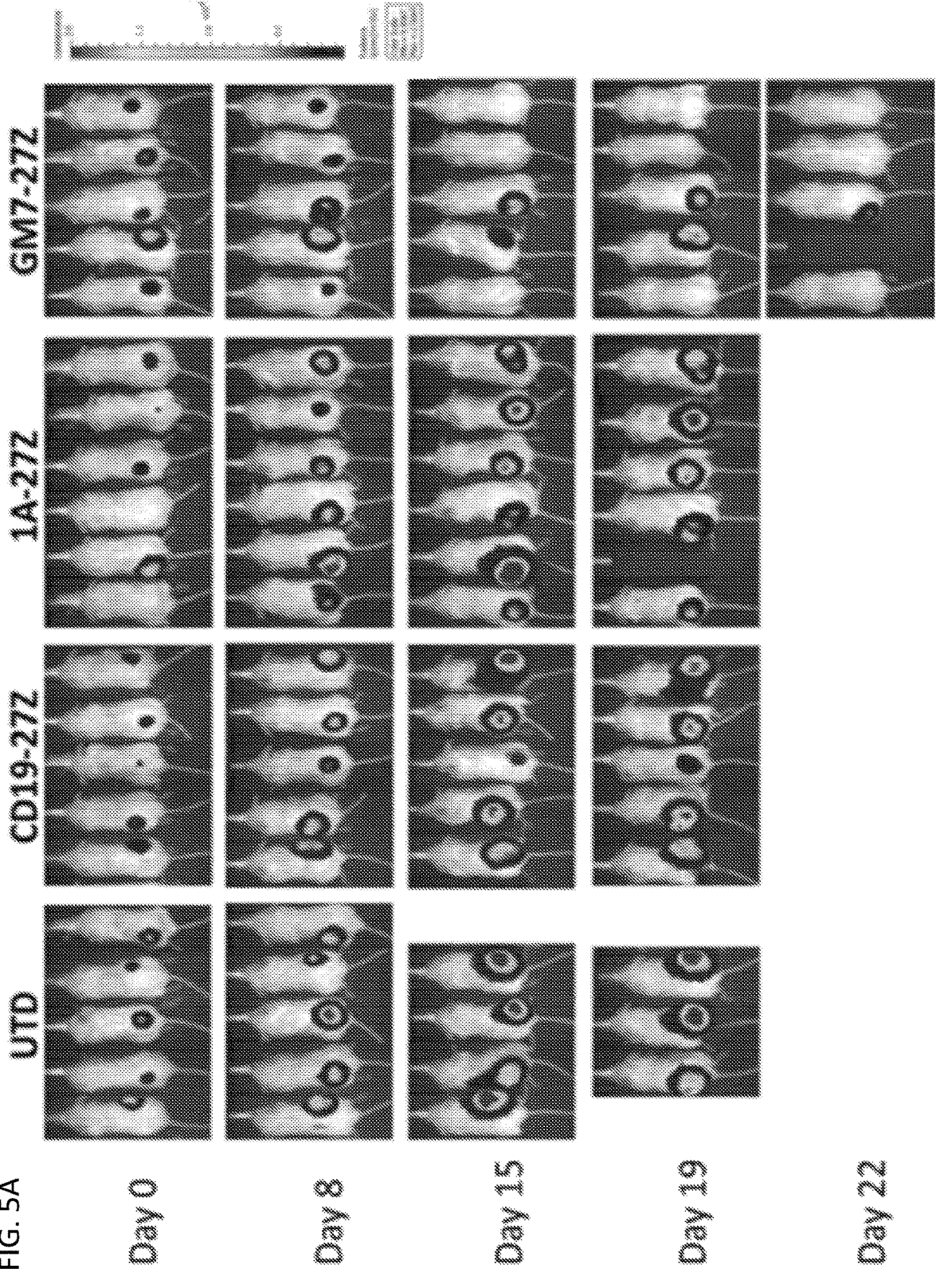
FIGS. 5A-5B depict data demonstrating in vivo antitumor activity of the GM7-27Z CAR in immunocompromised mice bearing large established subcutaneous C30.MISIIR tumors.
Figure 5B:
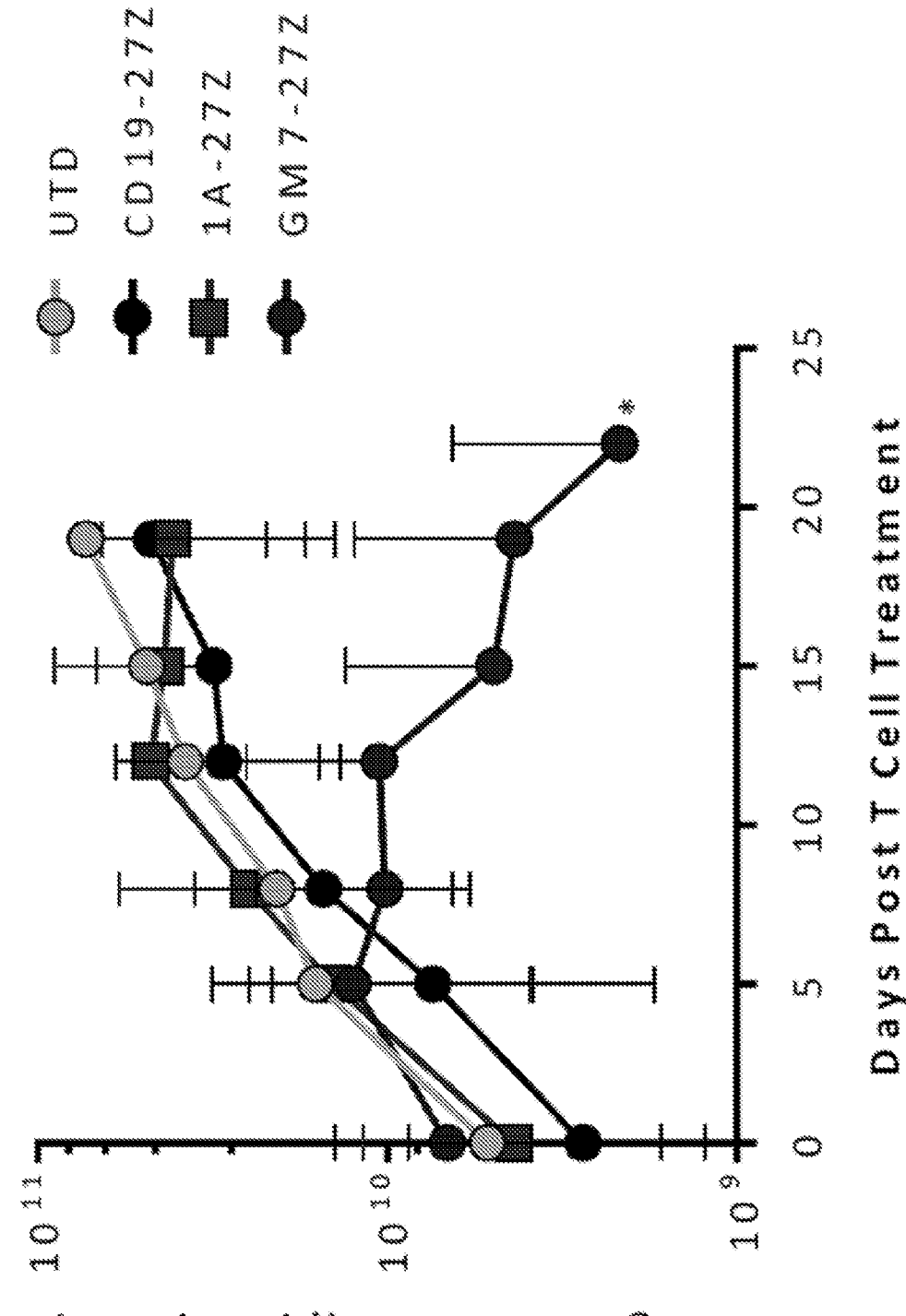

When tested in vivo, GM7 CAR T cells showed potent antitumor effect in immunocompromised mice bearing large established subcutaneous C30.MISIIR tumors, completely clearing 60% of the tumors and significantly prolonging mice survival (FIGS. 5A-5B). Nevertheless, while statistically significant, antitumor effect was mild when assessed in more aggressive tumor models which expressed lower endogenous levels of MISIIR (FIGS. 6A-6B).

Finally, to validate the applicability of this therapy to actual patients, GM7 CAR T cells were tested in vitro with patient-derived ovarian cancer cells. Importantly, MISIIR-specific CAR T cells showed antigen-specific upregulation of T cell activation markers as well as specific cytokine secretion and tumor cell lysis when co-cultured with tumor digests or established primary tumor cell cultures (FIGS. 7A-7C).

Overall, these data demonstrate that MISIIR is a novel target for the efficacious and safe treatment of ovarian cancer and other gynecologic malignancies using CAR T cell therapy.

Example 2: GM7 CAR T Cells Exhibit Antigen-Specific Reactivity Against Cell Surface MISIIR To test and compare the specific reactivity of the different CAR constructs against cell surface-expressed MISIR, the human OC cell line C30, which lacks natural MISIIR surface expression, was engineered to constitutively express the target antigen (C30.MISIIR: FIGS. 8A, 8B, and 2A). After the various CAR T cells were co-cultured overnight with either parental C30 or C30.MISIIR, only GM7 and GS45 CAR T cells exhibited antigen-driven upregulation of the activation marker CD69 in response to C30.MISIIR but not C30 cells. 1A and 7A CARs did not confer reactivity (FIG. 14). Supernatants from the same co-cultures were assayed for IFN-γ by ELISA, and only GM7 CAR T cells secreted high levels of IFN-γ in response to C30.MISIIR target cells (FIG. 2B). Consistent with this result, GM7 was the only CAR capable of specifically lysing C30.MISIIR target cells while sparing parental C30 cells, as measured in a real-time cytotoxicity assay (FIG. 2C). Despite showing antigen-specific binding and reactivity against rhMISIIR protein, GS45, 1A, nor 7A CAR displayed antigen-specific reactivity when the target was expressed on the surface of tumor cells. The possibility that the MISIIR epitopes recognized by these latter scFvs were not accessible by the CARs due to their relatively short hinges was considered. However, the replacement of the CD8a hinge by a longer immunoglobulin (Ig)G4-Fc-derived hinge (45aa versus 228aa long) in the CAR constructs did not restore the reactivity of GS45, 1A, or 7A constructs, nor did it alter cytokine secretion levels by GM7 in co-culture with MISUR-engineered C30 target cells (FIGS. 15A and 15B). Therefore, the GM7-27Z CD8a hinge was selected as the lead candidate anti-MISIIR CAR to advance.

Next, GM7 CAR (or control UTD and CD19 CAR) T cells were co-cultured for 5 h with C30 or C30.MISIIR cells, and production of the proinflammatory cytokines interleukin-2 (IL-2), tumor necrosis factor a (TNF-a) and IFN-γ was analyzed using intracellular cytokine staining. Degranulation, quantified by increased cell surface CD107a expression as a surrogate for T cell lytic function, was also assessed. A specific increase in each of these markers of CAR T cell response was observed solely in GM7 CAR T cells in the presence of C30.MISIIR (FIG. 2F).

Example 3: GM7 CAR T Cells Mediate Antitumor Activity In Vivo

Having observed that GM7 CAR T cells mediate responses against C30.MISIIR cells in vitro, their antitumor activity was investigated in a preclinical model. Non-obese diabetic (NOD)/severe combined immunodeficiency (SCID)/Y-chain–/– (NSG) mice previously inoculated subcutaneously with C30.MISIIR cells were treated with UTD, CD19 CAR, non-reactive 1A anti-MISUR CAR, or GM7 CAR T cells. Tumor progression was evaluated by luminescence (FIG. 9A) and caliper measurements (FIGS. 9B and 9C). Mice receiving UTD or control CAR T cells showed clear evidence of tumor progression and eventually had to be euthanized due to large tumor burden. In contrast, treatment with GM7 CAR T cells completely eradicated tumors in three out of five treated mice, which remained clear of disease until the end of the experiment, 26 days after CAR T cell administration (tumors were not palpable and the bioluminescence signal was reduced to background levels from that time point forward), and controlled tumor progression in another mouse. Treatment with GM7 CAR T cells significantly prolonged survival as compared with mice from the control groups (FIG. 9D). Signs of graft-versus-host disease (GVHD) were not observed at the endpoint of the in vivo study.

Example 4: GM7 CAR T Cells Demonstrate Antigen-Specific Reactivity Against Endogenous MISIIR GM7 CAR T cell function was next evaluated against a panel of human tumor cell lines that express endogenous MISIIR at variable levels. Six different cell lines with previously reported MISIIR expression were assayed, including ovarian (IGROV1, SKOV3, OVCAR2, OVCAR3, and OVCARS) and endometrial (AN3CA) cancer cell lines. Immunohistochemistry (IHC) staining of tumor cell pellets confirmed MISIIR expression (FIG. 16A). Surface MISIIR expression was also assessed by flow cytometry using multiple commercially available antibodies (Ab64762, PAS-13901, and AF4749) (FIG. 16B). Only one of those antibodies, Ab64762 (FIG. 16B, top panel), showed detectable surface levels of MISIIR at any level among the different cell lines.

After overnight co-culture of CAR T cells with target cells, supernatants were collected and assayed for IFN-γ by ELISA. GM7 CAR T cells secreted IFN-γ in response to target cells expressing endogenous MISIIR, while UTD or CD19 CAR T cells did not (FIG. 3B). GM7 CAR T cells also specifically lysed all MISIIR-expressing cell tar-gets (FIG. 3C). At this point, the activity of GM7 CAR against cancer cell lines with natural MISIIR antigen expression was compared in the context of short CD8a or longer IgG4-Fc derived hinges, as well as CD27 or CD28 co-stimulatory domains. Higher levels of IFN-γ were secreted by the CAR containing the shorter hinge in co-culture with at least three out of the four MISIIR-expressing tumor cell lines tested (FIG. 15C). Also, the CD28 co-stimulated CAR functioned specifically, albeit with reduced activity as compared to a CD27 CAR (FIG. 17).

Antitumor efficacy in vivo was then tested in OVCAR3 and OVCARS OC xenograft models as well as in an AN3Ca endometrial cancer model. In all three tumor models, tumor growth was rapid and aggressive. Nevertheless, tumors from mice treated with GM7 CAR T cells were 1.5-fold smaller than tumors in UTD and CD19 CAR control-treated groups at the study endpoint in OVCAR3 and OVCARS models. In the AN3Ca model, tumor volume was 1.8- and 2.2-fold lower in GM7-treated mice at the end of the experiment, compared to UTD and CD19 CAR-treated groups, respectively (FIG. 10, FIG. 18A). In addition, in the AN3Ca tumor model, higher concentrations of circulating CD3+ T cells were detected 18 days after T cell administration in mice treated with GM7 CAR as compared to mice from the UTD group (FIG. 18B), as well as a trend to higher frequencies of CD45+ cells infiltrating the tumors at the endpoint of the experiment (FIG. 18C).

Example 5: The Killing Mechanism of GM7 CAR T Cells does not Involve Ligand-Induced Apoptosis The natural ligand for MISIIR, MIS, triggers cancer cell apoptosis by engaging MISIIR; however, producing large quantities of rhMIS protein for the treatment of patients has been challenging. Alternatively, MISIIR-specific antibodies that induce apoptosis upon receptor engagement have been previously reported. To test the hypothesis that anti-MISIIR CARs can trigger cancer cell apoptosis in a manner analogous to MIS, a signaling-deficient CAR, GM7-AK, that is able to bind to MISIIR through the extracellular scFv domain but is incapable of signaling through the T cell intracellular domains to initiate T cell activation was created (FIG. 11A). GM7-AK was detected on the cell surface at similar levels than GM7-27Z, demonstrating that deleting CD27-CD3 domains did not impact surface expression of the CAR (FIG. 11B). AN3Ca or OVCARS cells, which are MIS responsive, were co-cultured with GM7 CAR T cells or its signaling-deficient Δζ counterpart and evaluated for induction of apoptosis. In spite of the capacity of GM7 scFv to bind to MISIIR, the GM7-Δζ CAR was unable to trigger apoptosis in MISIIR-expressing target cells (FIG. 11C, 11D). Real-time cytotoxicity assays (FIG. 11E) and MTS cell proliferation assays (data not shown) confirmed that constructs that contain only the extracellular part of the CAR without intracellular signaling capacity were not able to inhibit tumor growth in an activation-independent manner. Similar results were observed using IGROV1 targets cells (FIGS. 19D-19F), which are also MIS responsive, or in the engineered model C30.MISIIR (FIGS. 19A-19C). These data indicate that MISIIR CAR-mediated killing of cancer cells is highly dependent on CAR T cell activation.

Example 6: GM7 CAR T Cells Show Reactivity in PD Tumor Specimens

As a route toward future clinical application, GM7 CAR T cells were tested against PD tumor specimens in vitro. Samples from two different high-grade serous OC (HGSOC) PD tumors (W012 and W019) were obtained and confirmed for positive human MISIIR mRNA expression by quantitative real-time PCR, as compared to the negative cell line C30 (FIG. 12A). W012 or W019 tumor cells were co-cultured overnight alone or with GM7 CAR, control CD19 CAR, or UTD T cells. T cells were then assessed for the expression of CD69 and CD137 (4-1BB) T cell activation markers. Significant antigen-driven upregulation of both activation markers was observed in GM7 CAR, but not control, T cells when co-cultured with either W012 or W019 tumor cells (FIG. 7A). GM7 CAR T cells also demonstrated antigen-specific antitumor activity against W012 and W019 cells in real-time cytotoxicity assays (FIG. 7C).

Example 7: GM7 CAR T Cells do not Mediate Detectable On-Target Off-Tumor Toxicity Despite the restricted expression profile of MISIIR in normal tissues, on-target off-tumor toxicity is a key factor to be considered when developing novel CAR T therapies. To begin to address this concern, GM7 or CD19 CAR T cells were co-cultured at different effector-to-target (E:T) ratios with a panel of primary human normal cell lines derived from aortic and pulmonary myocytes, small airway and renal epithelial cells, neuronal progenitors, and keratinocytes, and chromium release cytotoxicity assays were performed. Selection of these cell types was based on reported low levels of MISIIR protein expression in the literature as well as cell availability. A CAR specific for SSEA4, named MC813-70, which demonstrates normal tissue toxicity, was used as a positive control for normal cell targeting. Similar to CD19 CAR T cells, whose on-target off-tumor toxicity is limited only to CD19+ normal B cells in patients, GM7 CAR T cells showed no reactivity against this limited panel of normal human primary cells, except for low level lysis of aortic smooth myocytes that was only observed at the highest E:T ratio tested (10:1). Importantly, no killing was observed for the same cell type obtained from pulmonary artery. GM7 CAR T cells did lyse positive control C30.MISIIR cells. In contrast, MC813-70 CAR T cells lysed all target cells tested (FIG. 4). The potential for toxicity in the various preclinical xenograft models was next evaluated. These studies bear significance since the GM7 CAR is cross-reactive with the mouse MISIIR homolog, resulting in mMISIIR-specific T cell release of IFN-7 (FIG. 20A) as well as mMISIIR-specific tumor cell lysis in vitro (FIG. 20B) of the mouse OC cell line ID8, which expresses mMISIIR. In all of the preclinical studies performed, there was no overt evidence of toxicity associated with the administration of GM7 CAR T cells to mice, as measured by body weight loss and physical signs of toxicity.

Example 8: Discussion

Herein, the present disclosure describes a CAR designed to target human MISIIR for the treatment of gynecologic cancers. MISIIR is expressed at high levels in OC and also in endometrial cancer, a disease for which novel therapeutic strategies are more limited and in need. Moreover, the applicability of this form of therapy can be broadened to include cervical, breast, prostate, and lung cancer, and ocular melanoma.

CAR T cells have shown dramatic clinical success for the treatment of hematologic malignancies. The facts that (1) OC patients whose tumors are infiltrated by T cells have better overall survival, and (2) ovarian tumors express targetable tumor-associated antigens on their surface provide the rationale for developing CAR T cell therapies in this disease. In gene-engineered T cell trials for OC that target antigens such as FRα, NY-ESO-1, Her2, MSLN, or MUC16, T cell therapy has yet to recapitulate the success of CD19 CAR T cell therapy in cancers of the blood. One challenge to designing effective CAR T cell therapy for solid tumors is the selection of an appropriate target antigen that is selectively, highly, and homogeneously expressed in tumor cells. Given the established relevance of the MIS/MISIIR pathway in cancer, as well as the challenges associated with the large-scale production of rhMIS protein for therapeutic use, a different strategy was developed of targeting MISIIR using a CAR T cell approach.

In the present disclosure, all of the CAR constructs generated are based on fully human scFvs, avoiding potential issues related to transgene immunogenicity. While all of these MISIIR CARs conferred T cells with the ability to recognize rhMISIIR protein, only one CAR construct, namely GM7, was capable of redirecting T cell activity against MISIIR expressed on the cell surface. The reason for which the rest of the CAR constructs did not show reactivity against C30.MISIIR target cells remains unclear, although it does not appear to be related to CAR expression, affinity of the scFv for the target, or overall targeting, as MISIIR is expressed at very high levels in the engineered cell line. In an extensive set of in vitro assays, GM7 CAR T cells specifically and reproducibly recognized MISIIR-expressing ovarian and endometrial cancer cells, produced multiple pro-inflammatory cytokines, and mediated cancer cell cytolysis.

Although CD28 or 4-1BB co-stimulated CAR constructs are already validated in patients and CD19 CAR T cells based on both co-stimulatory domains have been US Food and Drug Administration (FDA) approved recently, the CD27 co-stimulation domain was used in the constructs. CD27 belongs to the same family as 4-1BB, and very similar features have been observed between them in the context of an anti-FRα CAR. Both CD28 and CD27 moieties were directly compared in the context of GM7 CAR, with CD28 showing a slower killing kinetics in vitro as well as lower levels of IFN-γ secretion when co-cultured with any one of four different tumor cell lines (IGROV1, OVCAR3, OVCARS, and AN3Ca) as compared to the CD27 counterpart (FIG. 17).

In an earlier study, one antibody specific for MISIIR, 12G4, was reported to induce apoptosis in MISIIR-expressing tumor cell lines, prompting us to hypothesize that CAR T cells might have a similar effect and induce tumor cell death by dual mechanisms of MISIIR receptor engagement as well as by T cell-mediated cytotoxicity. This hypothesis was not supported by the finding that the GM7-Δζ CAR, which engages MISIIR protein but lacks intracellular T cell activation potential, was unable to induce cancer cell apoptosis. The fact that 12G4 antibody and MIS protein bind to non-overlapping epitopes on MISIIR implies that receptor internalization may be critical to activate the signaling and degradation pathways, as opposed to a surface ligand-mimicking binding effect. In future studies, it may be beneficial to screen MISIIR scFvs for their ability to bind to the MIS-binding epitope or to induce apoptosis of target cells, prior to the generation and screening of new CARs.

In spite of its inability of induce apoptosis, the GM7 CAR allowed T cells to effectively lyse a range of tumor cell lines expressing variable surface levels of the MISIIR target antigen. A particularly relevant model used in this study was the PD tumor specimens. The possibility of establishing primary cell cultures from PD tumors is of great value to directly test therapeutic strategies for individual patients in a relatively rapid manner. In a recent study, MISIIR protein expression was detected in 16 PD tumor cell lines. Regardless of the limited number of samples utilized in this study, the two tumors tested expressed significant levels of MISIIR as compared to a negative tumor cell line. GM7 CAR T cells specifically recognized and reacted in co-culture with both MISIIR-expressing PD tumor samples, WO12 and WO19, demonstrating the potential of the treatment of OC patients with this CAR approach.

Using the high ectopic MISIIR-expressing C30.MISIIR xenograft model, complete tumor eradication was observed in three of five treated mice, with tumor outgrowth ultimately occurring in the other two mice. In the case of other aggressive xenograft models, where MISIIR is naturally expressed at more moderate levels, the in vivo efficacy of GM7 CAR T cells was modest. When MISIIR expression on the remaining tumor was assessed by qPCR, lower, albeit non-significant, levels were detected, as compared to tumors from mice treated with control UTD or unspecific CD19 CAR T cells, suggesting that antigen downregulation or loss might be occurring as a means of escape. Beyond antigen loss and lower expression levels of surface target, heterogeneous expression of MISIIR in tumors might limit efficacy. In one study looking at OC patient specimens, expression percentages in MISIIR-expressing cases ranged between 20% and 95%, suggesting that MISIIR heterogeneous expression may exist in patients. Another study also found variable levels of MISIIR expression in different tumor cores from the same patient, with some cores that were negative for MISIIR staining within the same cases. Combinatorial targeting of multiple antigens co-expressed in OC might be needed to overcome this issue. This strategy is being tested clinically in the case of CD19 loss in relapsed patients treated with CD19 CAR T cells by additionally targeting the antigen CD22.

High levels of MISIR expression in adults is confined to granulosa cells in the ovary, as well as Sertoli and Leydig cells in the testis. In the largest study of MISIIR expression in gynecologic tumors and benign tissue reported to date, MISIIR protein was detected in 28% of the tested normal endometrium samples (versus 75% of endometrial cancer specimens), fallopian tube, and placenta in women. Weak IHC staining of MISIIR was also revealed in selected normal non-gynecologic tissues such as liver parenchyma, bronchiolar epithelium, small intestine mucosa, kidney, adrenal, pancreas, and breast ducts, and at lower levels in tonsil, lymph nodes, and arterial smooth muscle. Importantly, 74% of human normal tissues evaluated did not express MISIIR protein.

In the present disclosure, activity of GM7 CAR T cells was evaluated in vitro against a normal cell panel that included cells from some of the tissues reported to express MISIIR protein, such as renal epithelial cells, small airway epithelial cells, or artery smooth myocytes. Neural progenitors were also included, as expression of MISIIR mRNA and protein in motor neurons has been reported in mice (although not in humans). In general, GM7 CAR T cells did not recognize normal cells. However, a very low level of aortic smooth myocyte lysis was observed and only at the highest E:T ratio tested, but lysis of smooth myocytes obtained from the pulmonary artery was not detected. Whether this in vitro finding represents an experimental artifact is unclear, yet these results bear consideration when translating to the clinical setting. It is notable that many noncoding transcripts and alternative splice isoforms of MISIIR have been identified, some of which are retained in the endoplasmic reticulum (ER) and not expressed on the cell surface, making them unlikely targets for CAR T cells. In the preclinical models of the present disclosure, physical signs of GM7 CAR-associated toxicity were not observed in any experiment conducted, in spite of the established reactivity of the GM7 CAR against both human and mouse MISIIR protein homologs. Even if MISIIR is expressed in normal tissue, the level of MISIIR found in normal tissues has been reproducibly shown to be significantly lower than in malignant cells. In this setting, tuning the affinity and functional avidity of the CAR construct expressed in T cells may serve as a strategy to overcome any potential toxicity issues. Furthermore, the expression of higher levels of MISIIR in healthy gynecologic tissues is also manageable, as these reproductive tissues are not essential for sustaining the life of the patient, and some of which are commonly removed by surgical resection in advanced OC patients.

Herein, the present disclosure describes a MISIIR targeting strategy that relies on the use of CAR T cell technology. This alternative approach to MISIIR targeting overcomes the issues in generating sufficient quantities of rhMIS protein as a therapeutic agent and is backed by the effector functions of a T cell in order to deliver MISIIR-specific cytotoxicity. Taken together, the data presented herein serve as the foundation for the clinical development of MISIIR-specific CAR T cell therapy for the safe and efficacious treatment of MISIIR-expressing OC and other malignancies.

Other Embodiments

The recitation of a listing of elements in any definition of a variable herein includes definitions of that variable as any single element or combination (or sub-combination) of listed elements. The recitation of an embodiment herein includes that embodiment as any single embodiment or in combination with any other embodiment or portions thereof.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed:

1. A modified immune cell or precursor cell thereof, comprising:
   a chimeric antigen receptor (CAR), wherein the CAR comprises an antigen binding domain having affinity for Müllerian inhibiting substance type 2 receptor (MISIIR), a transmembrane domain, and an intracellular domain,
   wherein the CAR comprises the amino acid sequence set forth in SEQ ID NO: 2, and/or is encoded by the nucleotide sequence set forth in SEQ ID NO: 1.

2. The modified immune cell or precursor cell of claim 1, wherein:
   (a) the cell is an autologous cell; and/or
   (b) the cell is isolated from a human subject; and/or
   (c) the cell is a modified T cell.

3. A method of treating cancer in a subject in need thereof, the method comprising administering to the subject the modified immune or precursor cell of claim 1.

4. A method of treating a cancer in a subject in need thereof, comprising administering to the subject a modified T cell comprising: a chimeric antigen receptor (CAR), wherein the CAR comprises an antigen binding domain having affinity for Mullerian inhibiting substance type 2 receptor (MISIIR), a transmembrane domain, and an intracellular domain, wherein the CAR comprises the amino acid sequence set forth in SEQ ID NO: 2, and/or is encoded by the nucleotide sequence set forth in SEQ ID NO: 1.

5. The method of claim 4, wherein,
   (a) the cancer is selected from the group consisting of ovarian cancer, endometrial cancer, uterine sarcoma, cervical carcinoma, breast cancer, lung cancer, prostate cancer, ocular melanoma, a MISIIR-expressing tumor, and ovarian cancer; and/or
   (b) the modified T cell is human; and/or
   (c) the modified T cell is autologous; and/or
   (d) the subject is human.

*    *    *    *    *